(12) United States Patent
Singh et al.

(10) Patent No.: US 11,827,582 B2
(45) Date of Patent: Nov. 28, 2023

(54) SUBSTITUTED AMINES AS DISRUPTERS OF ABETA42 OLIGOMER FORMATION

(71) Applicant: ACELOT, INC., Palo Alto, CA (US)

(72) Inventors: Ambuj K. Singh, Santa Barbara, CA (US); Christian A. Lang, Santa Barbara, CA (US)

(73) Assignee: ACELOT, INC., Palo Alto, CA (US)

( * ) Notice: Subject to any disclaimer, the term of this patent is extended or adjusted under 35 U.S.C. 154(b) by 0 days.

(21) Appl. No.: 16/836,835

(22) Filed: Mar. 31, 2020

(65) Prior Publication Data

US 2020/0223788 A1 Jul. 16, 2020

Related U.S. Application Data

(62) Division of application No. 16/350,344, filed on Nov. 5, 2018, now Pat. No. 10,703,711.

(60) Provisional application No. 62/707,516, filed on Nov. 6, 2017.

(51) Int. Cl.
| | | |
|---|---|---|
| *C07C 211/23* | (2006.01) | |
| *C07C 233/43* | (2006.01) | |
| *C07C 271/18* | (2006.01) | |
| *A61K 31/135* | (2006.01) | |
| *A61K 31/137* | (2006.01) | |
| *C07C 223/02* | (2006.01) | |
| *C07C 211/28* | (2006.01) | |
| *C07C 211/29* | (2006.01) | |
| *A61K 31/131* | (2006.01) | |
| *C07C 211/27* | (2006.01) | |
| *C07C 217/60* | (2006.01) | |
| *C07D 207/06* | (2006.01) | |
| *C07D 295/135* | (2006.01) | |
| *C07D 295/15* | (2006.01) | |
| *C07D 319/18* | (2006.01) | |
| *C07D 413/06* | (2006.01) | |

(52) U.S. Cl.
CPC .......... *C07C 233/43* (2013.01); *A61K 31/131* (2013.01); *A61K 31/135* (2013.01); *A61K 31/137* (2013.01); *C07C 211/27* (2013.01); *C07C 211/28* (2013.01); *C07C 211/29* (2013.01); *C07C 217/60* (2013.01); *C07C 223/02* (2013.01); *C07C 271/18* (2013.01); *C07D 207/06* (2013.01); *C07D 295/135* (2013.01); *C07D 295/15* (2013.01); *C07D 319/18* (2013.01); *C07D 413/06* (2013.01)

(58) Field of Classification Search
CPC ... C07C 211/28; C07C 211/29; C07C 211/27; C07C 217/60; C07C 211/23; C07D 207/06; C07D 295/135; C07D 295/15; C07D 319/18; C07D 413/06; A61K 31/131

USPC .......................................................... 564/463
See application file for complete search history.

(56) References Cited

U.S. PATENT DOCUMENTS

2013/0143924 A1 6/2013 Ducray et al.
2021/0052519 A1* 2/2021 Singh ................... A61K 31/495

FOREIGN PATENT DOCUMENTS

WO WO 2002078693 * 10/2002

OTHER PUBLICATIONS

Lee, et al. Advanced Synthesis & Catalysis, 356(11-12), 2014, 2653-2660.*
Pubchem, Substrate Record for SID 319065898, Available Date: Nov. 25, 2016 [retrieved on Feb. 11, 2019 from the Internet:https://pubchem.ncbi.nlm.nih.gov/substance/319065898] entire doc.
Pubchem, Substrate Record for SID 262562287, Available Date: Dec. 10, 2015 [retrieved on Dec. 20, 2018 from the Internet:https://pubchem.ncbi.nlm.nih.gov/substance/262562287] entire doc.
Pubchem, Substrate Record for SID 120374932, Available Date: Apr. 5, 2011 [retrieved on Dec. 20, 2018 from the Internet:https://pubchem.ncbi.nlm.nih.gov/substance/120374932] entire doc.
Benilova et al., "The toxic Aβ oligomer and Alzheimer's disease: an emperor in need of clothes", Nat. Neurosci., 15(3):349-357 (2012).
Reiman, et al., "Alzheimer's Prevention Initiative: A Plan to Accelerate the Evalution of Presymptomatic . . . ", J. Alzheimers Dis. 26(Suppl 3): 321-329 (2011).
Dahlgren, et al., "Oligomeric and Fibrillar Species of Amyloid-β Peptides Differentially affect .. ", Journal of Biological Chemistry 285(9):6071-6079 (2010).
Hayden, et al., "Amyloid β-protein oligomers and Alzheimer's disease," Alzheimers Res Ther. 5(6):60 (2013).

(Continued)

*Primary Examiner* — Douglas M Willis
(74) *Attorney, Agent, or Firm* — Mintz, Levin, Cohn, Ferris, Glovsky and Popeo, P.C.

(57) ABSTRACT

The present disclosure provides small molecule drugs and pharmaceutical compositions for the treatment and prevention of diseases related to the formation of Aβ42 oligomers in a subject. It further provides a method of reducing formation of or disrupting Aβ42 oligomers in a subject, the method comprising the step of administering to the subject in need thereof a therapeutically effective amount of a pharmaceutical composition. One such compound is a compound of formula 120:

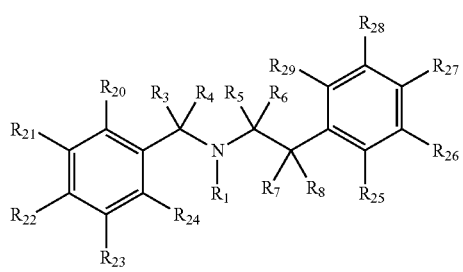

6 Claims, 56 Drawing Sheets

(56) References Cited

OTHER PUBLICATIONS

Meng, et al., "The Flavanol (-)-Epigallocatechin 3-Gallate Inhibits Amyloid Formation by Islet . . . ", Biochemistry 49(37):8127-8133 (2010).

Wu, et al., "Fibrillar Oligomers Nucleate the Oligomerization of Monomeric Amyloid β but . . . ", Journal of Biological Chemistry 285(9):6071-6079 (2010).

Ladiwala, et al., "Rational Design of Potent Domain Antibody Inhibitors of Amyloid Fibril Assembly," PNAS 109(1):84-89 (2012).

Guo et al., "Acidic ionic liquid [NMP]H"2po'4 as dual solvent-catalyst for synthesis . . . " Tetrahedron (Oct. 16, 2010) pp. 8300-8303, vol. 66, No. 42, Elsevier Sience Publishers.

Sakura et al., "Catalytic hydrogenolyses of Benzylidene Compounds Bound to Two Oxygens.." Chemical and Pharmaceutical Bulletin (Jun. 1, 1972) pp. 1156-1163, vol. 20, No. 6.

Zhou et al., "Ester Hydrolysis by a Cyclodextrin Dimer Catalyst with a . . . " Chemistry—A European Journal (Aug. 18, 2008) pp. 7193-7201, vol. 14, No. 24.

Reyes et al., "Convenient route for the preparation of C2-symmetric . . . " Chirality (Jan. 19, 1999) pp. 95-99, vol. 10, No. 1-2.

Yuan et al., "Enantioselective Synthesis of Chiral 1, 2-Amino Alcohols . . . " Synthesis (Aug. 6, 2014) pp. 2910-2916, vol. 46, No. 21.

Yan et al., "Benzylamines via Iron-Catalysed Direct Amination of Benzyl Alcohols" ACS Catalysis (Dec. 3, 2015) pp. 381-388, vol. 6.

Proshin et al., "Tetrasubstituted thiuronium salts as multitarget . . . " Russian Chemical Bulletin (Sep. 27, 2016) pp. 2189-2194, vol. 64, No. 9, Springer New York LLC.

Petersen, et al., "Convergent 18F-labeling and evaluation of n-benzyl- . . . " Bioorganic & Medicinal Chem (Aug. 29, 2016) pp. 5353-5356, Elsevier Science Pub.

* cited by examiner

DAEFRHDSGY[10]EVHHQKLVFF[20]AEDVGSNKGA[30]IIGLMVGGVV[40]IA[42]

*Negative residues in cyan, positive residues in red;
native solution charge state of -3* m= mass
z= charge
n= oligomer
order z/n=
charge state

Figure 8

| # | structure | $MolName | EC50 |
|---|---|---|---|
| 1 | 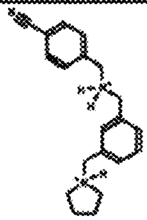 | AC0107 | 0.45 |
| 2 | 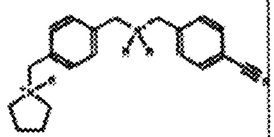 | AC0105 | 0.51 |
| 3 | 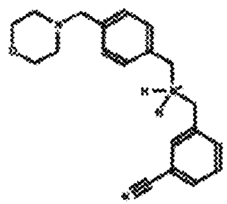 | AC0104 | 0.7 |
| 4 | 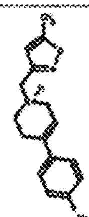 | AC0106 | 1 |
| 5 | 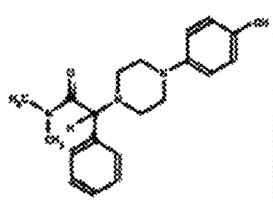 | AC0103 | 1.3 |
| 6 | 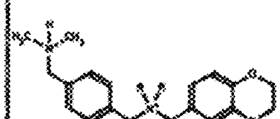 | AC0102 | 3.5 |
| 7 | 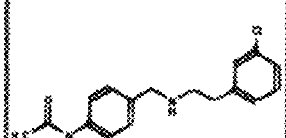 | AC0101 | 3.9 |

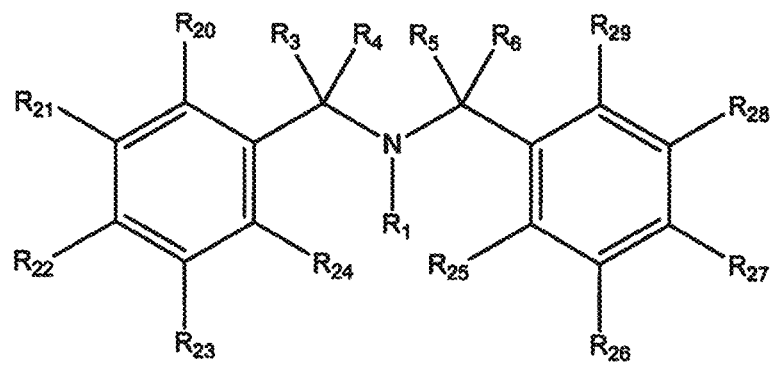
100
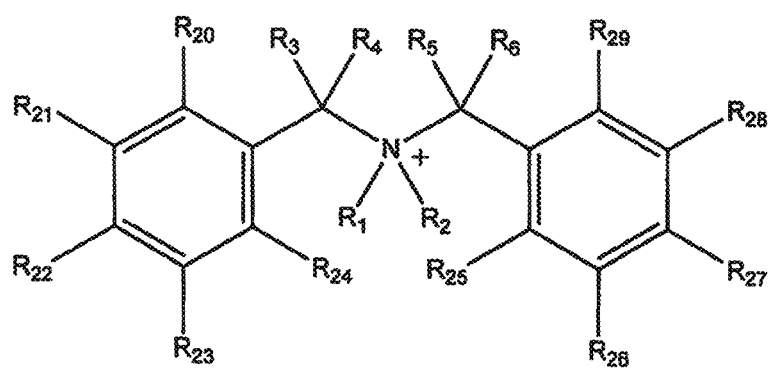
102
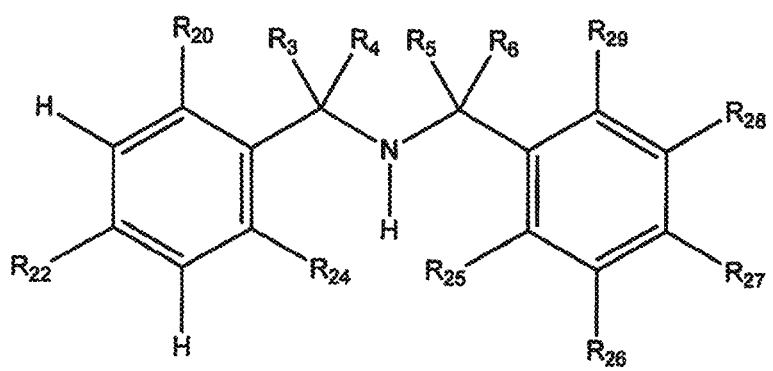
104
FIG. 9

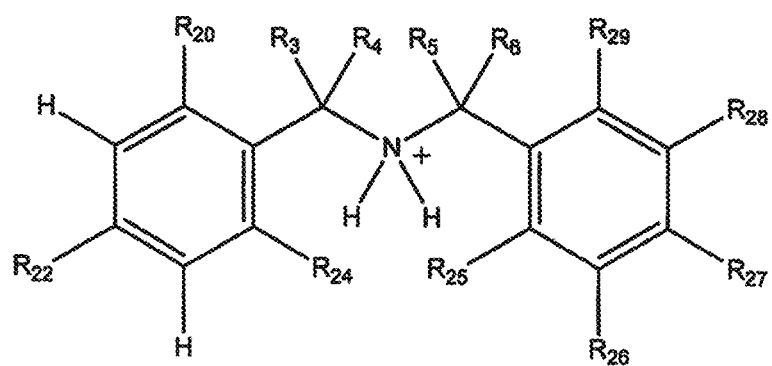
106
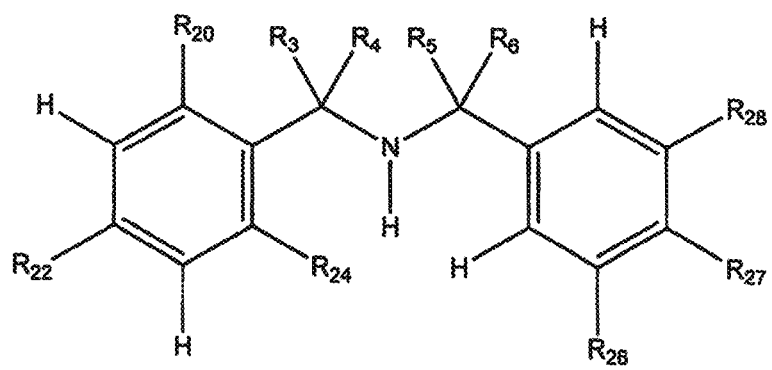
108
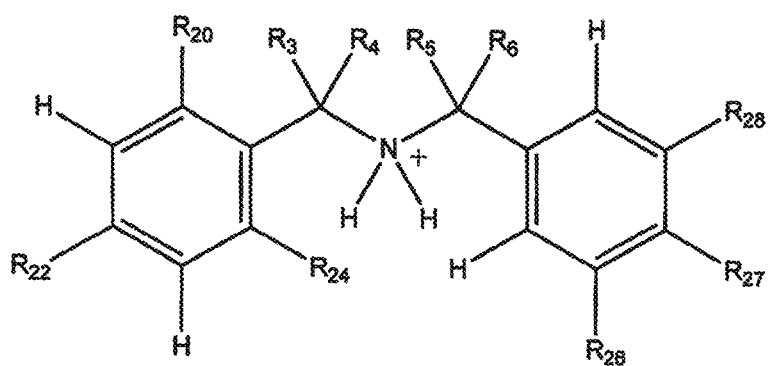
110
FIG. 10

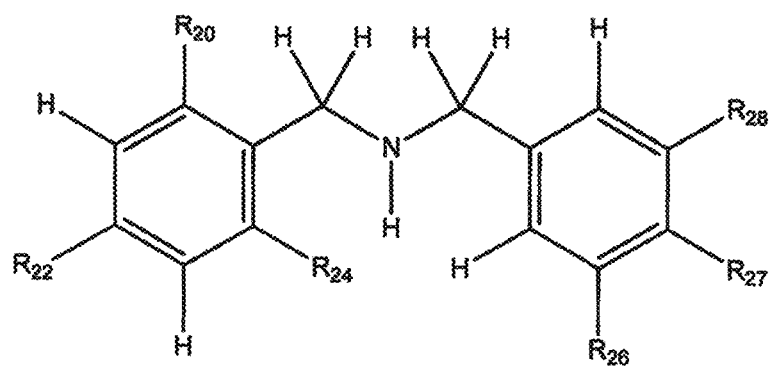
112
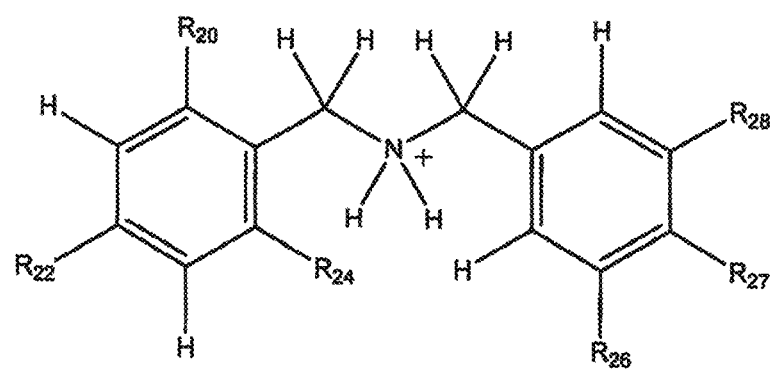
114
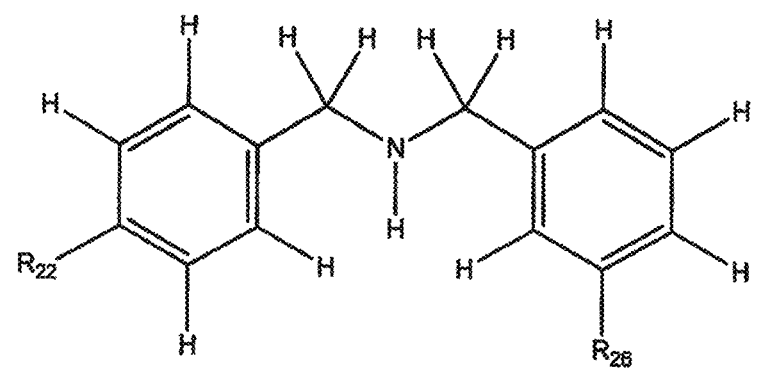
116
FIG. 11

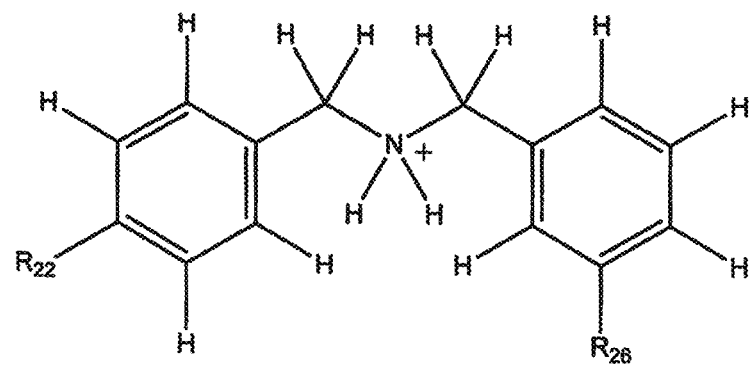
118
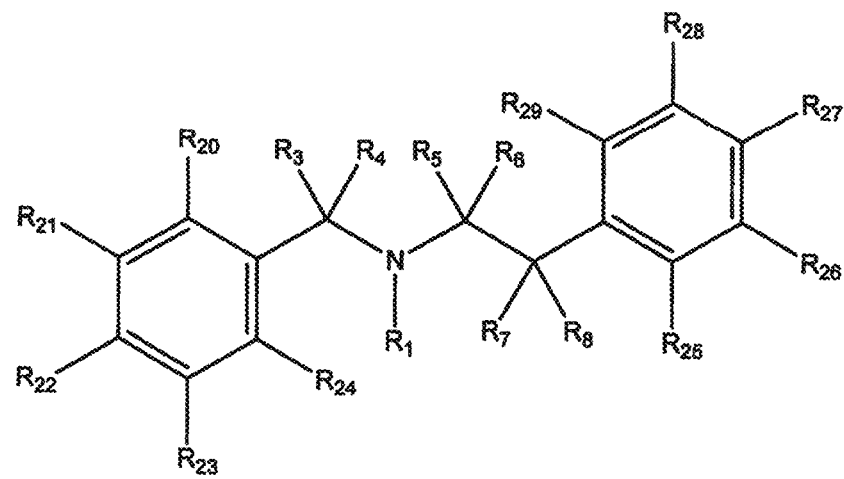
120
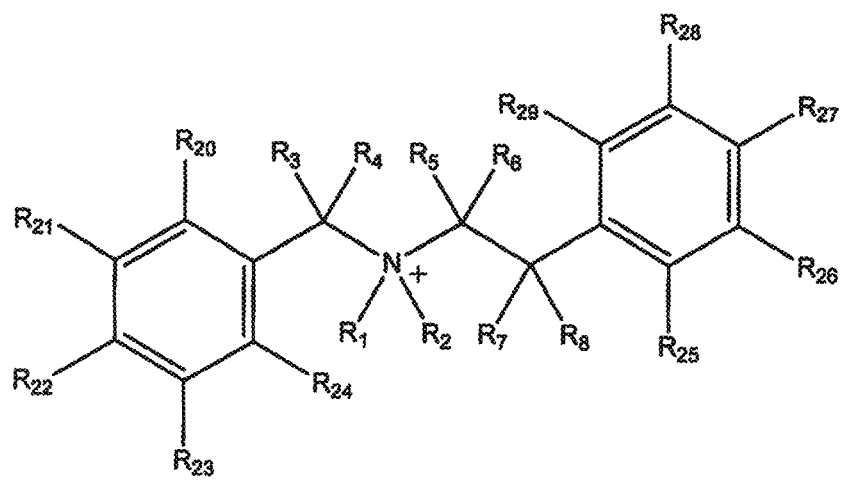
122
FIG. 12

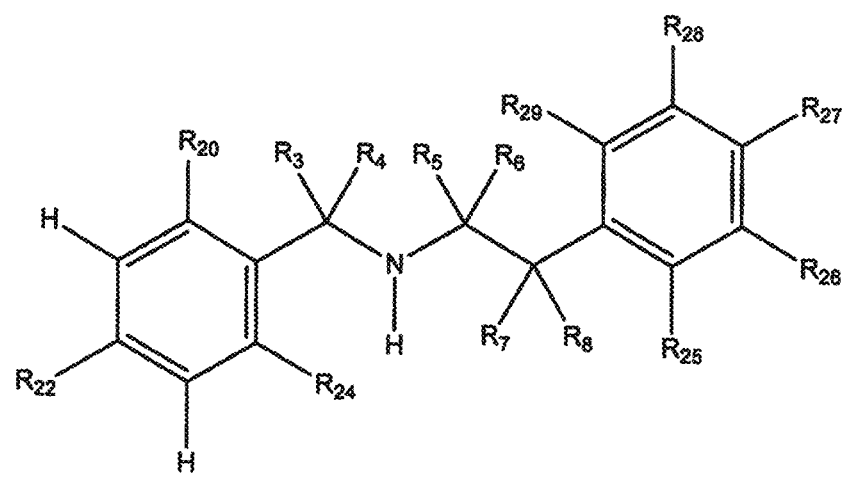
124
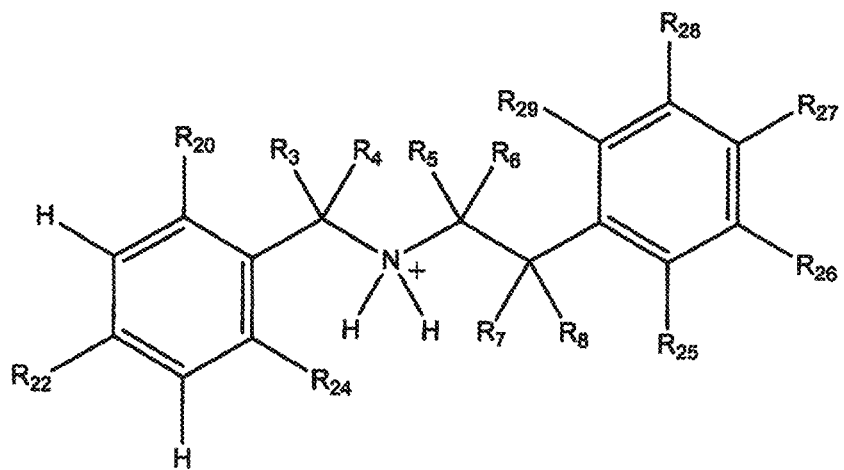
126
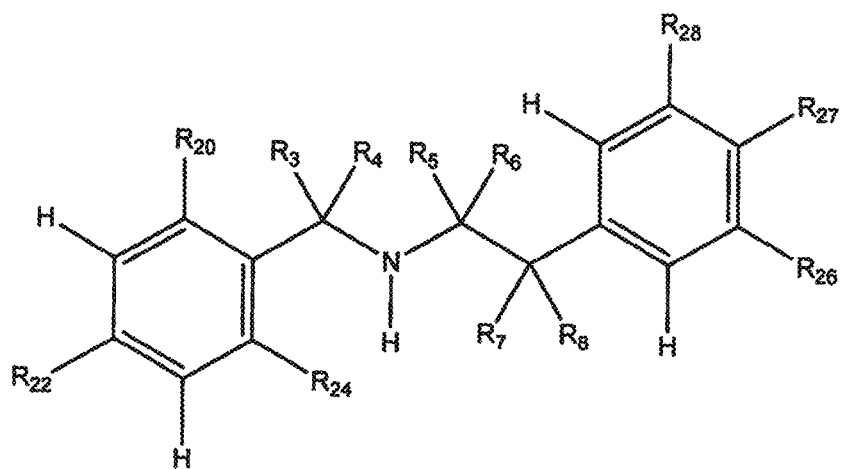
128
FIG. 13

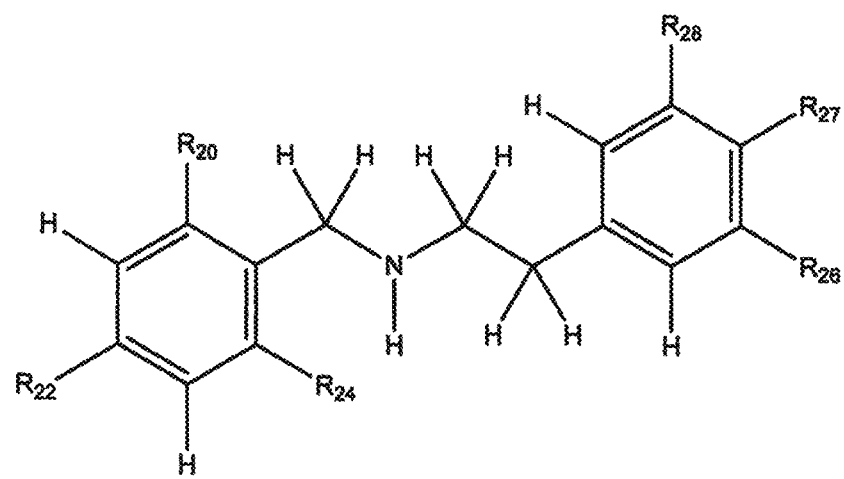
130
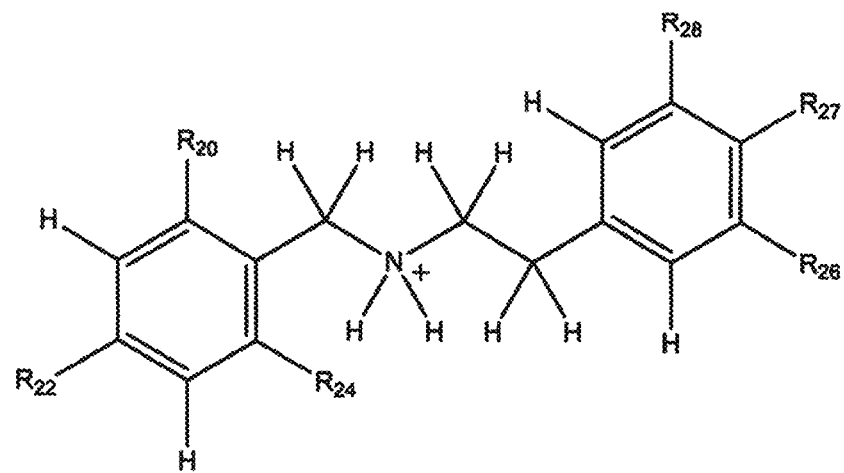
132
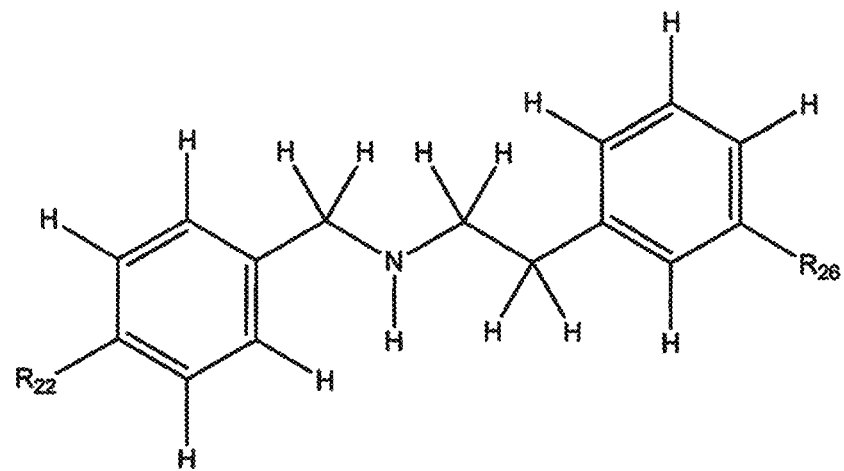
134
FIG. 14

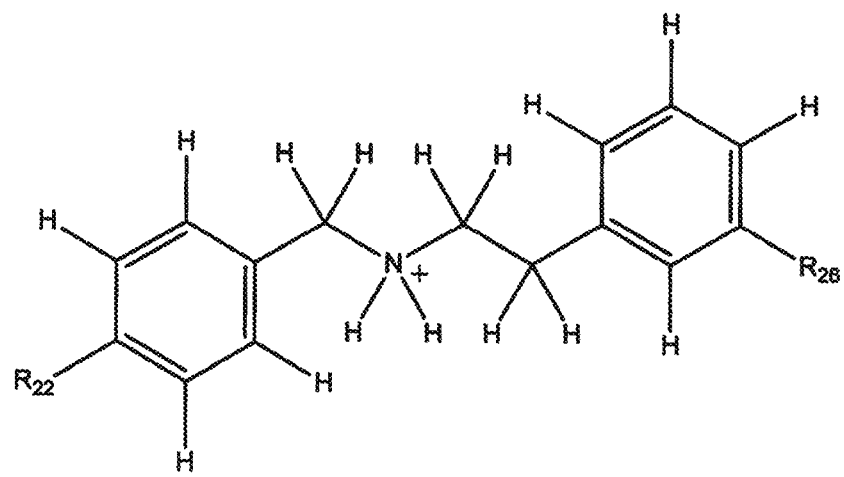
136
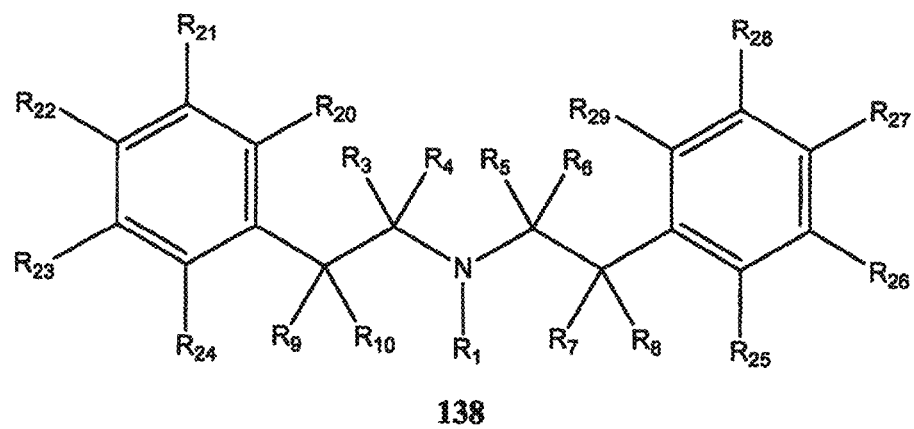
138
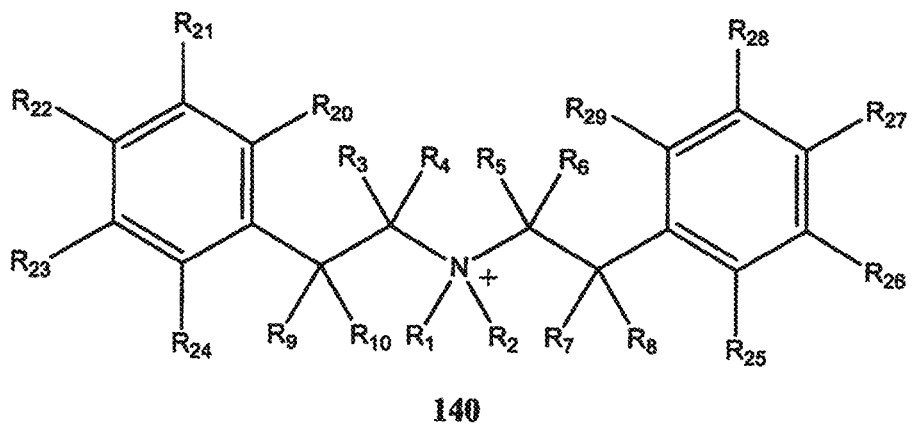
140
FIG. 15

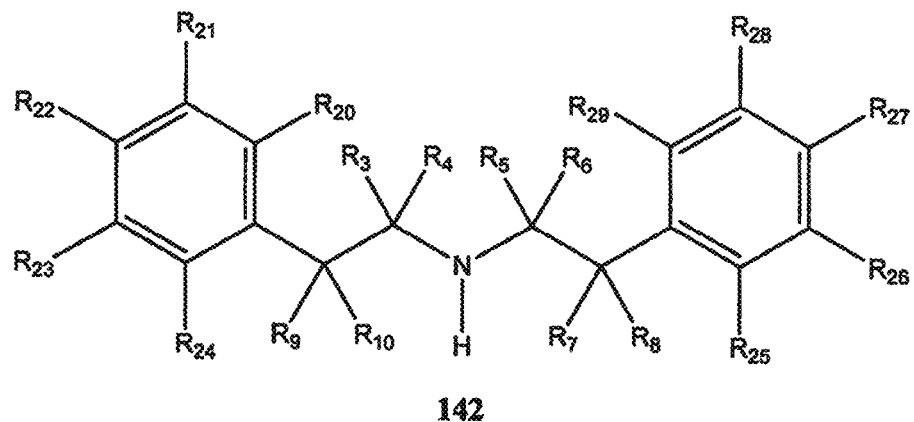
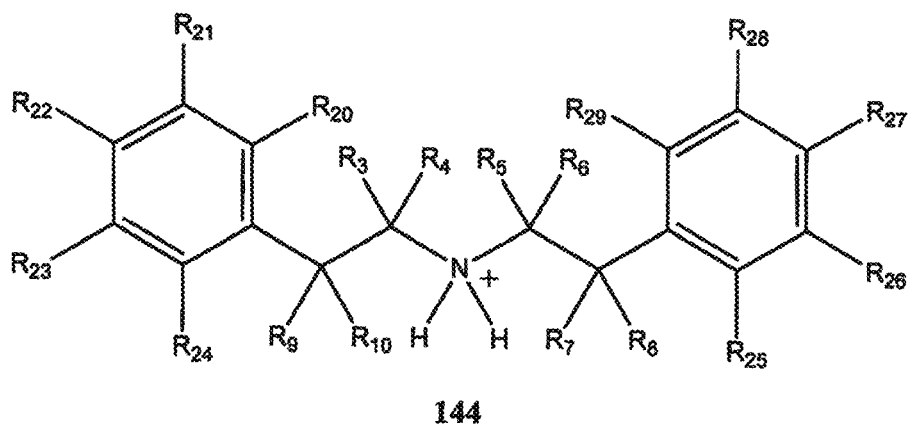
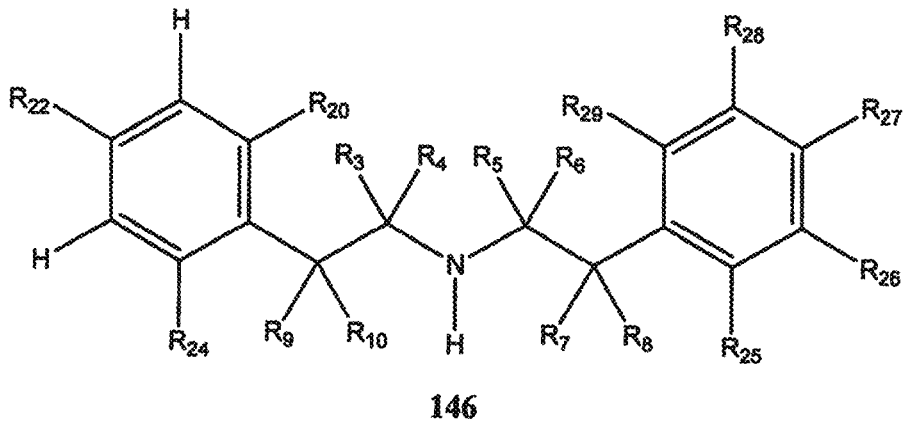
FIG. 16

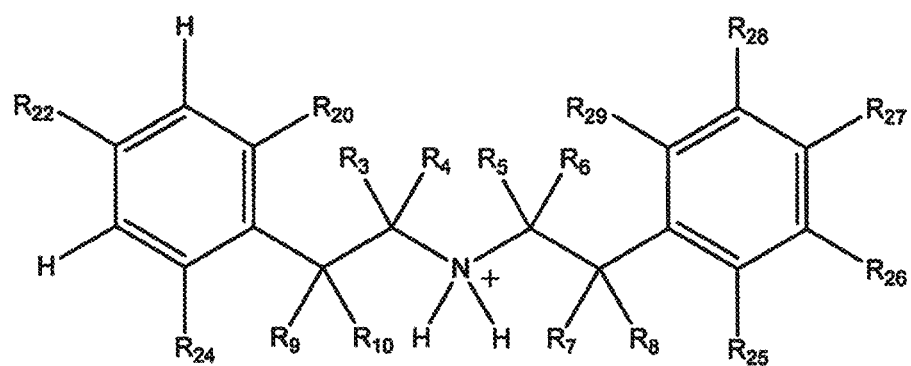
148
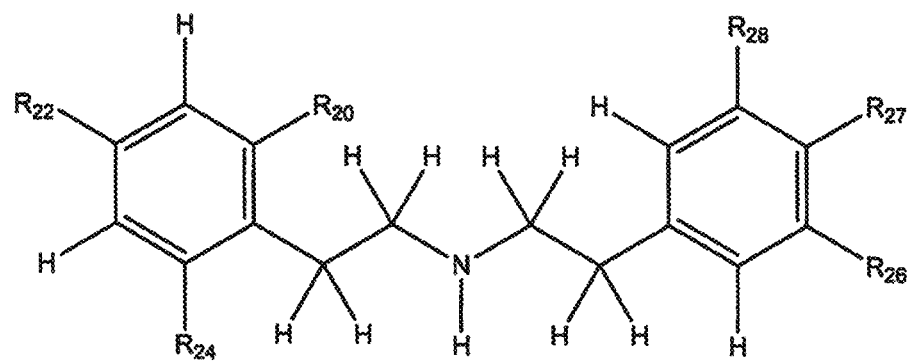
150
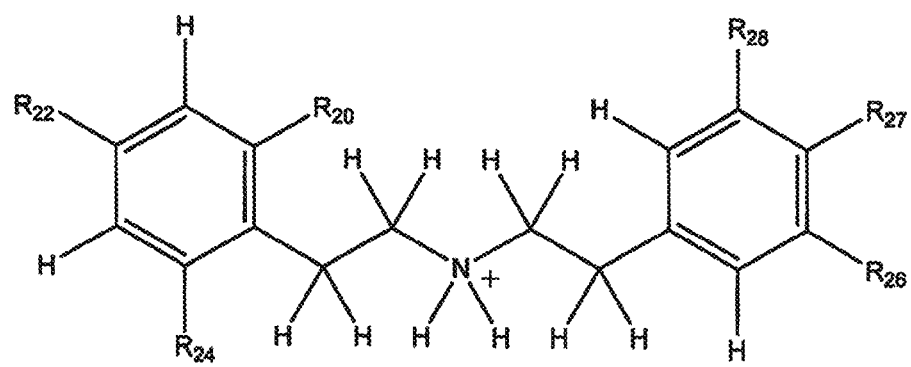
152
FIG. 17

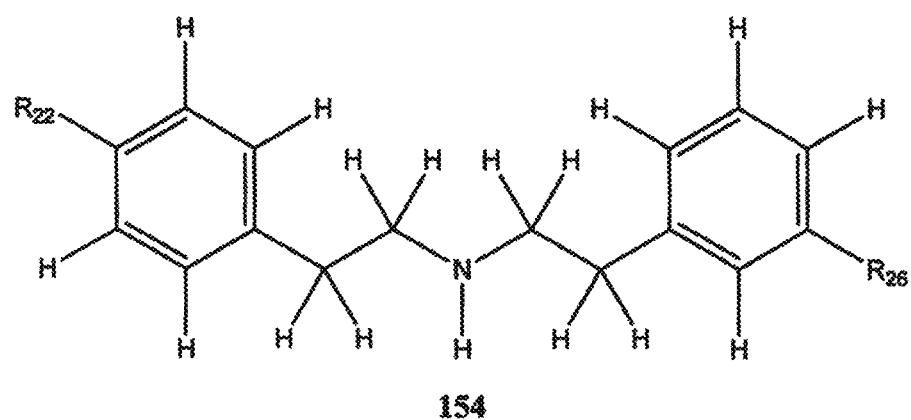
154
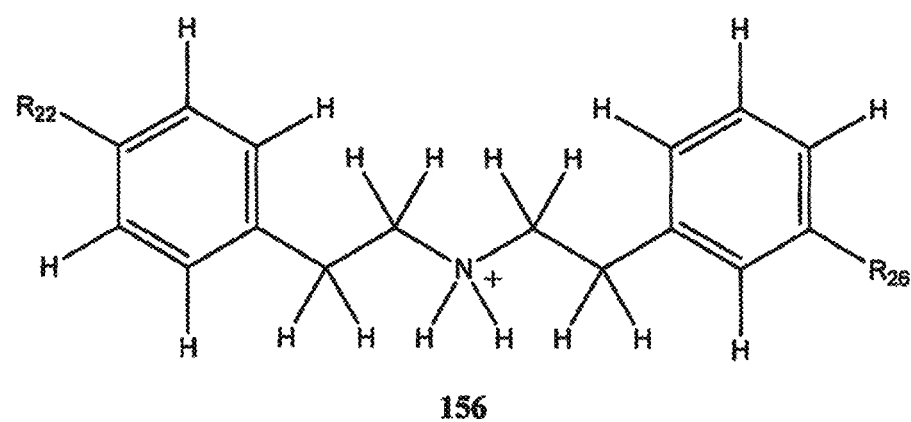
156
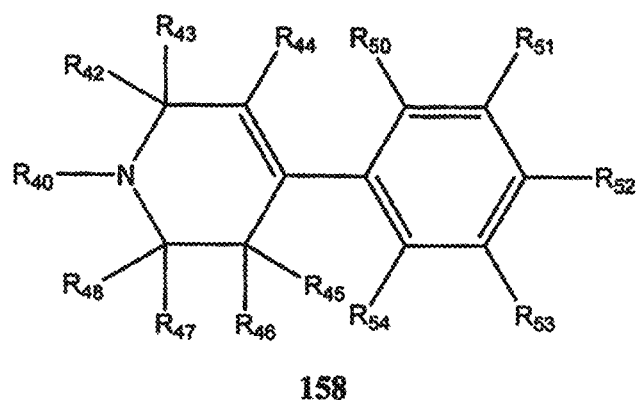
158
FIG. 18

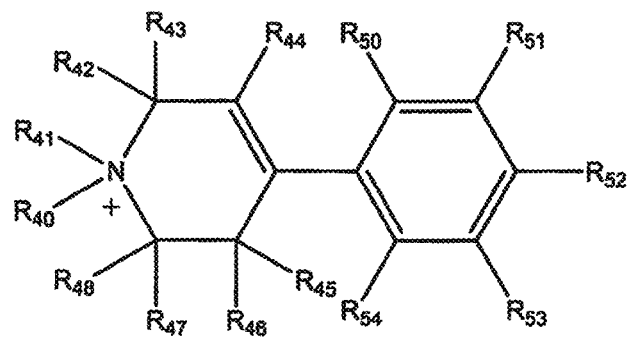
160
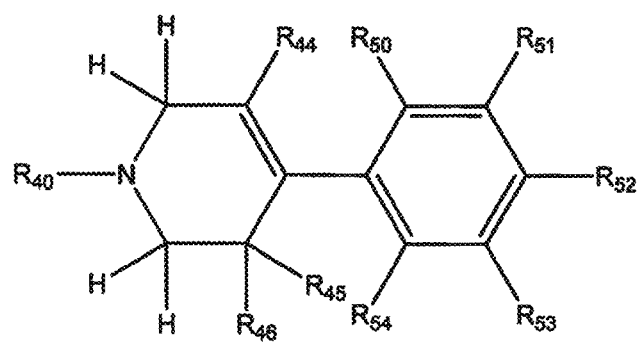
162
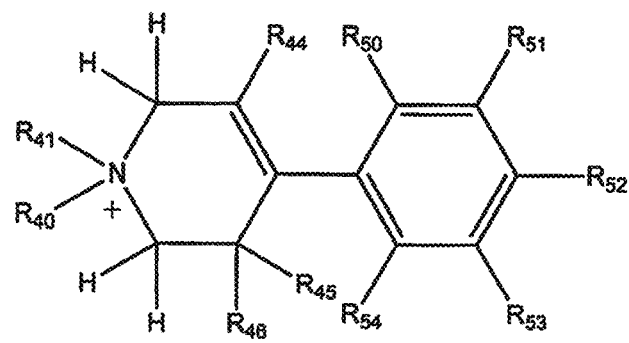
164
FIG. 19

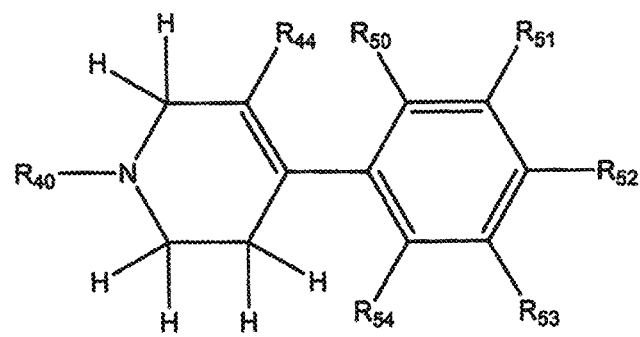
166
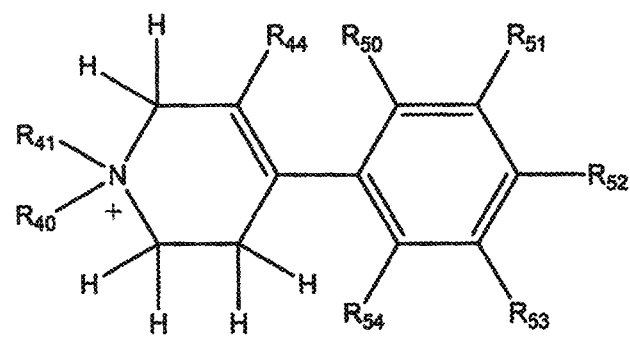
168
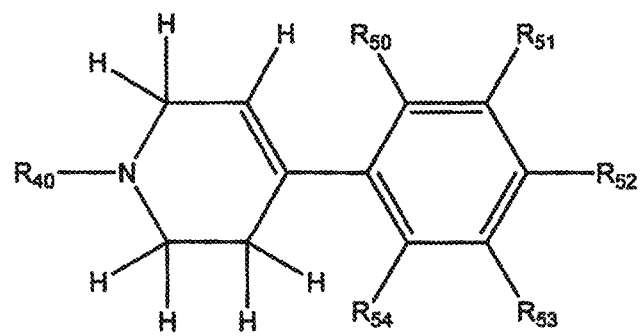
170
FIG. 20

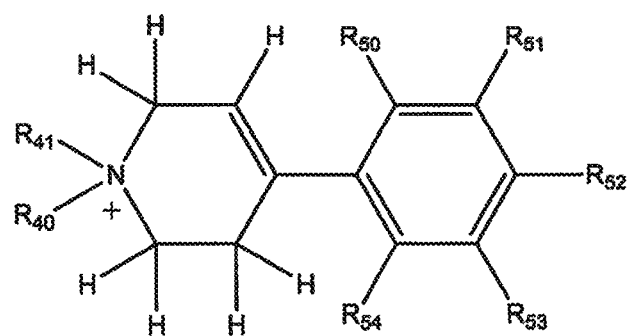
172
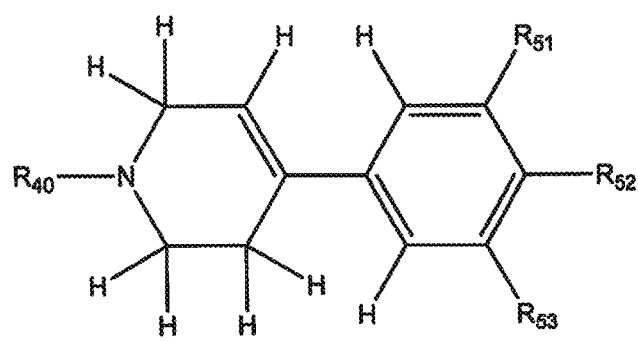
174
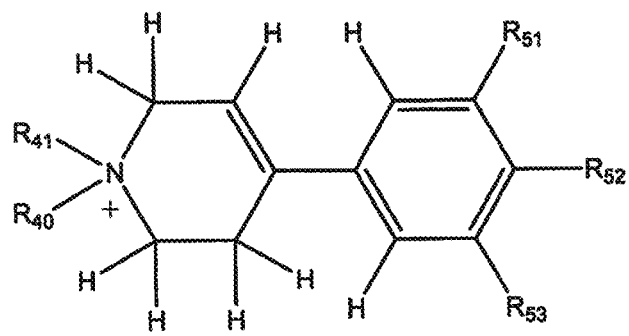
176
FIG. 21

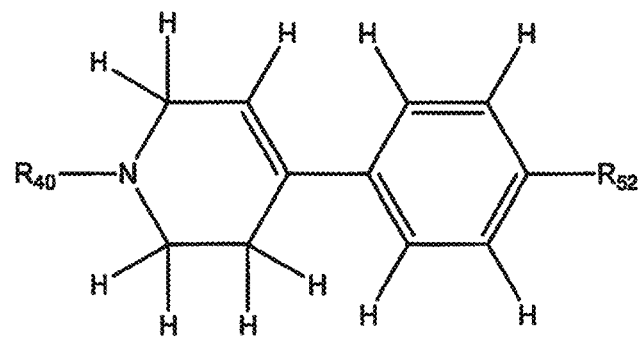
178
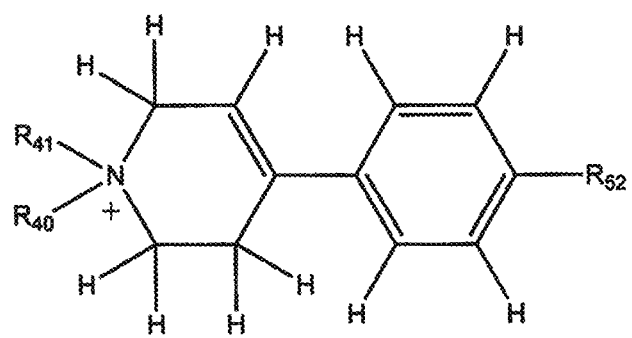
180
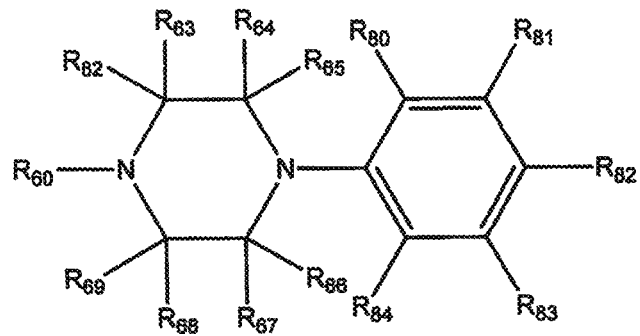
182
FIG. 22

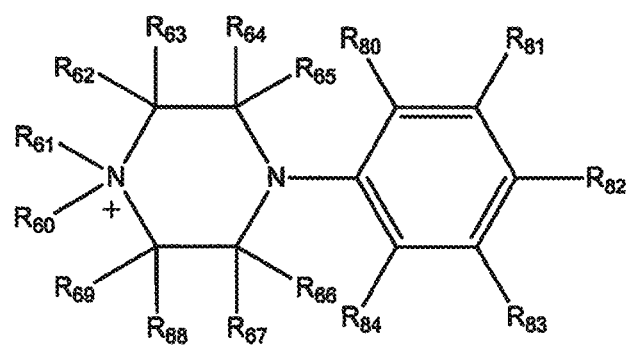
184
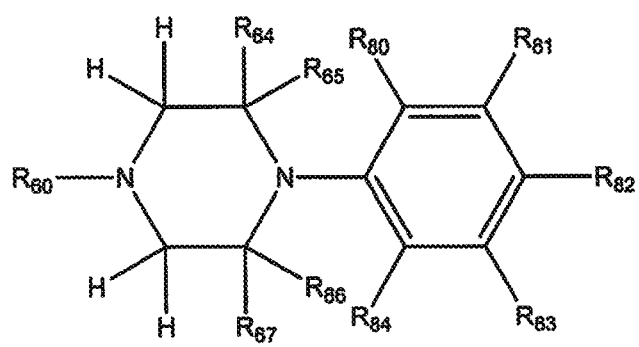
186
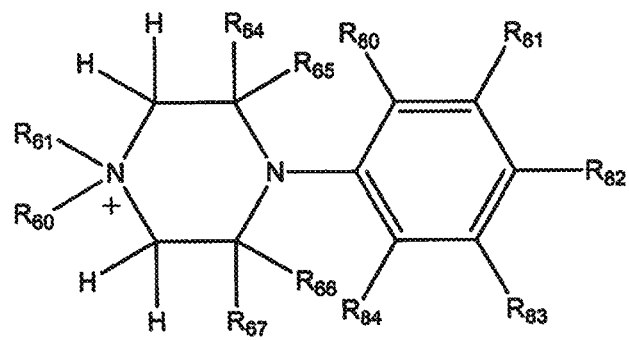
188
FIG. 23

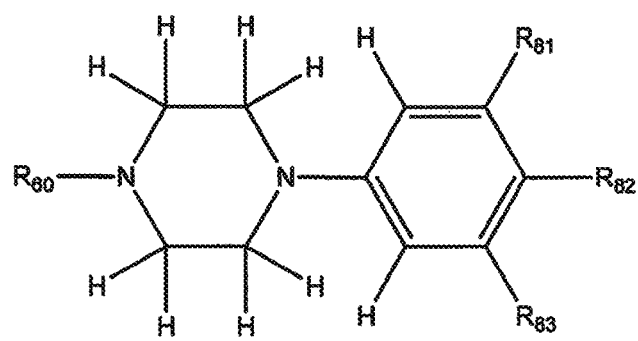
190
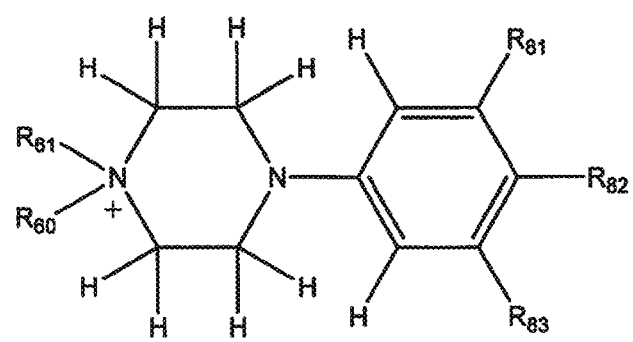
192
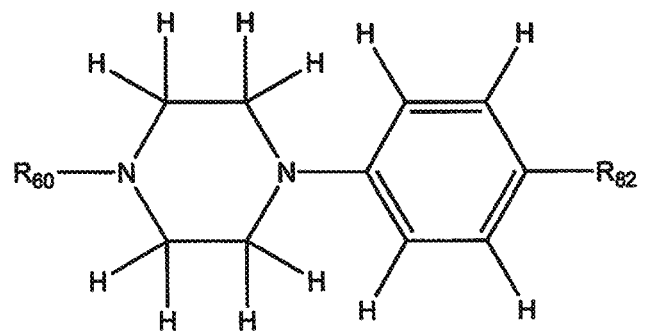
194
FIG. 24

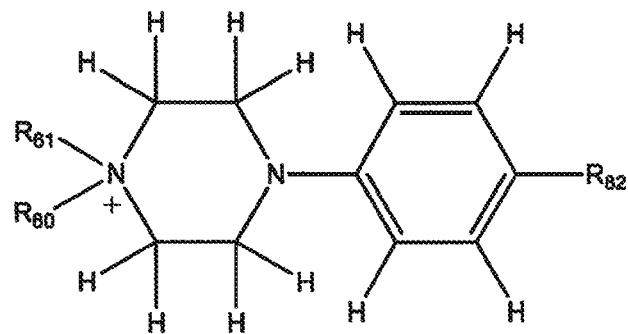
196
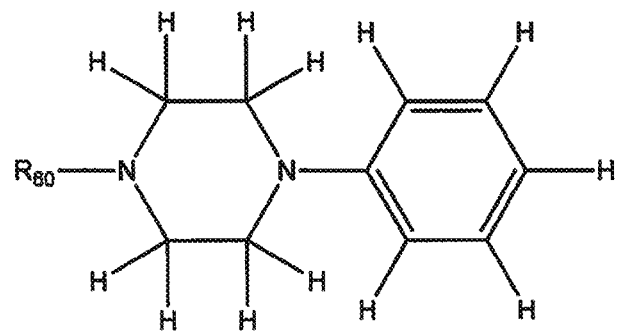
198
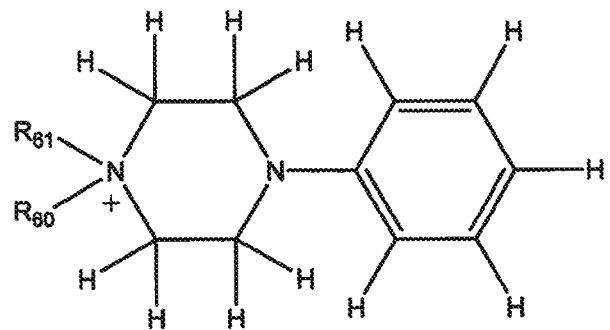
200
FIG. 25

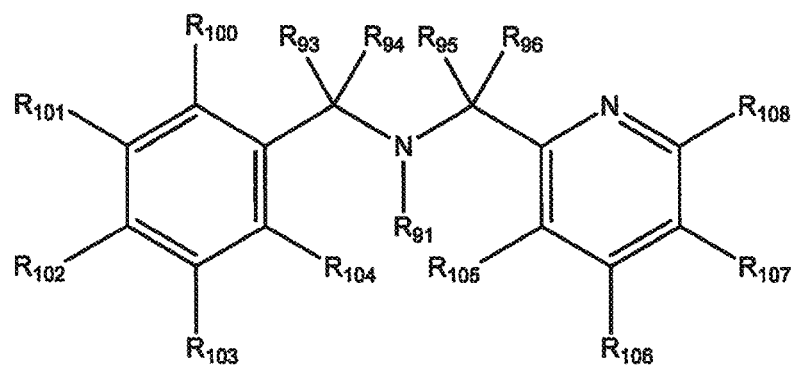
202
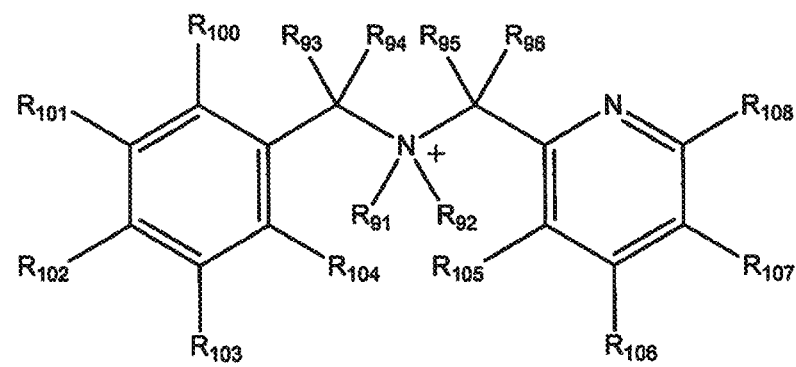
204
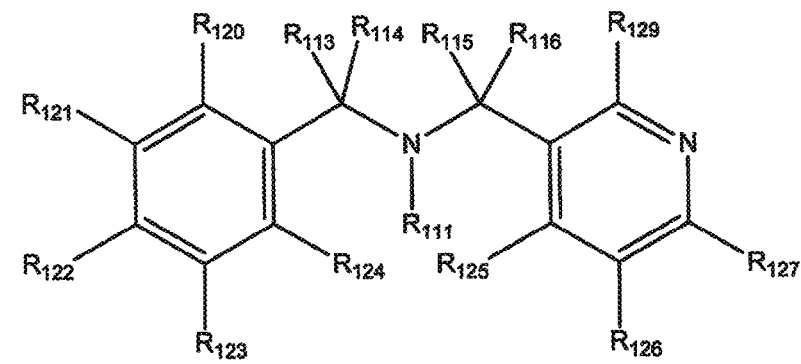
206
FIG. 26

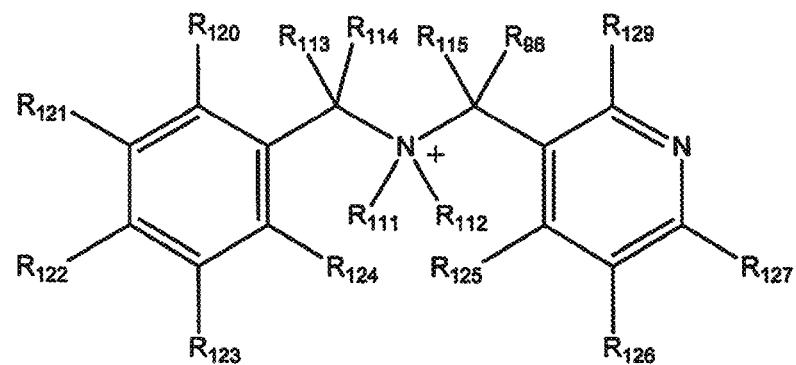
208
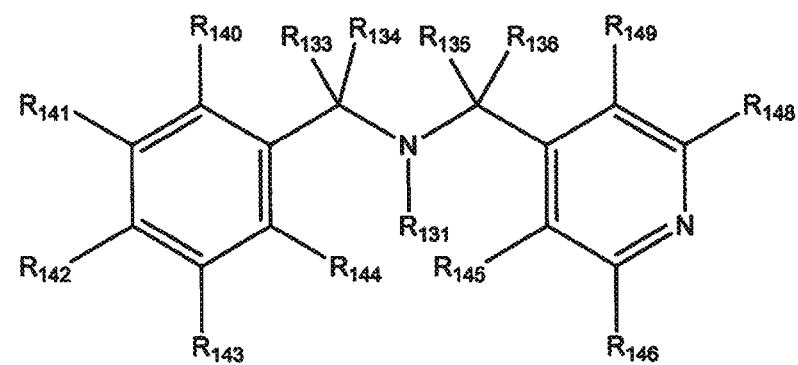
210
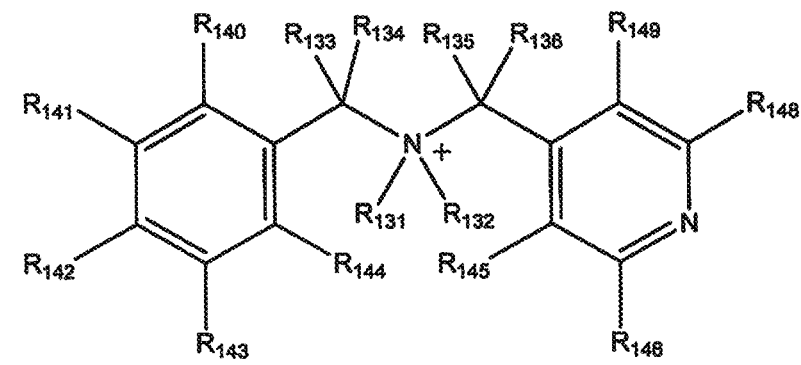
212
FIG. 27

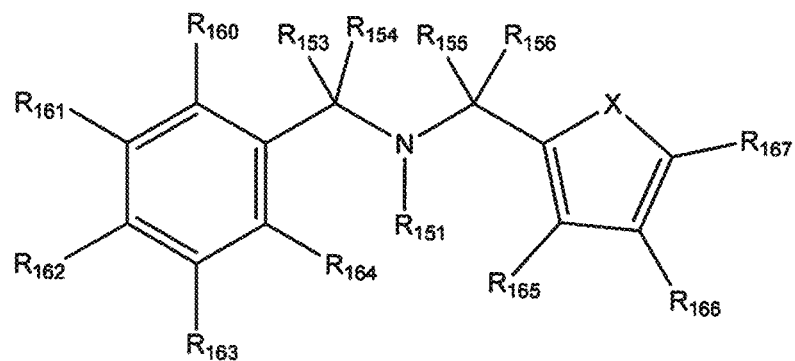
214
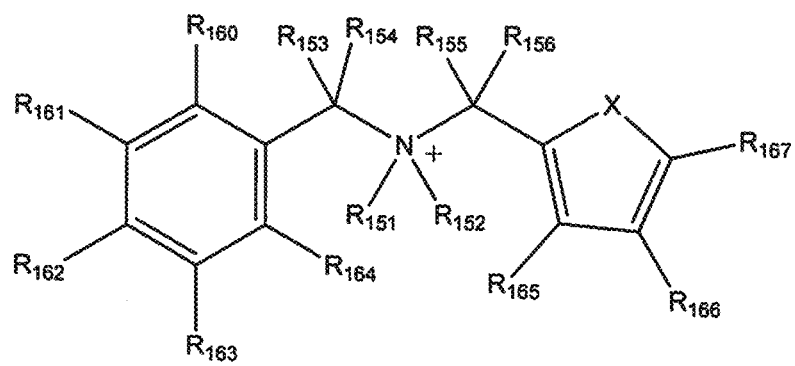
216
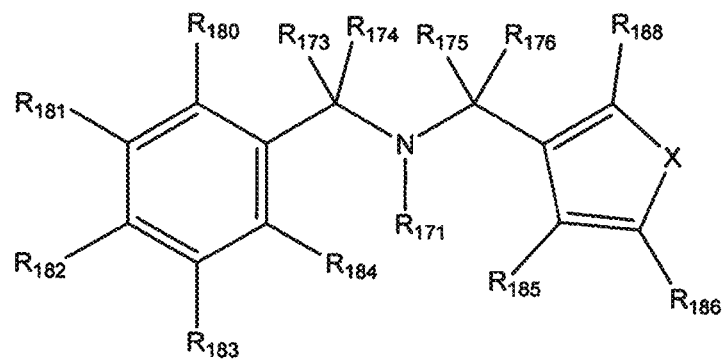
218
FIG. 28

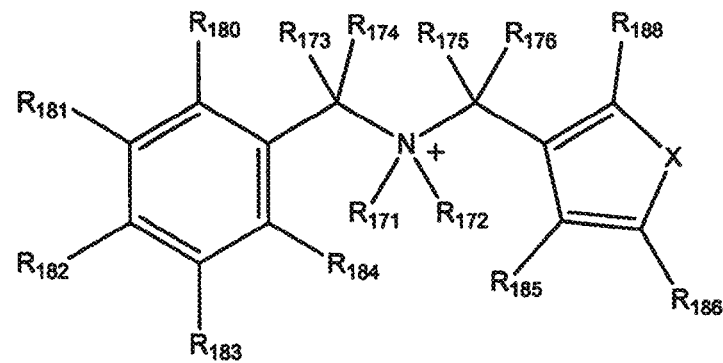
220
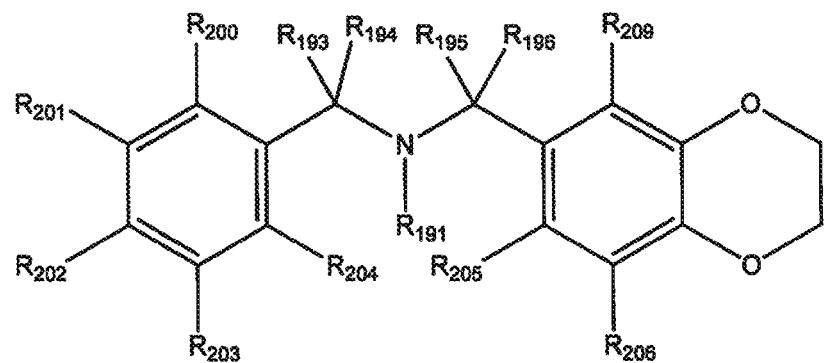
222
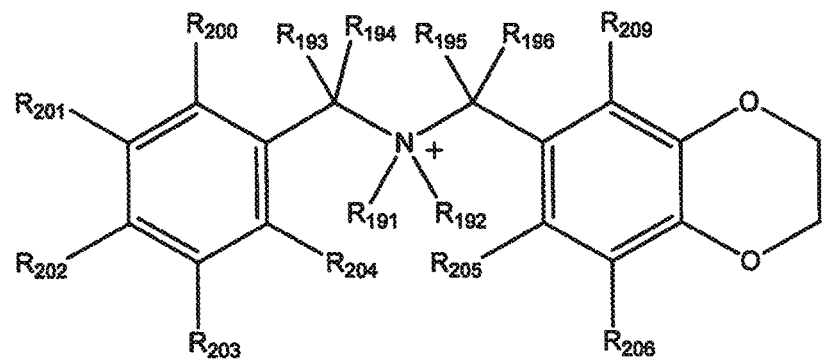
224
FIG. 29

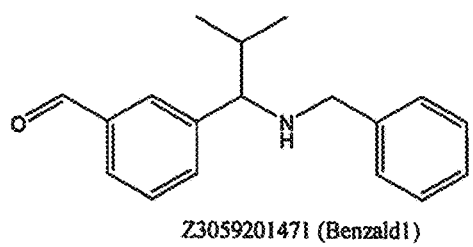
Z3059201471 (Benzald1)
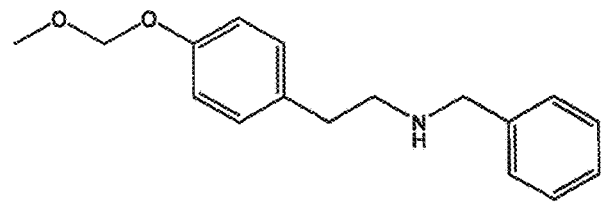
Z3059201528
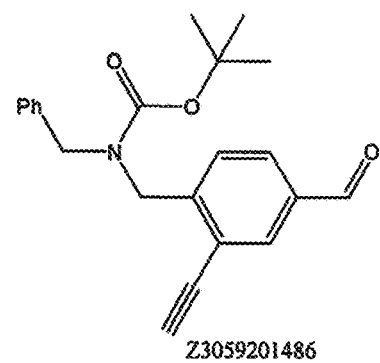
Z3059201486
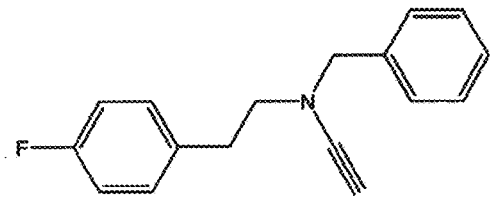
Z3059201535
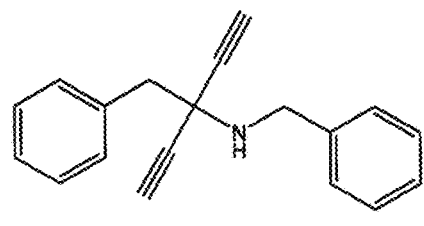
Z3059201492
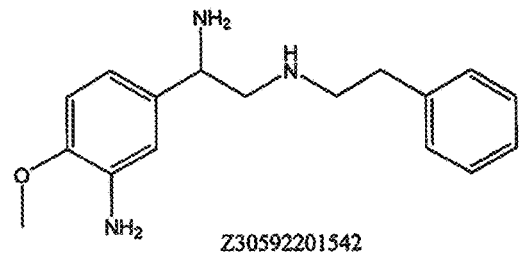
Z30592201542
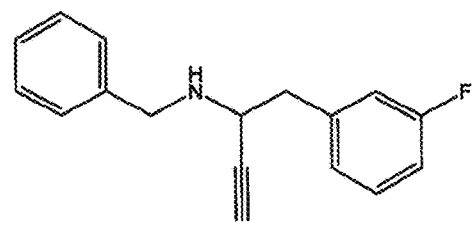
Z3059201512 (Fluorophenyl)
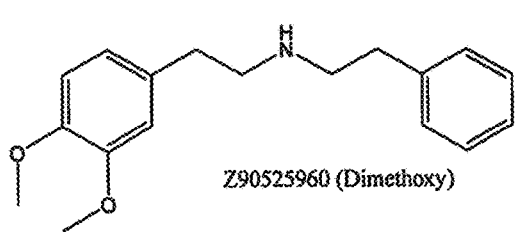
Z90525960 (Dimethoxy)
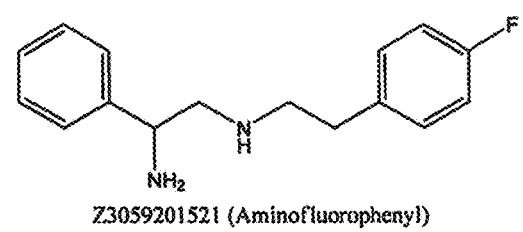
Z3059201521 (Aminofluorophenyl)
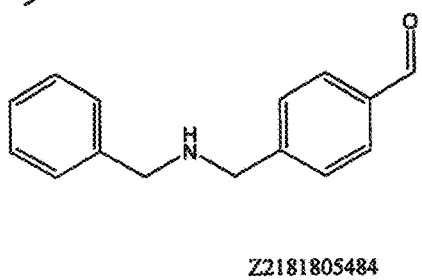
Z2181805484
FIG. 30

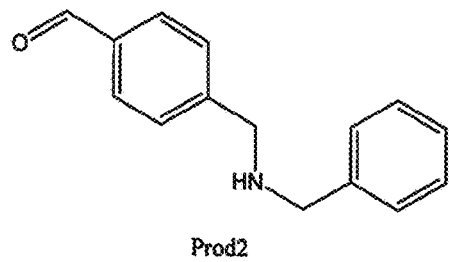
Prod2
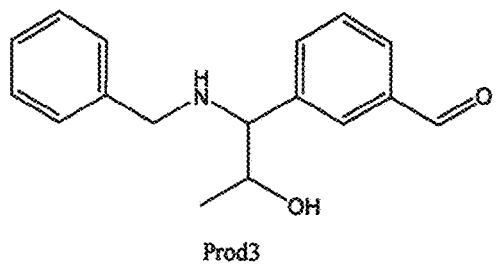
Prod3
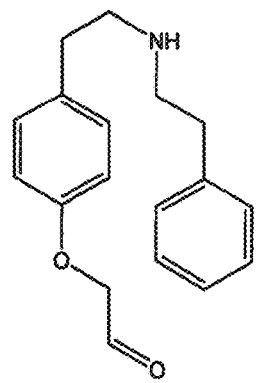
Prod1
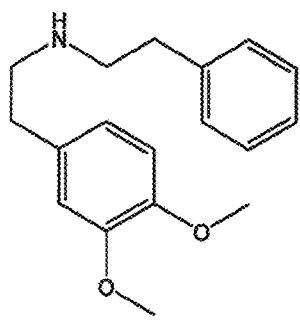
Prod46
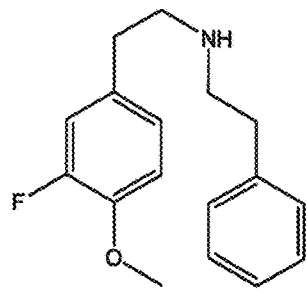
Prod79
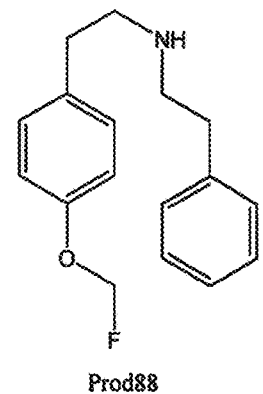
Prod88
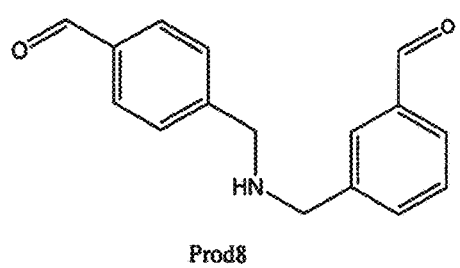
Prod8
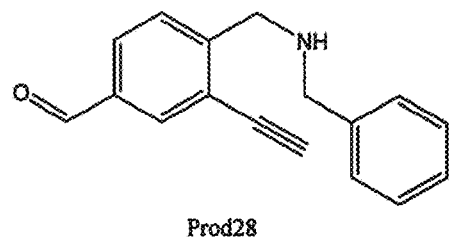
Prod28
FIG. 31

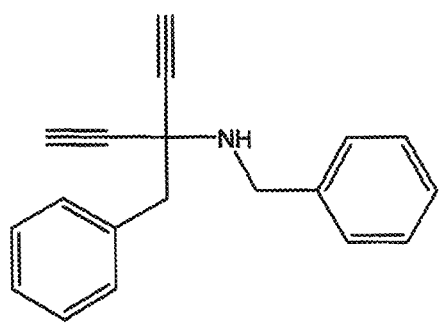
Prod42
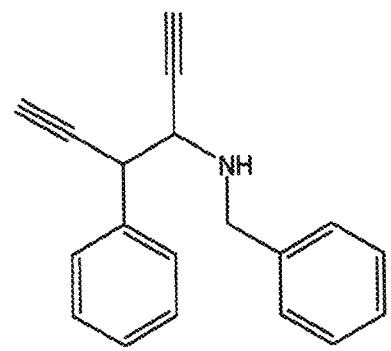
Prod43
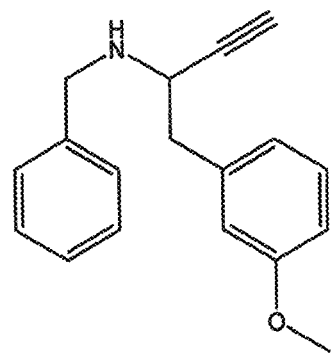
Prod51
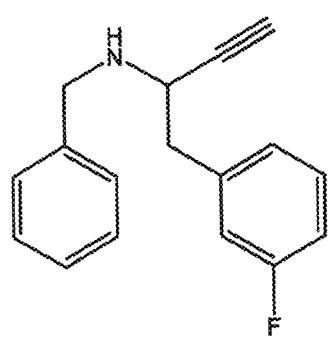
Prod84
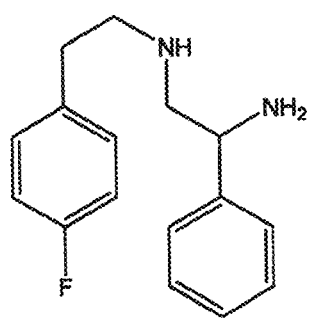
Prod59
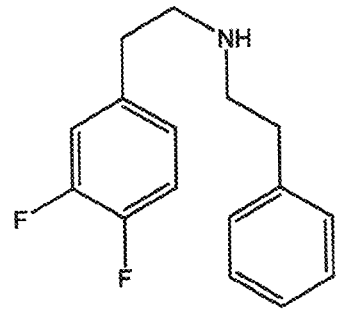
Prod72
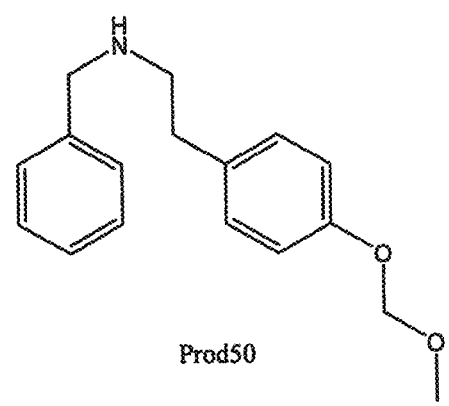
Prod50
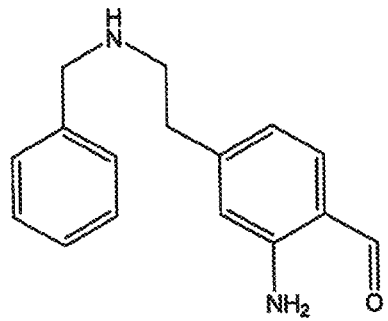
Prod7
FIG. 32

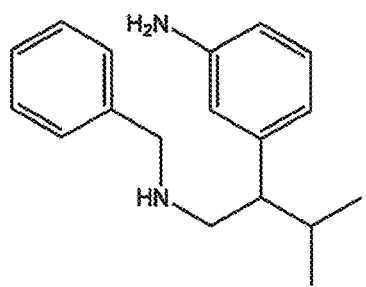
Prod35
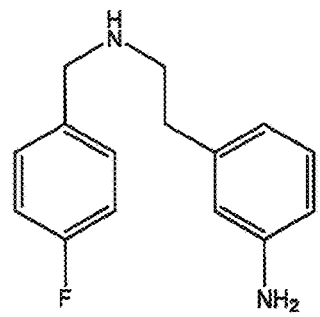
Prod86
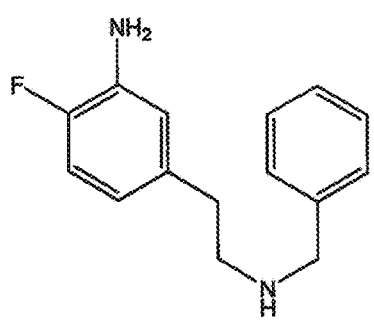
Prod91
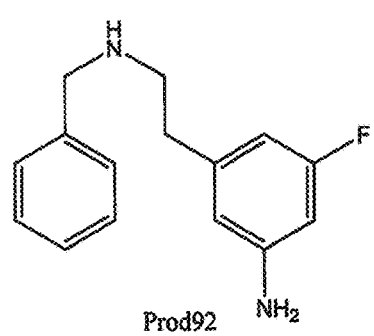
Prod92
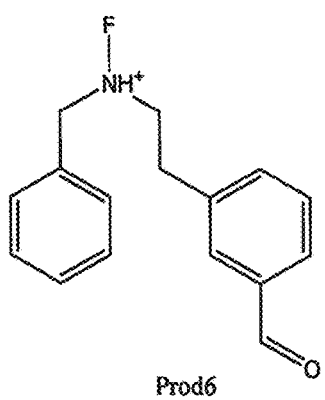
Prod6
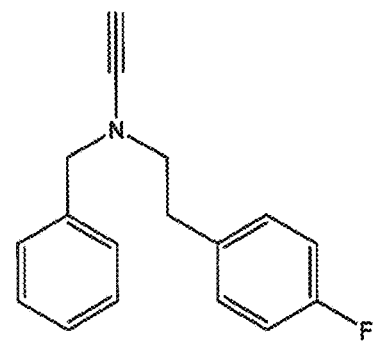
Prod32
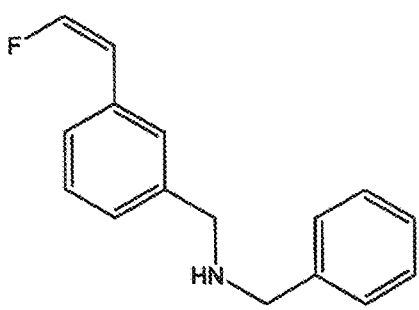
Prod96
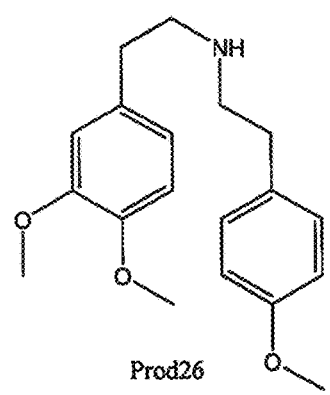
Prod26
FIG. 33

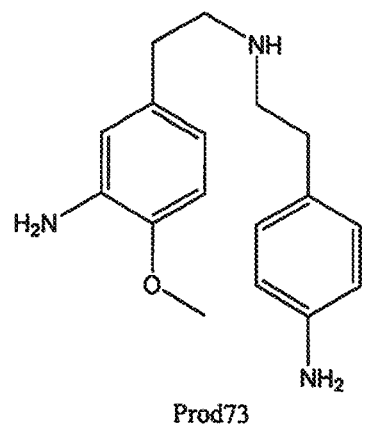
Prod73
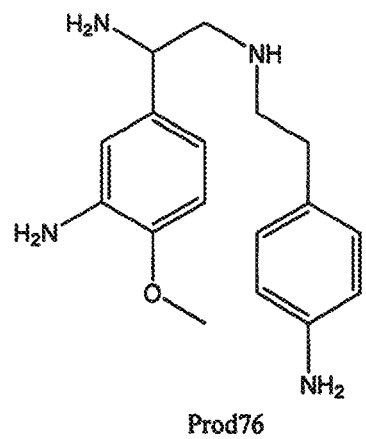
Prod76
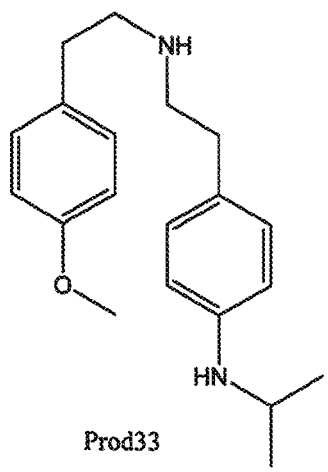
Prod33
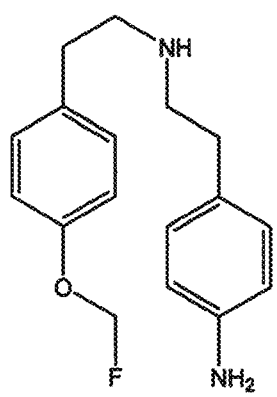
Prod87
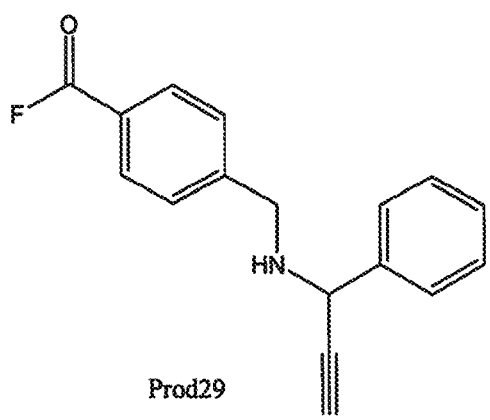
Prod29
FIG. 34

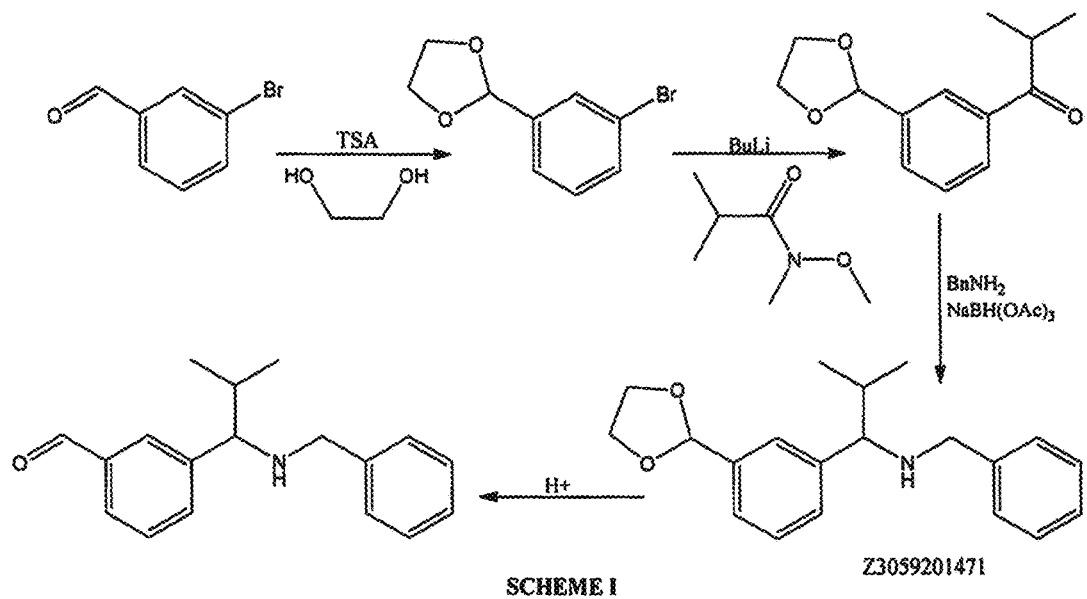
SCHEME I
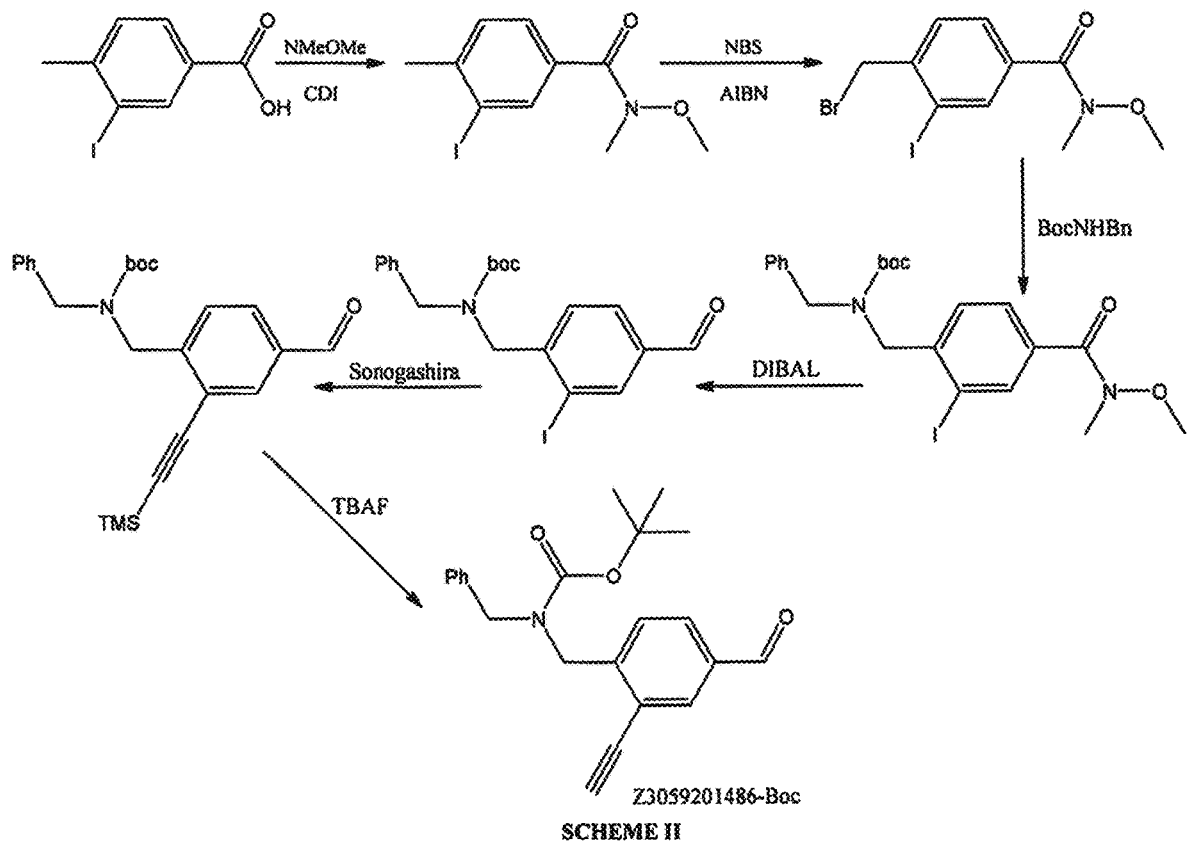
SCHEME II
FIG. 35

SCHEME III

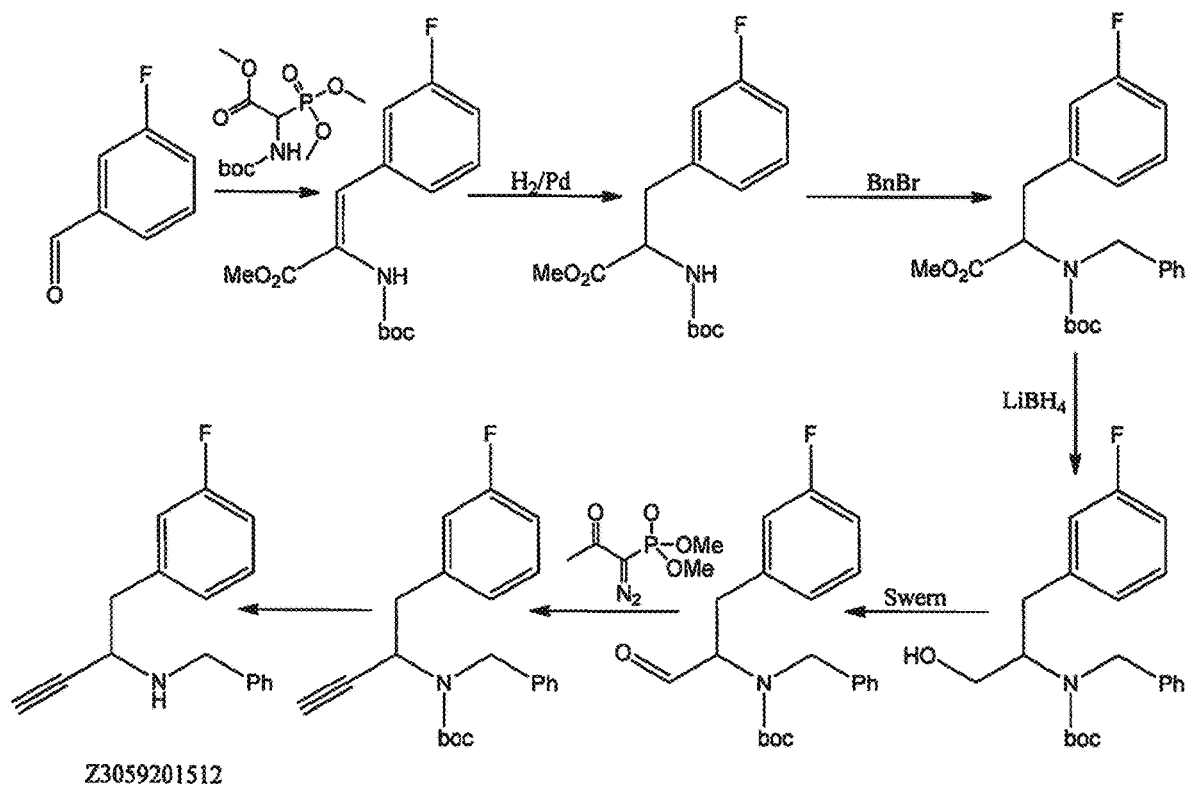
SCHEME 4
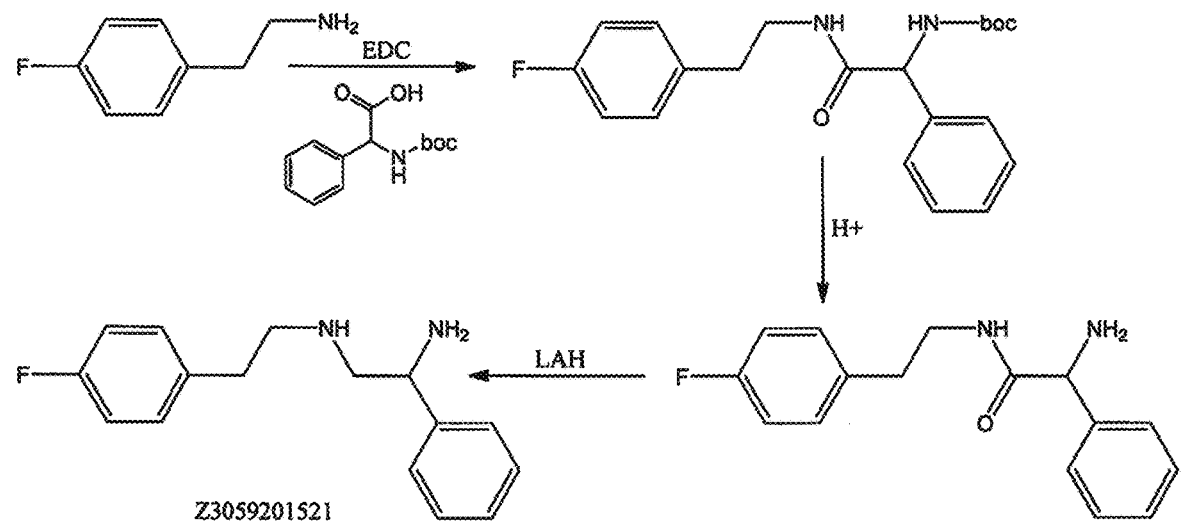
SCHEME 5
FIG. 37

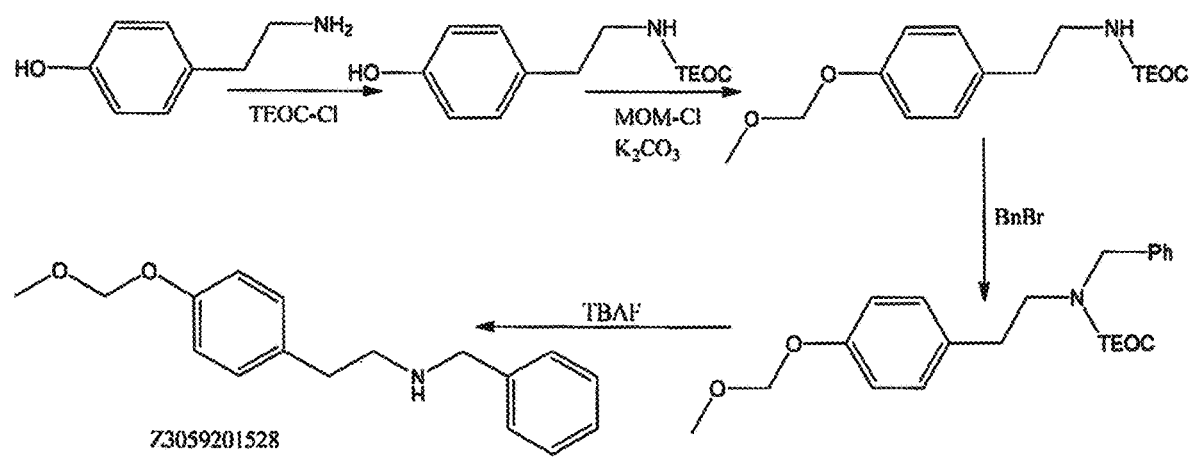
SCHEME 6
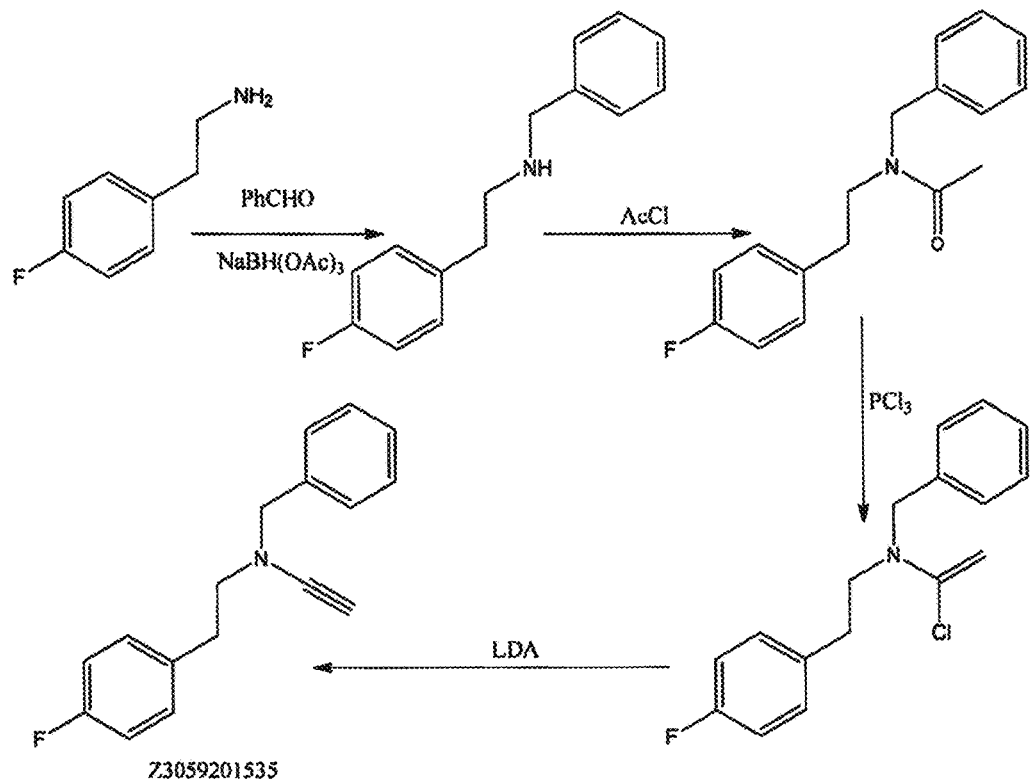
SCHEME 7
FIG. 38

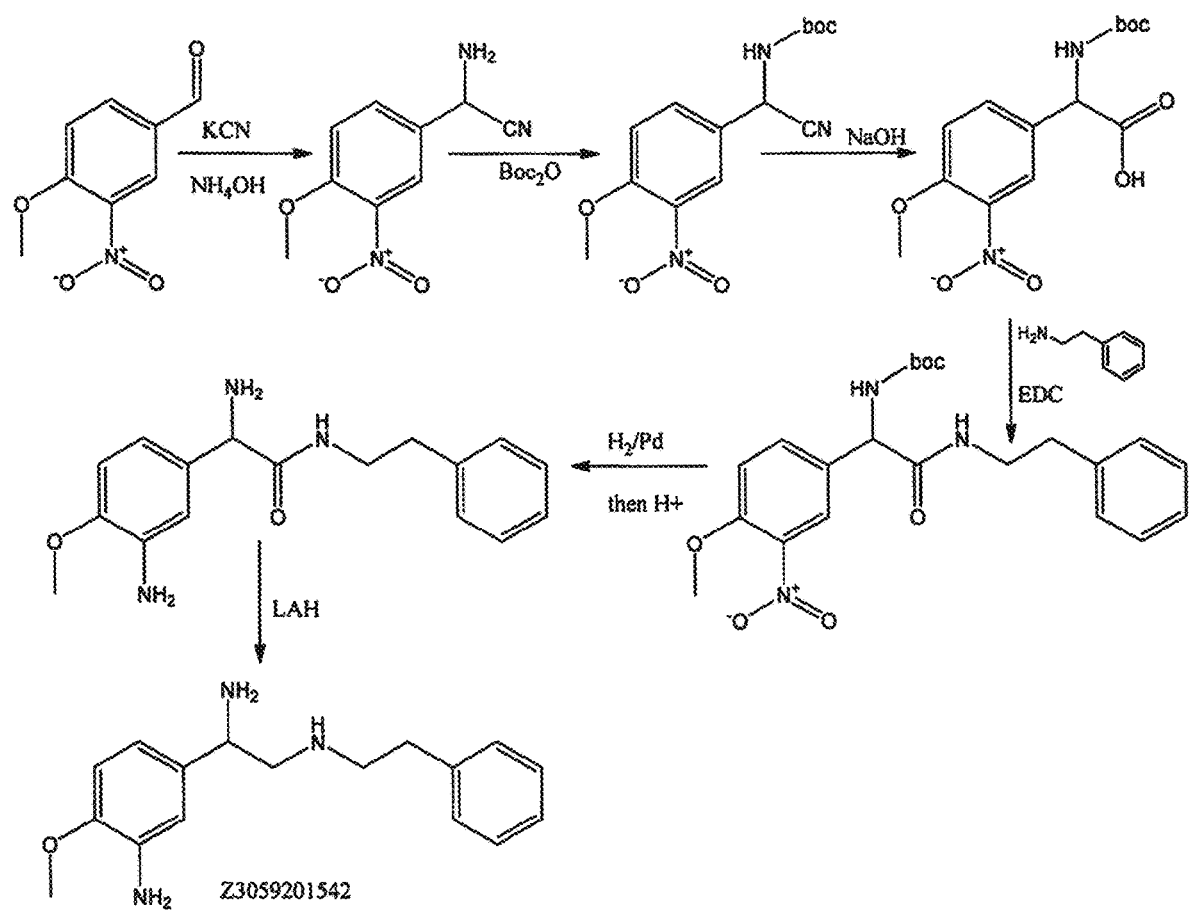
SCHEME 8
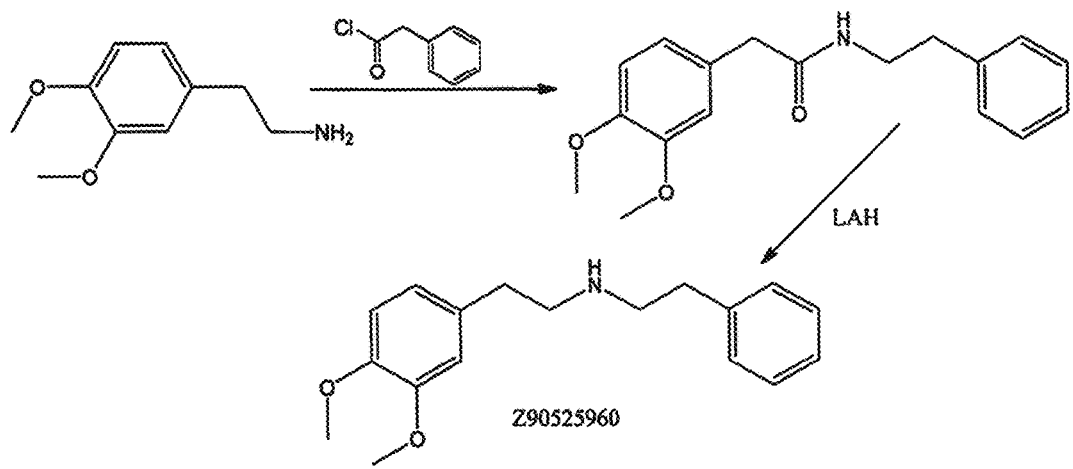
SCHEME 9
FIG. 39

SCHEME 10

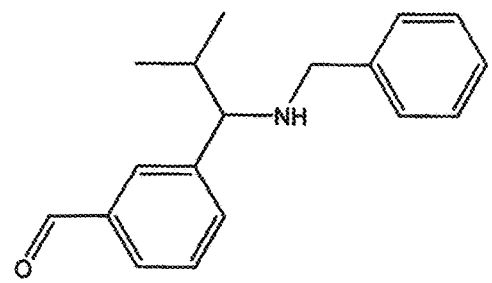
Benzald I
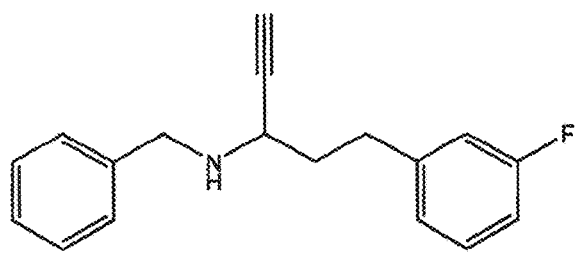
Fluorophenyl
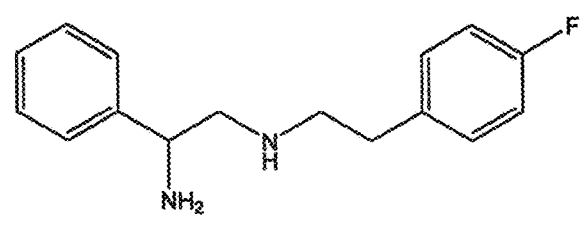
Aminofluorphenyl
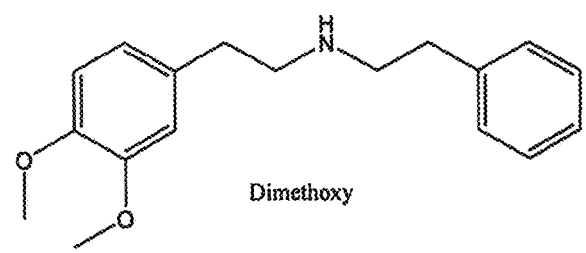
Dimethoxy
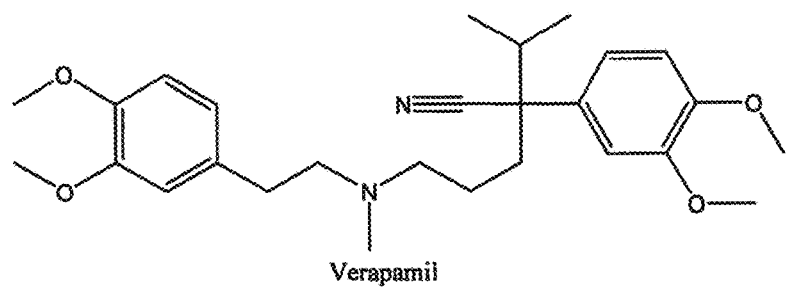
Verapamil
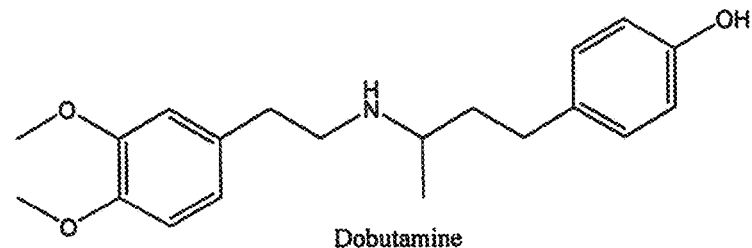
Dobutamine
FIG. 41

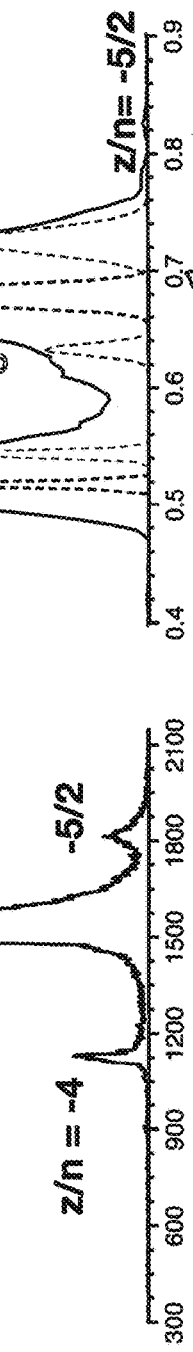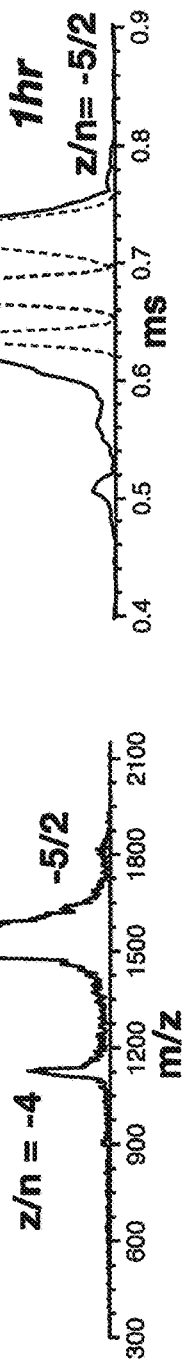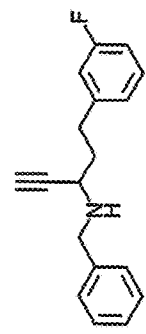
FIG. 44

SUBSTITUTED AMINES AS DISRUPTERS OF ABETA42 OLIGOMER FORMATION

RELATED APPLICATIONS

This application is a divisional of U.S. patent application Ser. No. 16/350,344, filed Nov. 5, 2018, entitled "Small Molecule Drugs And Related Methods for Treatment of Diseases Related to Aβ42 Oligomer Formation", which claims the benefit of U.S. Provisional Application No. 62/707,516, filed Nov. 6, 2017, each of which is incorporated by reference into this document for all purposes.

This invention was made with Government support under NSF SBIR Phase I Award #1143484 entitled, "Identifying Drug Leads Via 3D Pharmacophore Space Analysis".

FIELD OF THE INVENTION

The present invention provides small molecule drugs and pharmaceutical compositions for the treatment and prevention of diseases related to the formation of Aβ42 oligomers in a subject.

BACKGROUND OF THE INVENTION

AD is a devastating disease characterized by progressive memory loss, behavioral changes, loss of cognitive skills, and neurodegeneration. It is the most common form of dementia, with over 5.4 million victims in the United States alone. With our aging demographics, these numbers are predicted to rise dramatically unless effective therapeutics are developed. Indeed, if current trends continue, estimates indicate that there will be 16 million patients in the U.S. by 2050 with an annual cost exceeding $1 trillion.

Unfortunately, currently available anti-AD drugs are only minimally useful, at best. Even more problematic: clinical trials of new drugs under development are failing with regularity. As just two high-profile examples, the clinical trial of the "Aβ immunization" strategy had to be halted because of encephalitis. A more recent phase III trial employing an updated version of the same strategy (Bapineuzumab) showed no evidence of clinical benefit on either of the primary measures, one cognitive and one functional. While some have argued that these trials failed because the drugs were not administered early enough in the pathological process (Reiman et al., *J. Alzheimers Dis.*, 26 Suppl 3:321-329 (2011)), antibody based strategies also suffer from very poor BBB permeability. Drug candidates with "disease-modifying" properties (e.g., targeting amyloid β (Aβ) and tau) are being investigated but clinical trials continue to fail (Giacobini and Gold *Nature Reviews Neurology*) (2013)).

Despite the above failures, the "amyloid hypothesis" remains a central and potentially cure-producing perspective for Alzheimer's. Indeed, Genentech, the NIH and the Banner Alzheimer's Institute have recently initiated a collaborative 5 year, $100 million dollar trial assessing the ability of Crenezumab, a humanized monoclonal antibody directed against Aβ, to prevent the onset of AD in a population that is pre-symptomatic but genetically destined to suffer early onset AD as a result of presenilin mutations. The rationale is to attempt to reduce the level of Aβ via the antibody.

Another important component of the (thus far unsuccessful) collective efforts to develop effective anti-AD therapeutics is that the research community was focused upon the wrong form of Aβ for many years. Specifically, it was believed for many years that the Aβ42 fibrils and plaques that scientists and physicians had been viewing in microscopes for nearly a century were the neurotoxic species. This may explain many failures in clinical trials including: small molecules: Tramiprosate, PBT1, PBT2, and ELND005 (scyllo-Inositol); and immunotherapies: bapineuzumab. In FIG. 1, the focus of these approaches would be the latter states of Aβ fibrils and β-sheets. However, it is now appreciated that the real agents of toxicity are early and soluble Aβ42 oligomers (Benilova et al., *Nat. Neurosci.*, 15(3):349-357 (2012); Busche et al., *Nat. Neurosci.*, 18(12): 1725-1727 (2015); Dahlgren et al., *Journal of Biological Chemistry* 277(35):32046-32053 (2002); Hayden and Teplow, *Alzheimers Res Ther.* 5(6):60 (2013)).

Some progress is being made in characterizing different oligomeric stages of the amyloid cascade of AD, and immunologically distinct classes of oligomers have been identified using EPR and thioflavin T fluorescence. Additionally, new antibodies (Wu et al., *Journal of Biological Chemistry* 285(9):6071-6079 (2010)) are being developed, such as gammabodies (Perchiacca et al., *Proceedings of the National Academy of Sciences* 109(1):84-89 (2012)), that differentially recognize soluble oligomers of Aβ using novel grafted fragment methods. While each of these methods, and others, are powerful and informative, none of them is able to determine the distribution of soluble oligomer states nor identify the structures of these states. Further while some screening of potential inhibitors has been done (e.g., Meng et al., *Biochemistry* 49(37):8127-8133 (2010)), the analytical methods are indirect and most often use the inhibition of Aβ fibril formation as an assay, even though these fibrils are now known not to be the proximate toxic agent.

The present invention thus provides therapeutic small molecule agents useful for disruption of Aβ42 oligomer formation, in particular the dodecamer form of Aβ42, and for treatment of Alzheimer's disease.

SUMMARY OF THE INVENTION

In one aspect, the present invention provides a method of reducing formation of or disrupting Aβ42 oligomers in a subject, the method comprising the step of administering to the subject in need thereof a therapeutically effective amount of a pharmaceutical composition comprising a compound selected from the group consisting of AC0101, AC0102, AC0103, AC0104, AC0105, AC0106 and AC0107.

In another aspect, the Aβ42 oligomer is a dodecamer, hexamer or higher order oligomer and formation of or the amount of the Aβ42 dodecamer, hexamer or higher order oligomer is reduced.

In another aspect, administration of the pharmaceutical composition results in improved or enhanced cognitive function in a subject with decreased cognitive function. In another embodiment, the subject is diagnosed with AD, is genetically predisposed to AD, has the gene for early onset familial AD, or is at risk for developing AD.

In another aspect, administration of the pharmaceutical composition results in improved eyesight or slowing of eyesight degeneration in a subject having macular degeneration or glaucoma.

In another aspect, the compound is N-[4-({[2-(3-chlorophenyl)ethyl]amino}methyl)-phenyl]acetamide (A0101); (2,3-dihydro-1,4-benzodioxin-6-ylmethyl)({4 [(dimethylamino)-methyl]phenyl}methyl)amine (A0102); 2-[4-(4-hydroxyphenyl)piperazin-1-yl]-N,N-dimethyl-2 phenylacetamide (A0103); 3-[({[4-(morpholin-4 ylmethyl)phenyl]methyl}amino)-methyl]benzonitrile (A0104); 4-({[3-(1-pyrrolidinylmethyl)benzyl]amino}methyl)benzonitrile (AC0105); 4-{1-[(5-methyl-1,2-oxazol-3-yl)methyl]-1,2,3,6 tetrahydropyridin-4-yl}phenol (A0106); or 4-[({[3-(pyrrolidin-1-ylmethyl)phenyl]methyl}amino)methyl]benzonitrile.

In another aspect, the present invention provides a method of reducing formation of or disrupting Aβ42 oligomers in a subject, the method comprising the step of administering to the subject in need thereof a therapeutically effective amount of a pharmaceutical composition comprising a compound selected from the group consisting of the following compounds: 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224 (which are shown in FIGS. 9-29).

BRIEF DESCRIPTION OF THE DRAWINGS

FIG. 8 shows certain compounds of the present invention, A0101-A0107.

FIGS. 9-29 show certain compounds according to the present invention for the treatment of AD or a related disease.

FIGS. 30-34 show further compounds according to the present invention for the treatment of AD or a related disease.

FIGS. 35-40 show synthetic schemes to make certain compounds according to the present invention.

FIG. 41 shows certain compounds according to the present invention for the treatment of AD or a related disease.

FIGS. 42-56 show mass spectra and ATDs of several molecules, including Benzald1, Fluorophenyl, Aminofluorophenyl, Dimethoxy, Verapamil, Dobutamine and Cinacalcet.

DETAILED DESCRIPTION OF THE INVENTION

Figure 1:
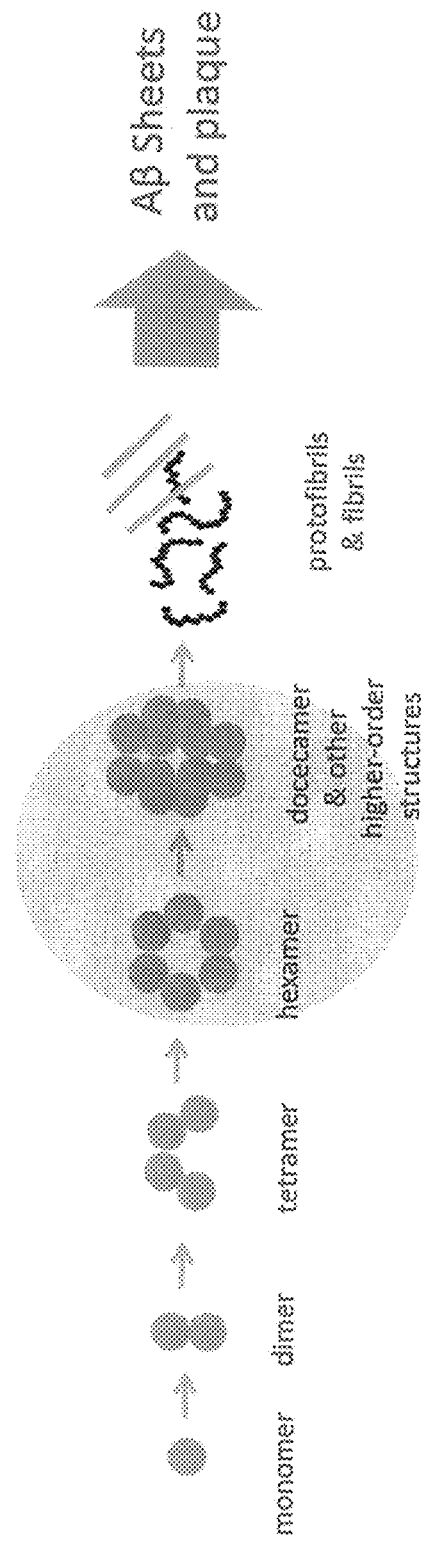
FIG. 1 shows an amyloid hypothesis involving states and transitions for the assembly of Aβ42 oligomers. The states are monomer, dimer, tetramer, hexamer, dodecamer and higher order structures. The dodecamer is the largest observed oligomer, it is metastable and eventually seeds protofibril formation.

Alzheimer's disease (AD) is a neurodegenerative disease diagnosed most often in people over 65 years of age, although 4% to 5% of cases are early onset familial AD, an autosomal dominant mutation, which is often manifested before the age of 65. AD results in impaired cognitive function and related symptoms. The most common early symptom is short-term memory loss. With advancing disease, symptoms can include problems with language, disorientation, mood swings, loss of motivation, self-care difficulties, and behavioral issues. As a person's condition declines, they often withdraw from family and society. Gradually, bodily functions are lost, ultimately leading to death. Although the speed of progression can vary, the average life expectancy following diagnosis is three to nine years.

Alzheimer's disease may be early or late onset. Risk factors include family history and genetic or biochemical markers. Genetic markers of risk for Alzheimer's disease include mutations in the APP gene, particularly mutations at position 717 and positions 670 and 671 referred to as the Hardy and Swedish mutations respectively. Other markers of risk are mutations in the presenilin genes, PS1 and PS2, and ApoE4, family history of Alzheimer's Disease, hypercholesterolemia or atherosclerosis. Individuals presently suffering from Alzheimer's disease can be recognized from characteristic dementia, as well as the presence of risk factors described above. In addition, a number of diagnostic tests are available for identifying individuals who have Alzheimer's disease. These include measurement of CSF tau and $A\beta_{1-42}$ levels. Individuals suffering from Alzheimer's disease can also be diagnosed by ADRDA criteria or the method disclosed herein.

In asymptomatic patients, treatment can begin at any age (e.g., 10, 20, 30 years of age). Usually, however, it is not necessary to begin treatment until a patient reaches 40, 50, 60, or 70 years of age. Treatment typically entails multiple dosages over a period of time.

Alzheimer's disease is characterized by senile plaque formation. Plaques are made up of small peptides, about 42 amino acids in length, called amyloid beta (Aβ). Aβ is a fragment from the larger amyloid precursor protein (APP). Recent research implicates soluble Aβ42 oligomers formed at the beginning of the amyloid assembly cascade as the agents of neurotoxicity in AD, in particular the higher order states such as hexamer and dodecamer oligomers (Bernstein et al., *Nature Chemistry* 1(4):326-331 (2009); Bernstein et al., *Journal of the American Chemical Society* 127(7):2075-2084 (2005); Cheng, et al., *Journal of Biological Chemistry* 282(33):23818-2382 (2007); Lesné, et al., *Nature*, 440 (7082):352-357 (2006).

The present invention is therefore directed to small molecule compounds that reduce or inhibit or disrupt Aβ42 oligomer formation, thereby treating or preventing Alzheimer's disease and/or enhancing cognitive function in a patient who has diminished cognitive function.

The term "cognitive function" refers to the intellectual process by which one becomes aware of, perceives, or comprehends ideas. Cognitive function embraces the quality of knowing, which includes all aspects of perception; recognition; conception; sensing; thinking; reasoning; remembering and imagining. The invention is also directed to inhibiting, treating or preventing decline of cognitive function.

Diminished cognitive function may be caused by a number of diseases. The terms "disease," "disorder," and "condition" are used inclusively and refer to any condition mediated at least in part by Aβ42 oligomers. In the context of this invention the disease may be associated with insoluble amyloid fibrils, senile plaques, neurofibrillary tangles, and/or the over-expression of amyloid $\beta_{1-42}$ protein. Examples include, but are not limited to, Alzheimer's disease, Down's Syndrome, mild cognitive impairment, stroke, focal ischemia associated dementia, and neuronal degeneration. Patients amenable to treatment include individuals at risk of disease but not exhibiting symptoms, as well as patients presently exhibiting symptoms. Therefore, the compounds described herein can be administered prophylactically to the general population without the need for any assessment of the risk of the patient.

The term "diminished cognitive function" or "decline of cognitive function" refers to memory loss, mental slowing, intellectual decline and/or amnesia. Memory loss may be characterized as the difficulty or failure for immediate or delayed recall. Mental slowing is the difficulty in processing or completing previously learned tasks in a timely manner or in processing new information quickly. Intellectual decline is defined as a loss of information, or an inability to utilize information previously possessed or utilized by a person. Amnesia is an extreme loss of cognitive ability that results in partial or total inability to recall past experiences and impaired or total loss of the ability to speak or write. Diminished cognitive function may be caused by a number of disease conditions which are more thoroughly discussed below.

Methods of assessing cognitive function include, but are not limited to, standardized instruments for example Folstein Mini-Mental State Examination; Modified Mini-Mental State Exam; Middlesex Elderly Assessment of Mental State; Short Portable Mental Status Questionnaire; Alzheimer's Disease Assessment Scale; Clock Drawing Test; Clinical Dementia Rating; Neuropsychiatric Inventory or any similarly designed test. Using the above listed tests, a skilled clinician would be able to assess the level of diminished cognitive function of a patient or enhanced cognitive function following treatment. Additionally, informal observations and interactions of individuals to a patient can also be used to assess cognitive function and include, but are not limited to, family members, friends, formal care givers such as nurses, and individuals who have previous intimate knowledge of the patient.

Mechanical measure of the neurons and neuronal tissue may also be used to assess cognitive function including, but not limited to, Computed Tomography (CT); Computed Axial Tomography (CAT); Magnetic Resonance Imaging (MRI); Functional Magnetic Resonance Imaging (fMRI); Positron Emission Tomography (PET): Single Photon Emission Computed Tomography (SPECT); Diffuse Optical Imaging (DOI); Diffuse Optical Tomography (DOT) or any similarly designed instrumentation.

The term "oligomeric" or "oligomer" means a protein complex of a finite number of monomer subunits. In the context of the invention, oligomers are referred to as trimers, low-n-mers, hexamers, dodecamers (12-mers), and large-n-multimers composed of $A\beta_{1-42}$ peptides.

The term "patient" or "subject" refers to animals, including mammals, humans, and non-human mammals. In certain embodiments, a patient is an animal, particularly an animal selected from a mammalian species including rat, rabbit, bovine, ovine, porcine, canine, feline, murine, equine, and primate, particularly human. In a preferred embodiment, the patient or subject is human.

"Treating" or "treatment of" a disease includes: (1) preventing the disease, i.e., causing the clinical symptoms of the disease not to develop in a patient that may be exposed to or predisposed to the disease but does not yet experience or display symptoms of the disease; (2) inhibiting the disease, i.e., arresting or reducing the development of the disease or its clinical symptoms; (3) relieving the disease, i.e., causing regression of the disease or its clinical symptoms; or (4) reducing the clinical symptoms of the disease.

The term "suffering" or "in need thereof" as it related to the term "treatment" refers to a patient or individual who has been diagnosed with or is predisposed to a disease. A patient may also be referred to being "at risk of suffering" from a disease. This patient has not yet developed characteristic disease pathology, however are know to be predisposed to the disease due to family history, being genetically predisposed to developing the disease, or diagnosed with a disease or disorder that predisposes them to developing the disease to be treated.

In addition to Alzheimer's disease, other diseases are known to be associated with $A\beta_{1-42}$ formation including, but are not limited to, Down's Syndrome, stroke, mild cognitive impairment, macular degeneration and glaucoma. It is conceivable that similar to Alzheimer's disease, treatment of patients suffering from or at risk of suffering from these diseases is possible due to the parallel mechanisms of the diseases.

In therapeutic applications, a pharmaceutical composition containing one or more compounds described herein is administered to a patient suspected of, or already suffering from AD or a related disease, wherein said compounds are administered in an amount sufficient to cure, or at least partially arrest, the symptoms of the disease (biochemical, histological and/or behavioral), including its complication and intermediate pathological phenotypes in development of the disease. In prophylactic applications, a pharmaceutical composition containing one or more compounds described herein is administered to a patient susceptible to, or otherwise at risk of, AD or a related disease, wherein said compounds are administered in an amount sufficient to eliminate or reduce the risk, lessen the severity, or delay the outset of the disease. This includes biochemical, histological and/or behavioral symptoms of the disease, its complications and intermediate pathological phenotypes presenting during development of the disease.

The "therapeutically effective amount" will vary depending on the compound, the disease and its severity and the age, weight, etc., of the patient to be treated all of which is within the skill of the attending clinician. It is contemplated that a therapeutically effective amount of one or more of the compounds described herein will alter or prevent Aβ oligomer accumulation in the brain of the patient as compared to the absence of treatment. As such, impairment of long-term potentiation and subsequent memory formation is decreased or prevented.

In some methods, administration of the compound reduces or eliminates mild cognitive impairment in patients that have not yet developed characteristic Alzheimer's pathology. In particular embodiments, a therapeutically effective amount intends to indicate the amount of one or more compounds described herein administered or delivered to the patient, which is most likely to result in the desired response to treatment.

Embodiments of the present invention also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts of the parent compound formed, for example, from non-toxic inorganic or organic acids. The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile (ACN) are preferred. Lists of suitable salts are found in Remington's *Pharmaceutical Sciences,* 17th ed., Mack Publishing Company, Easton, Pa., 1985, p. 1418 and *Journal of Pharmaceutical Science,* 66, 2 (1977), each of which is incorporated herein by reference in its entirety.

For oral administration, the pharmaceutically acceptable formulation may include a carrier, which may include, but is not limited to, a binder, a lubricant, a disintegrant, an excipient, a solubilizer, a dispersing agent, a stabilizer, a suspending agent, a colorant, and a flavorant. For injectable preparations, the carrier may include a buffering agent, a preserving agent, an analgesic, a solubilizer, an isotonic agent, and a stabilizer. For preparations for topical administration, the carrier may include a base, an excipient, a lubricant, and a preserving agent.

The disclosed compositions may be formulated into a variety of dosage forms in combination with the aforementioned pharmaceutically acceptable carriers. For example, for oral administration, the pharmaceutical composition may be formulated into tablets, troches, capsules, elixirs, suspensions, syrups or wafers. For injectable preparations, the pharmaceutical composition may be formulated into an ampule as a single dosage form or a multidose container. The pharmaceutical composition may also be formulated into solutions, suspensions, tablets, pills, capsules and long-acting preparations.

Examples of the carrier, the excipient, and the diluent suitable for the pharmaceutical formulations include, without limitation, lactose, dextrose, sucrose, sorbitol, mannitol, xylitol, erythritol, maltitol, starch, acacia rubber, alginate, gelatin, calcium phosphate, calcium silicate, cellulose, methylcellulose, microcrystalline cellulose, polyvinylpyrrolidone, water, methylhydroxybenzoate, propylhydroxybenzoate, talc, magnesium stearate and mineral oils. In addition, the pharmaceutical formulations may further include fillers, anti-coagulating agents, lubricants, humectants, flavorants, and antiseptics.

Effective doses of the compositions of the present invention, for the treatment of the above described diseases vary depending upon may different factors, including means of administration, physiological state of the patient, whether the patient is human or an animal, other medications administered, and whether treatment is prophylactic or therapeutic. Usually, the patient is a human, but in certain embodiments, a patient is an animal, particularly an animal selected from a mammalian species including canine, feline, murine, equine, and primate.

The compounds can be administered on multiple occasions, wherein intervals between single dosages can be daily, weekly, monthly, or yearly. Intervals can also be irregular as indicated by measuring blood levels of $A\beta_{1-42}$ protein or oligomers in the patient. Alternatively, one or more of the compounds of the invention can be administered as a sustained-release formulation, in which case less frequent administration is required. Dosage and frequency may vary depending on the half-life of the compounds of the invention. In therapeutic applications, a relatively high dosage at relatively short intervals is sometimes required until progression of the disease is reduced or terminated, and preferably until the patient shows partial or complete amelioration of symptoms of the disease. Thereafter, the patient can be administered a prophylactic regime.

Administration of a pharmaceutical composition of the compounds described herein can be carried out via a variety of routes including, but are not limited to, oral, topical, pulmonary, rectal, subcutaneous, intradermal, intranasal, intracranial, intramuscular, intraocular, or intra-articular injection and the like. The most typical route of administration is oral, although other routes can be equally effective.

One or more compounds described herein can optionally be administered in combination with other biological or chemical agents that are at least partly effective in treatment of an $A\beta_{1-42}$ associated disease. An example of such an agent is, but are not limited to, $A\beta_{1-42}$ targeted antibodies as described in International Application Nos.: WO 2003/253673; WO 2006/014478, U.S. Pat. No. 2,489,195, U.S. Publication No. 2007-0048312, and U.S. application Ser. No. 11/571,532, which are incorporated herein by reference.

The compounds described herein may be administered to a patient in an amount sufficient to inhibit, regulate and/or $A\beta$ oligomers in said patient. A skilled clinician would be able to readily ascertain appropriate amounts of the compounds described here to effectively inhibit, regulate and/or modulate the formation of $A\beta$ oligomers in said patient. Contemplated amounts of the compounds described herein include for example, but are not limited to, from about 0.05 to 2000 mg/m2/day of one compound or more than one compound.

As noted above, the compounds described herein may be administered for example, but are not limited to, orally, topically, pulmonarily, rectally, subcutaneously, intradermally, intranasally, intracranially, intramuscularly, intraocularly, or intra-arterially and the like. The carrier or excipient or excipient mixture can be a solvent or a dispersive medium containing for example, but are not limited to, various polar or non-polar solvents, suitable mixtures thereof, or oils. As used herein "carrier" or "excipient" means a pharmaceutically acceptable carrier or excipient and includes any and all solvents, dispersive agents or media, coating(s), antimicrobial agents, iso/hypo/hypertonic agents, absorption-modifying agents, and the like. The use of such substances and the agents for pharmaceutically active substances is well known in the art. Moreover, other or supplementary active ingredients can also be incorporated into the final composition.

Diseases that are treated by the methods described herein include Alzheimer's disease, Down's Syndrome, stroke, mild cognitive impairment, focal ischemia associated dementia, neuronal degeneration, macular degeneration and glaucoma.

When employed as pharmaceuticals, the compounds of this invention are usually administered in the form of pharmaceutical compositions. These compounds can be administered by a variety of routes including oral, topical, pulmonary, rectal, subcutaneous, intradermal, intranasal, intracranial, intramuscular, intraocular, or intra-articular injection. These compounds are effective as both injectable and oral compositions. Such compositions are prepared in a manner well known in the pharmaceutical art and comprise at least one active compound.

This invention also includes pharmaceutical compositions that contain, as the active ingredient, one or more of the compounds described herein associated with pharmaceutically acceptable carriers. In making the compositions of this invention, the active ingredient is usually mixed with an excipient, diluted by an excipient or enclosed within such a carrier which can be in the form of a capsule, sachet, paper or other container. The excipient employed is typically an excipient suitable for administration to patient. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

Administration of therapeutic agents by intravenous formulation is well known in the pharmaceutical industry. An intravenous formulation should possess certain qualities aside from being just a composition in which the therapeutic agent is soluble. For example, the formulation should promote the overall stability of the active ingredient(s), also, the manufacture of the formulation should be cost effective. All of these factors ultimately determine the overall success and usefulness of an intravenous formulation.

Other accessory additives that may be included in pharmaceutical formulations of compounds of the present invention as follow: solvents: ethanol, glycerol, propylene glycol; stabilizers: ethylene diamine tetra acetic acid (EDTA), citric acid; antimicrobial preservatives: benzyl alcohol, methyl paraben, propyl paraben; buffering agents: citric acid/sodium citrate, potassium hydrogen tartrate, sodium hydrogen tartrate, acetic acid/sodium acetate, maleic acid/sodium maleate, sodium hydrogen phthalate, phosphoric acid/potassium dihydrogen phosphate, phosphoric acid/disodium hydrogen phosphate; and tonicity modifiers: sodium chloride, mannitol, dextrose.

The presence of a buffer may be necessary to maintain the aqueous pH in the range of from about 4 to about 8 and more preferably in a range of from about 4 to about 6. The buffer system is generally a mixture of a weak acid and a soluble salt thereof, e.g., sodium citrate/citric acid; or the mono-cation or di-cation salt of a dibasic acid, e.g., potassium hydrogen tartrate; sodium hydrogen tartrate, phosphoric acid/potassium di-hydrogen phosphate, and phosphoric acid/disodium hydrogen phosphate.

The amount of buffer system used is dependent on (1) the desired pH; and (2) the amount of drug. Generally, the amount of buffer used is in a 0.5:1 to 50:1 mole ratio of buffer:drug (where the moles of buffer are taken as the combined moles of the buffer ingredients, e.g., sodium citrate and citric acid) of formulation to maintain a pH in the range of 4 to 8 and generally, a 1:1 to 10:1 mole ratio of buffer (combined) to drug present is used.

One useful buffer in the invention is sodium citrate/citric acid in the range of 5 to 50 mg per mL of sodium citrate to 1 to 15 mg per mL of citric acid, sufficient to maintain an aqueous pH of 4-6 of the composition.

The buffer agent may also be present to prevent the precipitation of the drug through soluble metal complex formation with dissolved metal ions, e.g., Ca, Mg, Fe, Al, Ba, which may leach out of glass containers or rubber stoppers or be present in ordinary tap water. The agent may act as a competitive complexing agent with the drug and produce a soluble metal complex leading to the presence of undesirable particulates.

In addition, the presence of an agent, e.g., sodium chloride in an amount of about of 1-8 mg/mL, to adjust the tonicity to the same value of human blood may be required to avoid the swelling or shrinkage of erythrocytes upon administration of the intravenous formulation leading to undesirable side effects such as nausea or diarrhea and possibly to associated blood disorders. In general, the tonicity of the formulation matches that of human blood which is in the range of 282 to 288 mOsm/kg, and in general is 285 mOsm/kg, which is equivalent to the osmotic pressure corresponding to a 0.9% solution of sodium chloride.

The intravenous formulation can be administered by direct intravenous injection, i.v. bolus, or can be administered by infusion by addition to an appropriate infusion solution such as 0.9% sodium chloride injection or other compatible infusion solution.

The compositions can be formulated in an oral unit dosage form. The term "unit dosage forms" refers to physically discrete units suitable as unitary dosages for a patient, each unit containing a predetermined quantity of active material calculated to produce the desired therapeutic effect, in association with a suitable pharmaceutical excipient.

The total effective dose of the compositions disclosed herein may be administered to a patient in a single dose, or may be administered for a long period of time in multiple doses according to a fractionated treatment protocol. In the pharmaceutical composition disclosed herein, the content of active ingredient may vary depending on the disease severity. Preferably, the total daily dose of the compounds disclosed herein may be approximately 0.0001 to 500 mg per 1 kg of body weight of a patient. However, the effective dose of the compound is determined considering various factors including patient's age, body weight, health conditions, gender, disease severity, diet, and secretion rate, in addition to administration route and treatment frequency of the pharmaceutical composition. In view of this, those skilled in the art may easily determine an effective dose suitable for the particular use of the pharmaceutical composition disclosed herein. The pharmaceutical composition disclosed herein is not particularly limited to the formulation, and administration route and mode, as long as it shows suitable effects. Moreover, the pharmaceutical composition may be administered alone or in combination or coincident with other pharmaceutical formulations showing prophylactic or therapeutic efficacy In one embodiment, the dose of the composition may be administered daily, semi-weekly, weekly, bi-weekly, or monthly. The period of treatment may be for a week, two weeks, a month, two months, four months, six months, eight months, a year, or longer. The initial dose may be larger than a sustaining dose. In one embodiment, the dose ranges from a weekly dose of at least 0.10 mg, at least 0.50 mg, at least 1.0 mg, at least 5.0 mg, at least 10.0 mg, at least 50.0 mg, at least 100.0 mg, at least 500.0 mg, at least 1.0 g, at least 5.0 g, or at least 10.0 g. In one embodiment, a weekly dose may be at most 0.5 mg, at most 2.5 mg, at most 5.0 mg, at most 25.0 mg, at most 50.0 mg, at most 250.0 mg, at most 500.0 mg, at most 2.50 g, at most 5.0 g, at most 25.0 g or at most 50.0 g. In a particular aspect, the weekly dose may range from 1.0 mg to 50.0 g, from 10.0 mg to 25.0 g, or from 100 mg to 5.0 g.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation is then subdivided into unit dosage forms of the type described above containing from, for example, 0.05 to about 2000 mg of the active ingredient of the present invention.

The tablets or pills of the present invention may be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the novel compositions of the present invention may be incorporated for administration orally or by injection include aqueous solutions suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably, the compositions are administered by the oral or nasal respiratory route for local or systemic effect. Compositions in preferably pharmaceutically acceptable solvents may be nebulized by use of inert gases. Nebulized solutions may be breathed directly from the nebulizing device or the nebulizing device may be attached to a face masks tent, or intermittent positive pressure breathing machine. Solution, suspension, or powder compositions may be administered, preferably orally or nasally, from devices that deliver the formulation in an appropriate manner.

Compounds for the Treatment of AD or a Related Disease

"Acyl" refers to a ketone substituent, C(O)R, where R is alkyl or substituted alkyl, aryl or substituted aryl as defined herein.

"Alkenyl" refers to an unsaturated "alkyl" group that contains a double bond.

"Alkoxy" refers to an —OR group, where R is alkyl, or a substituted analogue thereof. Suitable alkoxy groups include, for example, methoxy, ethoxy, t-butoxy, etc.

"Alkyl" refers to a branched or unbranched, saturated or unsaturated, monovalent and hydrocarbon group, generally having from about 1-30 carbons and preferably, from 4-20 carbons and more preferably from 6-18 carbons. When the alkyl group has from 1-6 carbon atoms, it is referred to as a "lower alkyl." Branched structures have a branching motif similar to i-propyl, t-butyl, i-butyl, 2-ethylpropyl, etc. As used herein, the term encompasses "substituted alkyls," and "cyclic alkyl." The term $(C_1$-$C_8)$alkyl refers to an alkyl that has between one and eight carbon atoms.

"Alkynyl" refers to an unsaturated "alkyl" group that contains a triple bond.

"Amino" refers to —NRR', wherein R and R' are independently H, alkyl, aryl or substituted analogues thereof. "Amino" encompasses "alkylamino" denoting secondary and tertiary amines and "acylamino" describing the group RC(O)NR'.

"Aryl" refers to an aromatic substituent, which may be a single aromatic ring or multiple aromatic rings which are fused together, linked covalently, or linked to a common group such as a diazo, methylene or ethylene moiety. The common linking group may also be a carbonyl as in benzophenone. The aromatic ring(s) may include phenyl, naphthyl, biphenyl, diphenylmethyl and benzophenone among others. The term "aryl" encompasses "arylalkyl" and "substituted aryl."

"Arylalkyl" refers to a subset of "aryl" in which the aryl group is attached to another group by an alkyl group as defined herein.

"Aryloxy" refers to aromatic groups that are linked to another group directly through an oxygen atom. This term encompasses "substituted aryloxy" moieties in which the aromatic group is substituted as described above for "substituted aryl." Exemplary aryloxy moieties include phenoxy, substituted phenoxy, benzyloxy, phenethyloxy, etc.

"Aryloxyalkyl" refers to aromatic groups attached, through an oxygen atom to an alkyl group, as defined herein. The term "aryloxyalkyl" encompasses "substituted aryloxyalkyl" moieties in which the aromatic group is substituted as described for "substituted aryl." "Electron withdrawing group" refers to an atom or group that draws electron density from neighboring atoms towards itself through resonance or inductive effects. This includes groups such as —$NO_2$, —CN, —C(O)H, —C(O)R where "R" is an alkyl group, —$CO_2$R where "R" is an alkyl group, and —$CO_2$H.

"Halogen" refers to fluorine, bromine, chlorine and iodine atoms.

"Heteroaryl" refers to aromatic rings in which one or more carbon atoms of the aromatic ring(s) are replaced by a heteroatom such as nitrogen, oxygen or sulfur. Heteroaryl refers to structures that may be a single aromatic ring, multiple aromatic ring(s), or one or more aromatic rings coupled to one or more non-aromatic ring(s). In structures having multiple rings, the rings can be fused together, linked covalently, or linked to a common group such as a diazo, methylene or ethylene moiety. The common linking group may also be a carbonyl as in phenyl pyridyl ketone. As used herein, rings such as thiophene, pyridine, isoxazole, phthalimide, pyrazole, indole, furan, etc. or benzo-fused analogues of these rings are defined by the term "heteroaryl."

"Heteroarylalkyl" refers to a subset of "heteroaryl" wherein an alkyl group, as defined herein, links the heteroaryl group to another group.

"Heterocyclic" refers to a monovalent saturated or unsaturated non-aromatic group having a single ring or multiple condensed rings from 1-12 carbon atoms and from 1-4 heteroatoms selected from nitrogen, sulfur or oxygen within the ring. Such heterocycles are, for example, tetrahydrofuran, morpholine, piperidine, pyrrolidine, etc.

"Heterocyclicalkyl" refers to a subset of "heterocyclic" wherein an alkyl group, as defined herein, links the heterocyclic group to another group.

"Hydroxy" refers to the group —OH.

"Mercapto" refers to moieties of the general structure —S—R wherein R is H, alkyl, aryl or heterocyclic as described herein.

"Saturated cyclic hydrocarbon" refers to groups such as the cyclopropyl, cyclobutyl, cyclopentyl, etc., and substituted analogues of these structures. These cyclic hydrocarbons can be single- or multi-ring structures.

"Substituted alkenyl" refers to an "alkenyl" that includes one or more substituents such as, for example, lower alkyl, aryl, acyl, halogen (e.g., alkylhalos), hydroxy, amino, alkoxy, alkylamino, acylamino, thioamido, acyloxy, aryloxy, aryloxyalkyl, mercapto, thia, aza, oxo, both saturated and unsaturated cyclic hydrocarbons, heterocycles and the like. These groups may be attached to any carbon or substituent of the alkenyl moiety. Additionally, these groups may be pendent from, or integral to, the alkenyl chain.

"Substituted alkyl" refers to an "alkyl" that includes one or more substituents such as, for example, lower alkyl, aryl, acyl, halogen (e.g., alkylhalos), hydroxy, amino, alkoxy, alkylamino, acylamino, thioamido, acyloxy, aryloxy, aryloxyalkyl, mercapto, thia, aza, oxo, both saturated and unsaturated cyclic hydrocarbons, heterocycles and the like. These groups may be attached to any carbon or substituent of the alkyl moiety. Additionally, these groups may be pendent from, or integral to, the alkyl chain.

"Substituted alkynyl" refers to an "alkynyl" that includes one or more substituents such as, for example, lower alkyl, aryl, acyl, halogen (e.g., alkylhalos), hydroxy, amino, alkoxy, alkylamino, acylamino, thioamido, acyloxy, aryloxy, aryloxyalkyl, mercapto, thia, aza, oxo, both saturated and unsaturated cyclic hydrocarbons, heterocycles and the like. These groups may be attached to any carbon or substituent of the alkynyl moiety. Additionally, these groups may be pendent from, or integral to, the alkynyl chain.

"Substituted aryl" refers to an "aryl" that includes one or more functional groups such as lower alkyl, acyl, halogen, alkylhalos (e.g. $CF_3$), hydroxy, amino, alkoxy, alkylamino, acylamino, acyloxy, phenoxy, mercapto and both saturated and unsaturated cyclic hydrocarbons which are fused to the aromatic ring(s), linked covalently or linked to a common group such as a diazo, methylene or ethylene moiety. The linking group may also be a carbonyl such as in cyclohexyl phenyl ketone. The term "substituted aryl" encompasses "substituted arylalkyl."

"Substituted arylalkyl" refers to a subset of "substituted aryl" wherein the substituted aryl group is attached to another group by an alkyl group as defined herein.

"Substituted heteroaryl" refers to a heteroaryl wherein the heteroaryl nucleus is substituted with one or more functional groups such as lower alkyl, acyl, halogen, alkylhalos (e.g. $CF_3$), hydroxy, amino, alkoxy, alkylamino, acylamino, acyloxy, mercapto, etc. Thus, substituted analogues of heteroaromatic rings such as thiophene, pyridine, isoxazole, phthalimide, pyrazole, indole, furan, etc. or benzo-fused analogues of these rings are defined by the term "substituted heteroaryl."

"Substituted heteroarylalkyl" refers to a subset of "substituted heteroaryl" in which an alkyl group, as defined herein, links the heteroaryl group to another group.

"Substituted heterocyclic" refers to a subset of "heterocyclic" wherein the heterocycle nucleus is substituted with one or more functional groups such as lower alkyl, acyl, halogen, alkylhalos (e.g., $CF_3$), hydroxy, amino, alkoxy, alkylamino, acylamino, acyloxy, mercapto, etc.

"Unsaturated cyclic hydrocarbon" refers to a monovalent non-aromatic group with at least one double bond, such as cyclopentene, cyclohexene, etc. and substituted analogues thereof. These cyclic hydrocarbons can be single- or multi-ring structures.

FIGS. 9-29 show certain compounds according to the present invention for the treatment of AD or a related disease. Where a cation is shown (e.g., compounds 102 and 106) a negatively charged, pharmaceutically acceptable counterion (e.g., AcO—) is implied.

Referring to FIG. 9, compound 100, substituents $R_1$, $R_3$-$R_6$, $R_{20}$-$R_{29}$ are independently selected (e.g., all can be the same or different) from a group consisting of: hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon.

Referring to FIG. 9, compound 102, substituents $R_1$-$R_6$, $R_{20}$-$R_{29}$ are independently selected (e.g., all can be the same or different) from a group consisting of: hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon.

Referring to FIG. 9, compound 104, substituents $R_3$-$R_6$, $R_{20}$-$R_{29}$ are independently selected (e.g., all can be the same or different) from a group consisting of: hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon.

Referring to FIG. 10, compound 106, substituents $R_3$-$R_6$, $R_{20}$, $R_{22}$, $R_{24}$, $R_{25}$-$R_{29}$ are independently selected (e.g., all can be the same or different) from a group consisting of: hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon.

Referring to FIG. 10, compound 108, substituents $R_3$-$R_6$, $R_{20}$, $R_{22}$, $R_{24}$, $R_{26}$-$R_{28}$ are independently selected (e.g., all can be the same or different) from a group consisting of: hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon.

Referring to FIG. 10, compound 110, substituents $R_3$-$R_6$, $R_{20}$, $R_{22}$, $R_{24}$, $R_{26}$-$R_{28}$ are independently selected (e.g., all can be the same or different) from a group consisting of: hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon.

Referring to FIG. 11, compound 112, substituents $R_{20}$, $R_{22}$, $R_{24}$, $R_{26}$-$R_{28}$ are independently selected (e.g., all can be the same or different) from a group consisting of: hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon.

Referring to FIG. 11, compound 114, substituents $R_{20}$, $R_{22}$, $R_{24}$, $R_{26}$-$R_{28}$ are independently selected (e.g., all can be the same or different) from a group consisting of: hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon.

Referring to FIG. 11, compound 116, substituents $R_{22}$, $R_{26}$ are independently selected (e.g., all can be the same or different) from a group consisting of: hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon.

Referring to FIG. 12, compound 118, substituents $R_{22}$, $R_{26}$ are independently selected (e.g., all can be the same or different) from a group consisting of: hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon.

Referring to FIG. 12, compound 120, substituents $R_1$, $R_3$-$R_8$, $R_{20}$-$R_{29}$ are independently selected (e.g., all can be the same or different) from a group consisting of: hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon.

Referring to FIG. 12, compound 122, substituents $R_1$-$R_8$, $R_{20}$-$R_{29}$ are independently selected (e.g., all can be the same or different) from a group consisting of: hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon.

Referring to FIG. 13, compound 124, substituents $R_3$-$R_8$, $R_{20}$, $R_{22}$, $R_{24}$, $R_{25}$-$R_{29}$ are independently selected (e.g., all can be the same or different) from a group consisting of: hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon.

Referring to FIG. 13, compound 126, substituents $R_3$-$R_8$, $R_{20}$, $R_{22}$, $R_{24}$, $R_{25}$-$R_{29}$ are independently selected (e.g., all can be the same or different) from a group consisting of: hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon.

Referring to FIG. 13, compound 128, substituents $R_3$-$R_8$, $R_{20}$, $R_{22}$, $R_{24}$, $R_{26}$-$R_{28}$ are independently selected (e.g., all can be the same or different) from a group consisting of: hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon.

Referring to FIG. 14, compound 130, substituents $R_{20}$, $R_{22}$, $R_{24}$, $R_{26}$-$R_{28}$ are independently selected (e.g., all can be the same or different) from a group consisting of: hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon.

Referring to FIG. 14, compound 132, substituents $R_{20}$, $R_{22}$, $R_{24}$, $R_{26}$-$R_{28}$ are independently selected (e.g., all can be the same or different) from a group consisting of: hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon.

Referring to FIG. 14, compound 134, substituents $R_{22}$, $R_{26}$ are independently selected (e.g., all can be the same or different) from a group consisting of: hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon.

Referring to FIG. 15, compound 136, substituents $R_{22}$, $R_{26}$ are independently selected (e.g., all can be the same or different) from a group consisting of: hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon.

Referring to FIG. 15, compound 138, substituents $R_1$, $R_3$-$R_{10}$, $R_{20}$-$R_{29}$ are independently selected (e.g., all can be the same or different) from a group consisting of: hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon.

Referring to FIG. 15, compound 140, substituents $R_1$-$R_{10}$, $R_{20}$-$R_{29}$ are independently selected (e.g., all can be the same or different) from a group consisting of: hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon.

Referring to FIG. 16, compound 142, substituents $R_3$-$R_{10}$, $R_{20}$-$R_{29}$ are independently selected (e.g., all can be the same or different) from a group consisting of: hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon.

Referring to FIG. 16, compound 144, substituents $R_3$-$R_{10}$, $R_{20}$-$R_{29}$ are independently selected (e.g., all can be the same or different) from a group consisting of: hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon.

Referring to FIG. 16, compound 146, substituents $R_3$-$R_{10}$, $R_{20}$, $R_{22}$, $R_{24}$, $R_{25}$-$R_{29}$ are independently selected (e.g., all can be the same or different) from a group consisting of: hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon.

Referring to FIG. 17, compound 148, substituents $R_3$-$R_{10}$, $R_{20}$, $R_{22}$, $R_{24}$, $R_{26}$-$R_{28}$ are independently selected (e.g., all can be the same or different) from a group consisting of: hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon.

Referring to FIG. 17, compound 150, substituents $R_{20}$, $R_{22}$, $R_{24}$, $R_{26}$-$R_{28}$ are independently selected (e.g., all can be the same or different) from a group consisting of: hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon.

Referring to FIG. 17, compound 152, substituents $R_{20}$, $R_{22}$, $R_{24}$, $R_{26}$-$R_{28}$ are independently selected (e.g., all can be the same or different) from a group consisting of: hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon.

Referring to FIG. 18, compound 154, substituents $R_{22}$, $R_{26}$ are independently selected (e.g., all can be the same or different) from a group consisting of: hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon.

Referring to FIG. 18, compound 156, substituents $R_{22}$, $R_{26}$ are independently selected (e.g., all can be the same or different) from a group consisting of: hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, sub- Referring to FIG. 18, compound 158, substituents $R_{40}$, $R_{42}$-$R_{48}$, $R_{50}$-$R_{54}$ are independently selected (e.g., all can be the same or different) from a group consisting of: hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon.

Referring to FIG. 19, compound 160, substituents $R_{40}$-$R_{48}$, $R_{50}$-$R_{54}$ are independently selected (e.g., all can be the same or different) from a group consisting of: hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon.

Referring to FIG. 19, compound 162, substituents $R_{40}$, $R_{44}$-$R_{46}$, $R_{50}$-$R_{54}$ are independently selected (e.g., all can be the same or different) from a group consisting of: hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon.

Referring to FIG. 19, compound 164, substituents $R_{40}$, $R_{41}$, $R_{44}$-$R_{46}$, $R_{50}$-$R_{54}$ are independently selected (e.g., all can be the same or different) from a group consisting of: hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon.

Referring to FIG. 20, compound 166, substituents $R_{40}$, $R_{44}$, $R_{50}$-$R_{54}$ are independently selected (e.g., all can be the same or different) from a group consisting of: hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon.

Referring to FIG. 20, compound 168, substituents $R_{40}$, $R_{41}$, $R_{44}$, $R_{50}$-$R_{54}$ are independently selected (e.g., all can be the same or different) from a group consisting of: hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon.

Referring to FIG. 20, compound 170, substituents $R_{40}$, $R_{50}$-$R_{54}$ are independently selected (e.g., all can be the same or different) from a group consisting of: hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon.

Referring to FIG. 21, compound 172, substituents $R_{40}$, $R_{41}$, $R_{50}$-$R_{54}$ are independently selected (e.g., all can be the same or different) from a group consisting of: hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon.

Referring to FIG. 21, compound 174, substituents $R_{40}$, $R_{51}$-$R_{53}$ are independently selected (e.g., all can be the same or different) from a group consisting of: hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon.

Referring to FIG. 21, compound 176, substituents $R_{40}$, $R_{41}$, $R_{51}$-$R_{53}$ are independently selected (e.g., all can be the same or different) from a group consisting of: hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon.

Referring to FIG. 22, compound 178, substituents $R_{40}$, $R_{52}$ are independently selected (e.g., all can be the same or different) from a group consisting of: hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon.

Referring to FIG. 22, compound 180, substituents $R_{40}$, $R_{41}$, $R_{52}$ are independently selected (e.g., all can be the same or different) from a group consisting of: hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon.

Referring to FIG. 22, compound 182, substituents $R_{60}$, $R_{62}$-$R_{69}$, $R_{80}$-$R_{84}$ are independently selected (e.g., all can be the same or different) from a group consisting of: hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon.

Referring to FIG. 23, compound 184, substituents $R_{60}$, $R_{61}$, $R_{62}$-$R_{69}$, $R_{80}$-$R_{84}$ are independently selected (e.g., all can be the same or different) from a group consisting of: hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon.

Referring to FIG. 23, compound 186, substituents $R_{60}$, $R_{64}$-$R_{67}$, $R_{80}$-$R_{84}$ are independently selected (e.g., all can be the same or different) from a group consisting of: hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon.

Referring to FIG. 23, compound 188, substituents $R_{60}$, $R_{61}$, $R_{64}$-$R_{67}$, $R_{80}$-$R_{84}$ are independently selected (e.g., all can be the same or different) from a group consisting of: hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon.

Referring to FIG. 24, compound 190, substituents $R_{60}$, $R_{81}$-$R_{83}$ are independently selected (e.g., all can be the same or different) from a group consisting of: hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon.

Referring to FIG. 24, compound 192, substituents $R_{60}$, $R_{61}$, $R_{81}$-$R_{83}$ are independently selected (e.g., all can be the same or different) from a group consisting of: hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon.

Referring to FIG. 24, compound 194, substituents $R_{60}$, $R_{82}$ are independently selected (e.g., all can be the same or different) from a group consisting of: hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon.

Referring to FIG. 25, compound 196, substituents $R_{60}$, $R_{61}$, $R_{82}$ are independently selected (e.g., all can be the same or different) from a group consisting of: hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon.

Referring to FIG. 25, compound 198, substituents $R_{60}$ is independently selected (e.g., all can be the same or different) from a group consisting of: hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon.

Referring to FIG. 25, compound 200, substituents $R_{60}$, $R_{61}$ are independently selected (e.g., all can be the same or different) from a group consisting of: hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon.

Referring to FIG. 26, compound 202, substituents $R_{91}$, $R_{93}$-$R_{96}$, $R_{100}$-$R_{108}$ are independently selected (e.g., all can be the same or different) from a group consisting of: hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon.

Referring to FIG. 26, compound 204, substituents $R_{91}$-$R_{96}$, $R_{100}$-$R_{108}$ are independently selected (e.g., all can be the same or different) from a group consisting of: hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon.

Referring to FIG. 26, compound 206, substituents $R_{111}$, $R_{113}$-$R_{116}$, $R_{120}$-$R_{127}$, $R_{129}$ are independently selected (e.g., all can be the same or different) from a group consisting of: hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon.

Referring to FIG. 27, compound 208, substituents $R_{111}$-$R_{116}$, $R_{120}$-$R_{127}$, $R_{129}$ are independently selected (e.g., all can be the same or different) from a group consisting of: hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon.

Referring to FIG. 27, compound 210, substituents $R_{131}$, $R_{133}$-$R_{136}$, $R_{140}$-$R_{146}$, $R_{148}$, $R_{149}$ are independently selected (e.g., all can be the same or different) from a group consisting of: hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon.

Referring to FIG. 27, compound 212, substituents $R_{131}$-$R_{136}$, $R_{140}$-$R_{146}$, $R_{148}$, $R_{149}$ are independently selected (e.g., all can be the same or different) from a group consisting of: hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon.

Referring to FIG. 28, compound 214, substituents $R_{151}$, $R_{153}$-$R_{156}$, $R_{163}$-$R_{167}$ are independently selected (e.g., all can be the same or different) from a group consisting of: hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon. "X" is O, S or NR where R is hydrogen or alkyl.

Referring to FIG. 28, compound 216, substituents $R_{151}$-$R_{156}$, $R_{163}$-$R_{167}$ are independently selected (e.g., all can be the same or different) from a group consisting of: hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon. "X" is O, S or NR where R is hydrogen or alkyl.

Referring to FIG. 28, compound 218, substituents $R_{171}$, $R_{173}$-$R_{176}$, $R_{180}$-$R_{186}$, $R_{188}$ are independently selected (e.g., all can be the same or different) from a group consisting of: hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon. "X" is O, S or NR where R is hydrogen or alkyl.

Referring to FIG. 29, compound 220, substituents $R_{171}$-$R_{176}$, $R_{180}$-$R_{186}$, $R_{188}$ are independently selected (e.g., all can be the same or different) from a group consisting of: hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon. "X" is O, S or NR where R is hydrogen or alkyl.

Referring to FIG. 29, compound 222, substituents $R_{191}$, $R_{193}$-$R_{196}$, $R_{200}$-$R_{206}$, $R_{209}$ are independently selected (e.g., all can be the same or different) from a group consisting of: hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon.

Referring to FIG. 29, compound 224, substituents $R_{191}$-$R_{196}$, $R_{200}$-$R_{206}$, $R_{209}$ are independently selected (e.g., all can be the same or different) from a group consisting of: hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon.

Other, nonlimiting examples of compound according to the present invention for the treatment of AD or a related disease include: N-[4-({[2-(3-chlorophenyl)ethyl]amino}methyl)-phenyl]acetamide (A0101); (2,3-dihydro-1,4-benzodioxin-6-ylmethyl)({4 [(dimethylamino)-methyl]phenyl}methyl)amine (A0102); 2-[4-(4-hydroxyphenyl) piperazin-1-yl]-N,N-dimethyl-2 phenylacetamide (A0103); 3-[({[4-(morpholin-4 ylmethyl)phenyl]methyl})-amino) methyl]benzonitrile (A0104); 4-({[3-(1-pyrrolidinylmethyl) benzyl]amino}methyl)-benzonitrile (AC0105); 4-{1-[(5-methyl-1,2-oxazol-3-yl)methyl]-1,2,3,6 tetrahydropyridin-4-yl}phenol (A0106); or 4-[({[3-(pyrrolidin-1-ylmethyl) phenyl]methyl}amino)methyl]-benzonitrile.

CERTAIN EMBODIMENTS

A compound of the following structure:

[Chemical structure with substituents $R_{40}$, $R_{42}$, $R_{43}$, $R_{44}$, $R_{45}$, $R_{46}$, $R_{47}$, $R_{48}$, $R_{50}$, $R_{51}$, $R_{52}$, $R_{53}$, $R_{54}$]

wherein $R_{40}$ is hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon;

$R_{42}$ is hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon;

$R_{43}$ is hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon;

$R_{44}$ is hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon;

$R_{45}$ is hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon;

$R_{46}$ is hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon;

$R_{47}$ is hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon;

$R_{48}$ is hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon;

$R_{50}$ is hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon;

$R_{51}$ is hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon;

$R_{52}$ is hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon;

$R_{53}$ is hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon;

$R_{54}$ is hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon.

The compound wherein $R_{40}$ is hydrogen, alkyl or acyl.

The compound wherein $R_{42}$, $R_{43}$, $R_{47}$ and $R_{48}$ are independently hydrogen or alkyl.

The compound wherein $R_{44}$-$R_{46}$ is hydrogen or alkyl.

The compound wherein $R_{50}$-$R_{54}$ is hydrogen, alkyl or halogen.

A compound of the following structure:

[Chemical structure with substituents $R_{60}$, $R_{62}$, $R_{63}$, $R_{64}$, $R_{65}$, $R_{66}$, $R_{67}$, $R_{68}$, $R_{69}$, $R_{80}$, $R_{81}$, $R_{82}$, $R_{83}$, $R_{84}$]

wherein $R_{60}$ is hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon;

$R_{62}$ is hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon;

$R_{63}$ is hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon;

$R_{64}$ is hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon;

$R_{65}$ is hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon;

$R_{66}$ is hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon;

$R_{67}$ is hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon;

$R_{68}$ is hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon;

$R_{69}$ is hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon;

$R_{80}$ is hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon;

$R_{81}$ is hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon;

$R_{82}$ is hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon;

$R_{83}$ is hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon; and $R_{84}$ is hydrogen, acyl, alkenyl, alkoxy, alkyl, alkynyl, amino, aryl, arylalkyl, aryloxy, aryloxyalkyl, electron withdrawing group, halogen, heteroaryl, heteroarylalkyl, heterocyclic, heterocyclicalkyl, hydroxy, mercapto, saturated cyclic hydrocarbon, substituted alkenyl, substituted alkyl, substituted alkynyl, substituted aryl, substituted arylalkyl, substituted heteroaryl, substituted heteroarylalkyl, substituted heterocyclic, or unsaturated cyclic hydrocarbon.

The compound wherein $R_{60}$ is hydrogen, alkyl or acyl.

The compound wherein $R_{62}$, $R_{63}$, $R_{68}$ and $R_{69}$ are independently hydrogen or alkyl.

The compound wherein $R_{64}$, $R_{65}$, $R_{66}$ and $R_{67}$ are independently hydrogen or alkyl.

The compound wherein $R_{80}$-$R_{84}$ are independently hydrogen, alkyl or halogen.

A method of reducing formation of or disrupting Aβ42 oligomers in a subject, the method comprising the step of administering to the subject in need thereof a therapeutically effective amount of a pharmaceutical composition comprising a compound selected from the group consisting of the following compounds: 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, Benzald1, Fluorophenyl, Aminofluorophenyl, and Dimethoxy.

A method of improving cognitive function in a subject with decreased cognitive function, the method comprising the step of administering to the subject in need thereof a therapeutically effective amount of a pharmaceutical composition comprising a compound selected from the group consisting of AC0101, AC0102, AC0103, AC0104, AC0105, AC0106, AC0107, Benzald1, Fluorophenyl, Aminofluorophenyl, and Dimethoxy.

A method of treating macular degeneration in a subject, the method comprising the step of administering to the subject in need thereof a therapeutically effective amount of a pharmaceutical composition comprising a compound selected from the group consisting of AC0101, AC0102, AC0103, AC0104, AC0105, AC0106, AC0107, Benzald1, Fluorophenyl, Aminofluorophenyl, and Dimethoxy.

A method of treating glaucoma in a subject, the method comprising the step of administering to the subject in need thereof a therapeutically effective amount of a pharmaceutical composition comprising a compound selected from the group consisting of AC0101, AC0102, AC0103, AC0104, AC0105, AC0106, AC0107, Benzald1, Fluorophenyl, Aminofluorophenyl, and Dimethoxy.

EXAMPLES

Certain Compounds of the Invention

| ID# | CAS# | Chemical name |
|---|---|---|
| AC0101 | 1209424-09-8 | N-[4-({[2-(3-chlorophenyl)ethyl]amino}methyl)phenyl]acetamide |
| AC0102 | 1014247-57-4 | (2,3-dihydro-1,4-benzodioxin-6-ylmethyl)({4[(dimethylamino)methyl]-phenyl}methyl)amine |
| AC0103 | 1214022-77-1 | 2-[4-(4-hydroxyphenyl)piperazin-1-yl]-N,N-dimethyl-2 phenylacetamide |
| AC0104 | 1241566-06-2 | 3-[({[4-(morpholin-4 ylmethyl)phenyl]methyl}amino)methyl]benzonitrile |
| AC0105 | 1241332-16-0<br>1384724-10-0 | 4-[({[4-(pyrrolidin-1 ylmethyl)phenyl]methyl}amino)methyl]benzonitrile |
| AC0106 | 1311839-93-6 | 4-{1-[(5-methyl-1,2-oxazol-3-yl)methyl]-1,2,3,6 tetrahydropyridin-4-yl}phenol |
| AC0107 | 1355835-03-8<br>1384715-28-9, | 4-[({[3-(pyrrolidin-1-ylmethyl)phenyl]methyl}amino)methyl]benzonitrile |

Membrane Trafficking Assay

Figure 2:
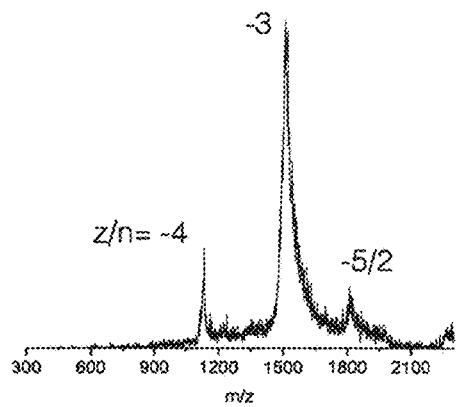
FIG. 2 shows a mass spectrum of wild type Aβ42.

Seven drug candidates (A0101-A0107) (FIG. 2) were tested in a primary cell biological screening assay capable of measuring Aβ oligomer induced changes in membrane trafficking in 21 DIV primary rodent neuronal cultures (see Izzo et al., PLoS ONE 9(11):e111899, 2014). Briefly, cultures were treated with either oligomeric Aβ or oligomeric Aβ plus a candidate compound for 24 hours. Non-Aβ treated cells served as a negative control. Next, a non-membrane permeable dye (MTT) was added to the dishes for 1 hour, during which time the dye can be internalized by endocytosis. At the end of the hour, the dye containing media was removed, the dishes were rinsed extensively with isotonic buffer, and finally, the washed cells were extracted with a Triton X-100 buffer to solubilize membranes and release the dye, which is quantitated. Aβ oligomers cause a dose-dependent decrease in the amount of intracellular vesicles containing reduced purple MTT, with an EC50 of 400 nM A☐ (of which we estimate 50% is oligomeric).

TABLE 1

| MTT ASSAY | |
|---|---|
| Compound ID | EC50 (µM) |
| AC0101 | 3.90 |
| AC0102 | 3.50 |
| AC0103 | 1.30 |
| AC0104 | 0.70 |
| AC0105 | 0.51 |
| AC0106 | 1.00 |
| AC0107 | 0.45 |

All seven compounds inhibited the deleterious effects of Aβ in this assay (Table 1). Importantly, previous work has shown that compounds exhibiting EC50 values of up to 3-4 µM in this membrane trafficking assay have also inhibited Aβ effects in mouse behavioral assays (Cheng et al., Journal of Biological Chemistry, 282(33):23818-23828, 2007).

Permeability Assay

Subsequently, Caco-2 A-B and B-A permeability tests (pH 7.4) were performed on the A0101-107 molecules in order to assess their human intestinal permeability and drug efflux. This assay measures the in vivo rate of transport of a compound across the Caco-2 cell line that is derived from a human colon carcinoma. The cells have characteristics that resemble intestinal epithelial cells such as the formation of a polarized monolayer, well-defined brush border on the apical surface and intercellular junctions. Assessing transport in both directions (apical to basolateral (A-B) and basolateral to apical (B-A)) across the cell monolayer enables an efflux ratio which provides an indicator as to whether a compound undergoes active efflux. The results of this assay are shown in columns 2 and 3 of Table 2. As a reference, the permeability of 4 reference compounds is shown at the bottom of the table. Of these, propranolol is highly BBB permeable.

TABLE 2

| CACO-2 PERMEABILITY AND TOXICITY OF COMPOUNDS A0101-107 | | | |
|---|---|---|---|
| Compound ID | A-B perm 10-6 cm/sec | B-A perm 10-6 cm/sec | hERG toxicity $IC_{50}$ µM |
| AC101 | 101.3 | 41.6 | 8 |
| AC102 | 30.0 | 4.5 | >10 |
| AC103 | 61.6 | 39.7 | >10 |
| AC104 | 59.4 | 13.9 | >10 |
| AC105 | 23.2 | 4.5 | >10 |
| AC106 | 74.4 | 42.3 | >10 |
| AC107 | 18.4 | 6.5 | >10 |
| colchicine | 0.1 | 13.9 | |
| labetalol | 11.9 | 46.2 | |
| propranolol | 60.6 | 24.2 | |
| ranitidine | 0.7 | 3.5 | |

Toxicity Assay

Finally, cardiac toxicity studies were performed for A0101-107 compounds in a Human Ether-á-go-go-Related-Gene channel (hERG) cellular assay. Contract laboratories provided screening of hERG ion channel cell lines as an indicator of cardiac safety. Drug candidates must not block the hERG channel, which is expressed in the mammalian heart and is crucial for repolarization and relaxation of cardiac muscle during every heartbeat. Potassium efflux occurs when the channel is open and the cardiac myocyte membrane potential is positive to the equilibrium potential for potassium. A prolonged QT-interval as measured on an electrocardiogram is indicative of a drug side-effect that can lead to lethal ventricular arrhythmias. Cellular "patch-clamp" assays provide the data required by ICH guidelines. The results of this assay are shown in the 4th column of Table 2 (hERG toxicity). Six of the compounds show weak or no inhibition while AC101 shows moderate potency.

All seven compounds assayed had low molecular weight (300-380 amu), were chemically stable, and "alkaloidal" in that they are monoamine- or diamine containing and formulated as HCl salts.

IMS-MS Assays for Aβ42-Selective Inhibitor Activity

Described herein is the IMS-MS method used to evaluate drug candidate A0107.

A physiologically relevant solution of Aβ42 and a drug candidate was incubated for varying periods of time and then loaded into a special spray capillary and the solution nano-electrosprayed, captured by an ion funnel, transported, dehydrated and continuously fed into a quadrapole mass analyser, and detected. This process yielded a mass spectrum. In order to obtain either structural or oligomeric information, the ions were next stored at the end of the funnel and then pulse injected at low energy into a drift cell filled with helium gas and subjected to a low electric field to transport the ions through the cell. The quadrapole is set to pass a particular mass to charge ratio (m=z), and an arrival time distribution (ATD) of the ions at this m=z is obtained at the detector (see, e.g., Bernstein et al., *Journal of the American Chemical Society,* 127(7):2075-2084, 2005). All molecules were at a concentration of 10 µM in 10 mM ammonium acetate.

Figure 3:
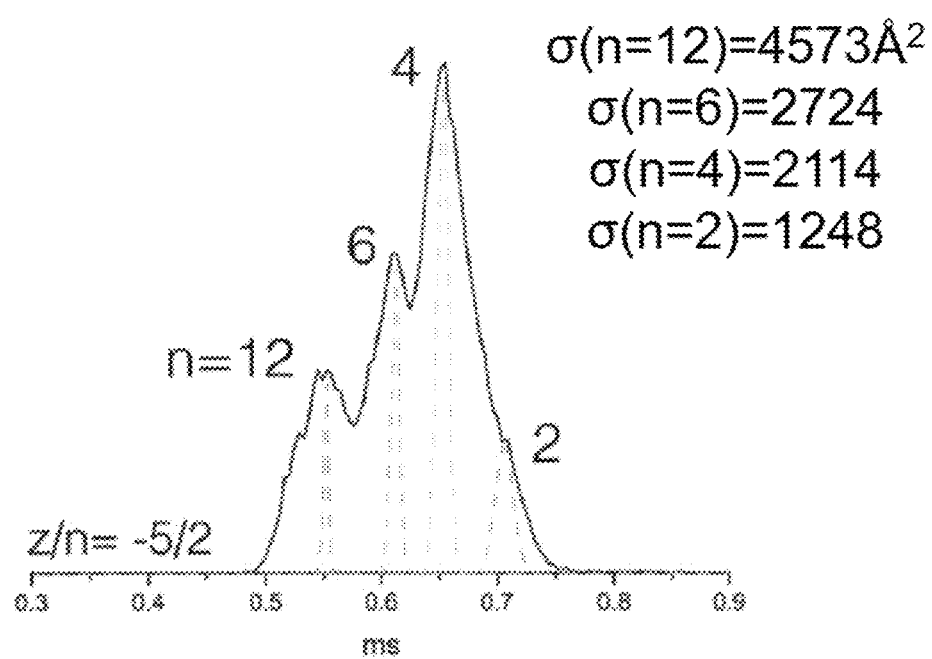
FIG. 3 shows arrival time distributions (ADT) for wild type Aβ42.

FIG. 3 shows a typical mass spectrum of wild type Aβ42 consisting of two peaks corresponding to monomers (z/n=−4, −3) and one peak corresponding to dimers and higher order oligomers (z/n=−5/2). By collecting Arrival Time Distributions (ATDs) of each of these charge states, ions of the same mass-to-charge (m/z) ratio were separated by their size and shape.

Figure 4:
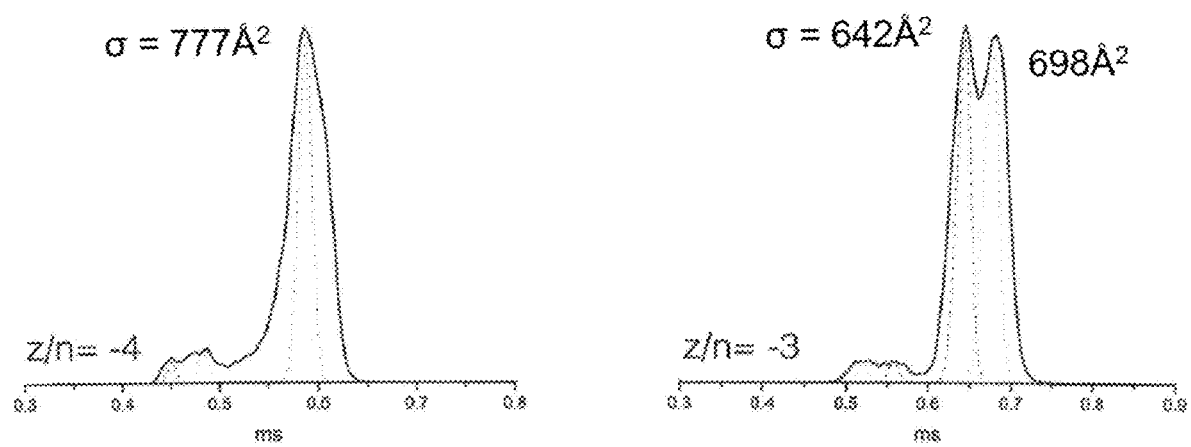
FIG. 4 shows typical ATDs of monomer charge states for wild type Aβ42.

FIG. 4 shows arrival time distributions (ADT) for wild type Aβ42. The plot shows a typical ATD of the z/n=−5/2 charge state for Aβ42 wt. Using kinetic theory and parameters of the experiment, arrival times are related to an ion's mobility in the drift cell, which is inversely proportional to the ion's collision cross section. Oligomer formation is shown for dimer (n=2) up to dodecamer (n=12) for the z/n=−5/2 charge state.

Figure 5:
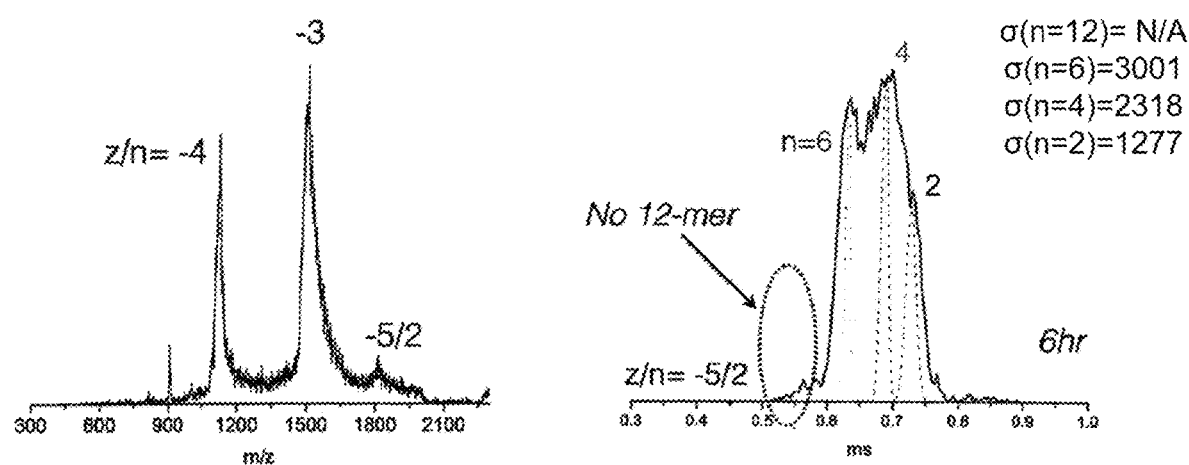
FIG. 5 shows ADTs of wild type Aβ42 plus 1:10 4-({[3-(1-pyrrolidinylmethyl)benzyl]-amino}methyl)benzonitrile (A0107) (Day 1).

FIG. 5 shows that earlier arrival times correspond to either higher order oligomers or more compact structures of the same oligomer order for wild type Aβ42. For example, the peak in z/n=−3 ATD with a collision cross section of 698 Å$^2$ corresponds to a less compact solution-phase monomer structure. The peak of 642 Å$^2$ corresponds to a more compact gas phase structure.

Figure 6:
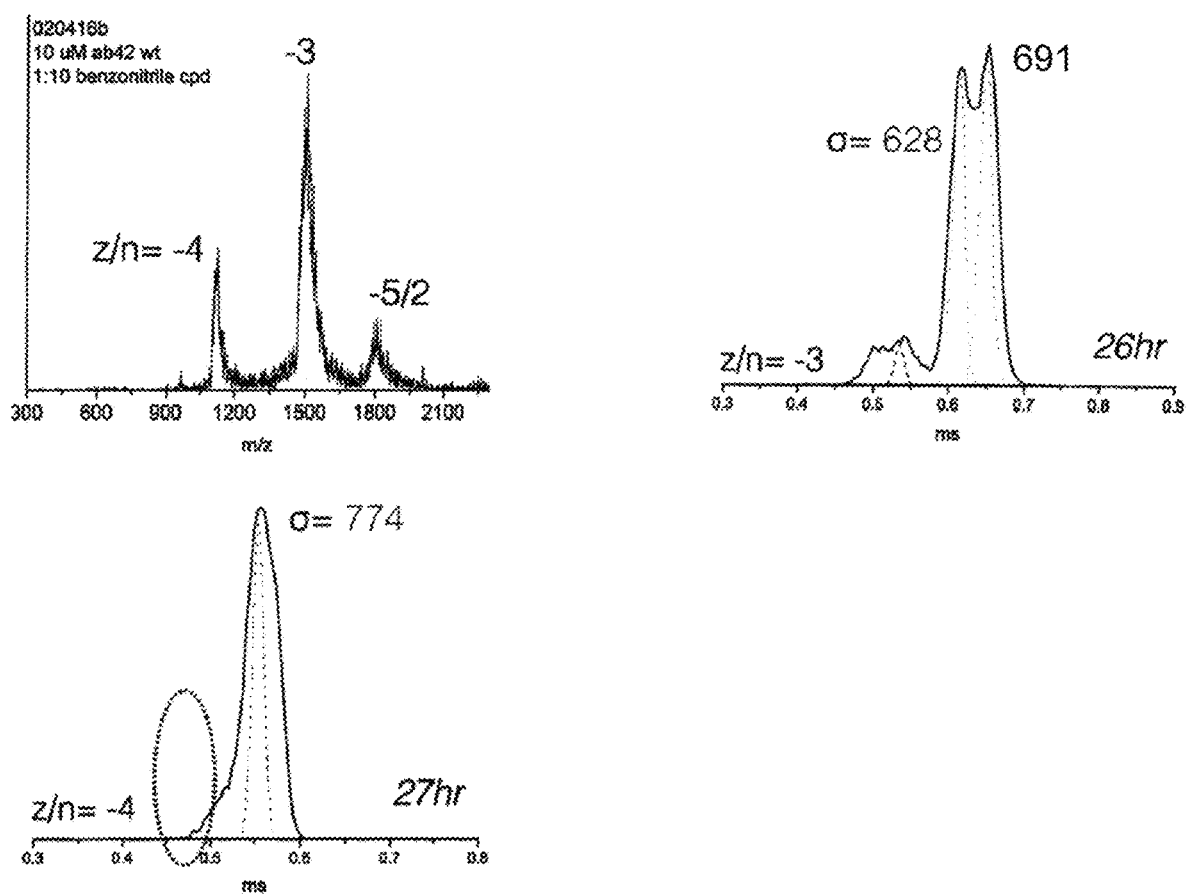
FIG. 6 shows a mass spectrum and ADTs of wild type Aβ42 plus 1:10 4-({[3-(1-pyrrolidinylmethyl)benzyl]amino}methyl)benzonitrile (A0107) (Day 2, 26 and 27 hours).

FIG. 6 shows that wild type Aβ42 dodecamer formation is inhibited with introduction of 1:10 Aβ42 wt to A0107 compound (day one).

Figure 7:
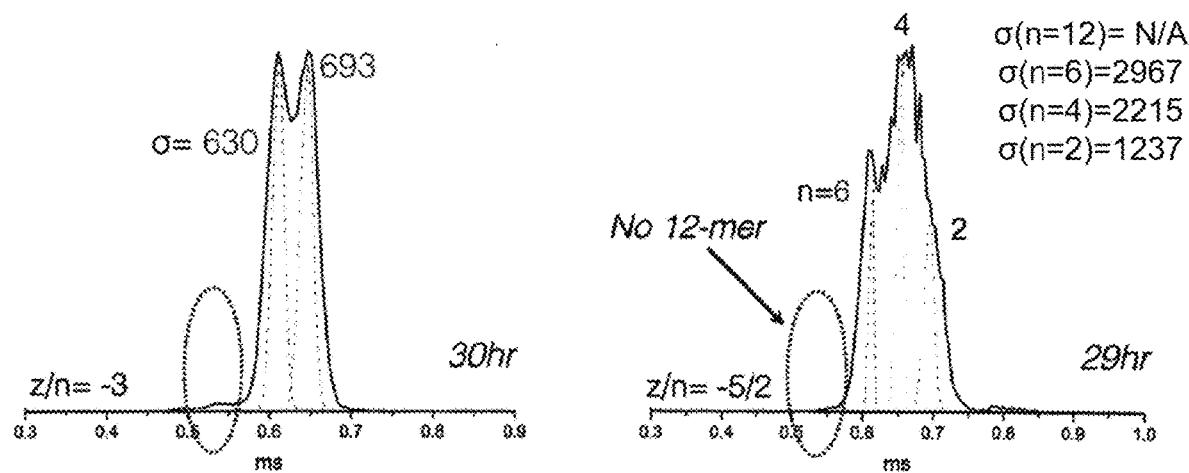
FIG. 7 shows ADTs of wild type Aβ42 plus 1:10 4-({[3-(1-pyrrolidinylmethyl)benzyl]-amino}methyl)benzonitrile (A0107) (Day 2, 29 and 30 hours).
Figure 36:
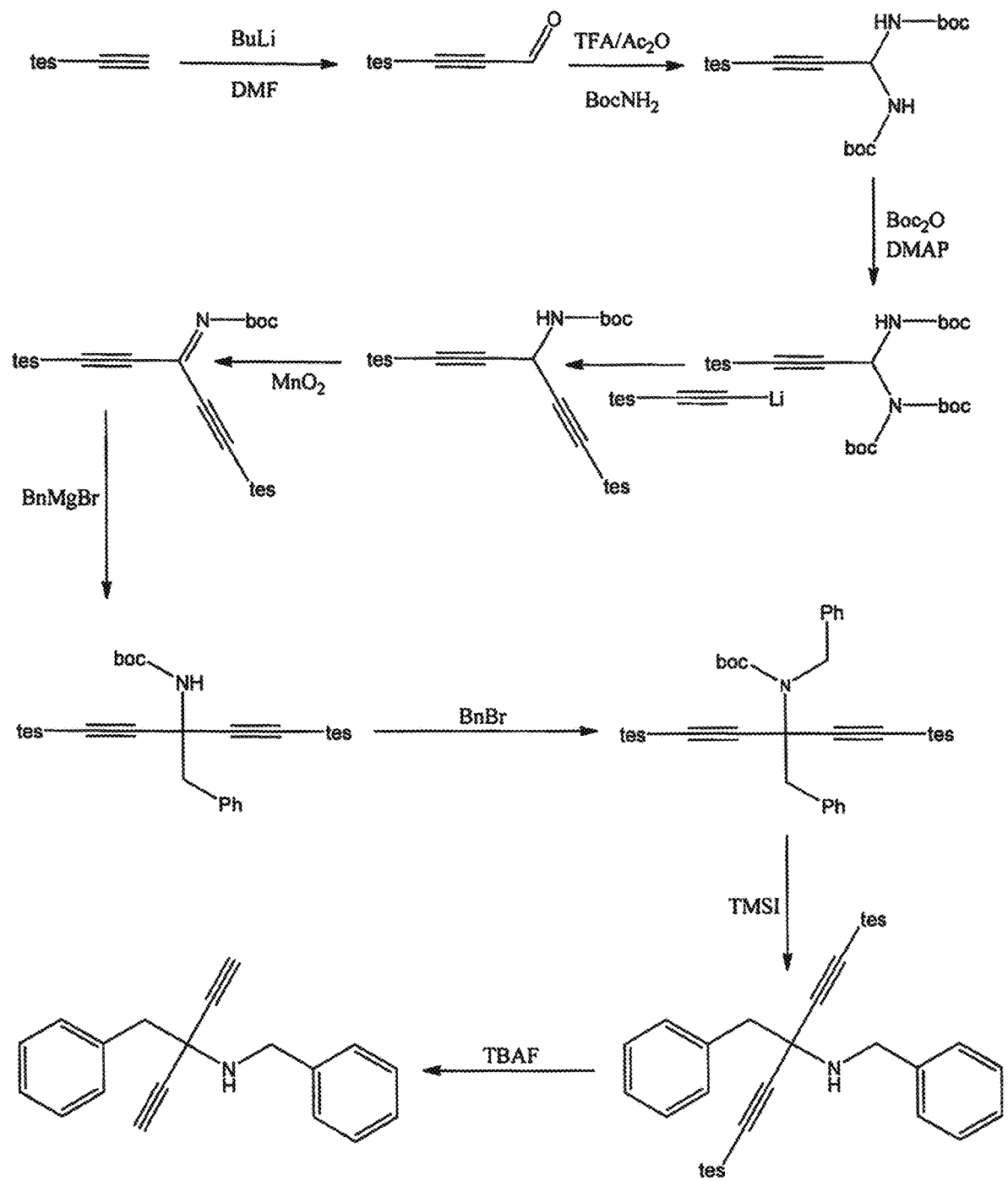
Figure 40:
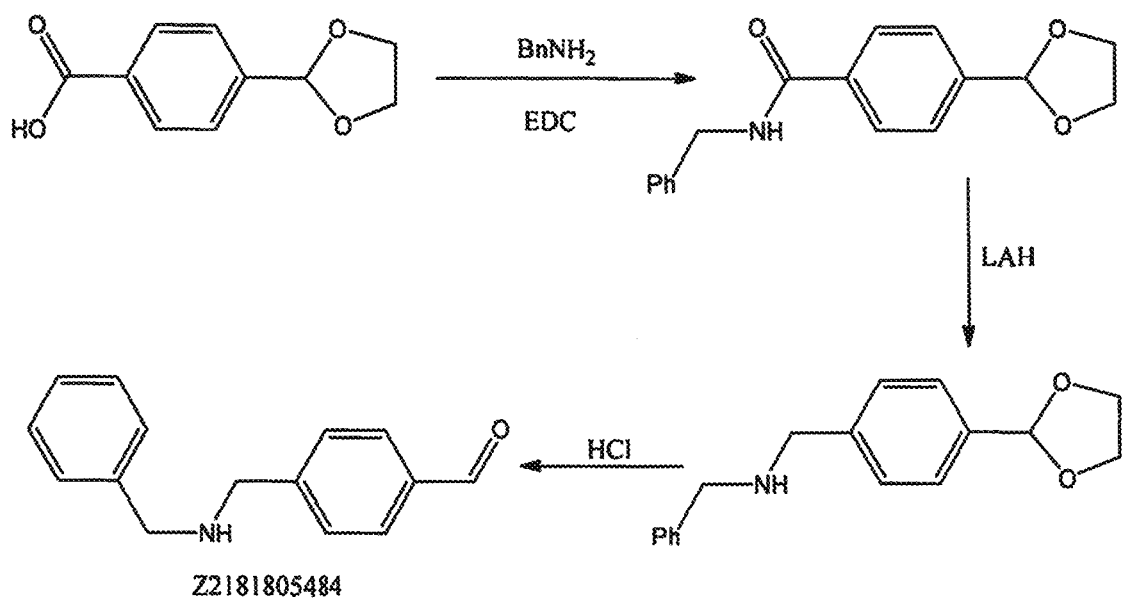
Figure 42:
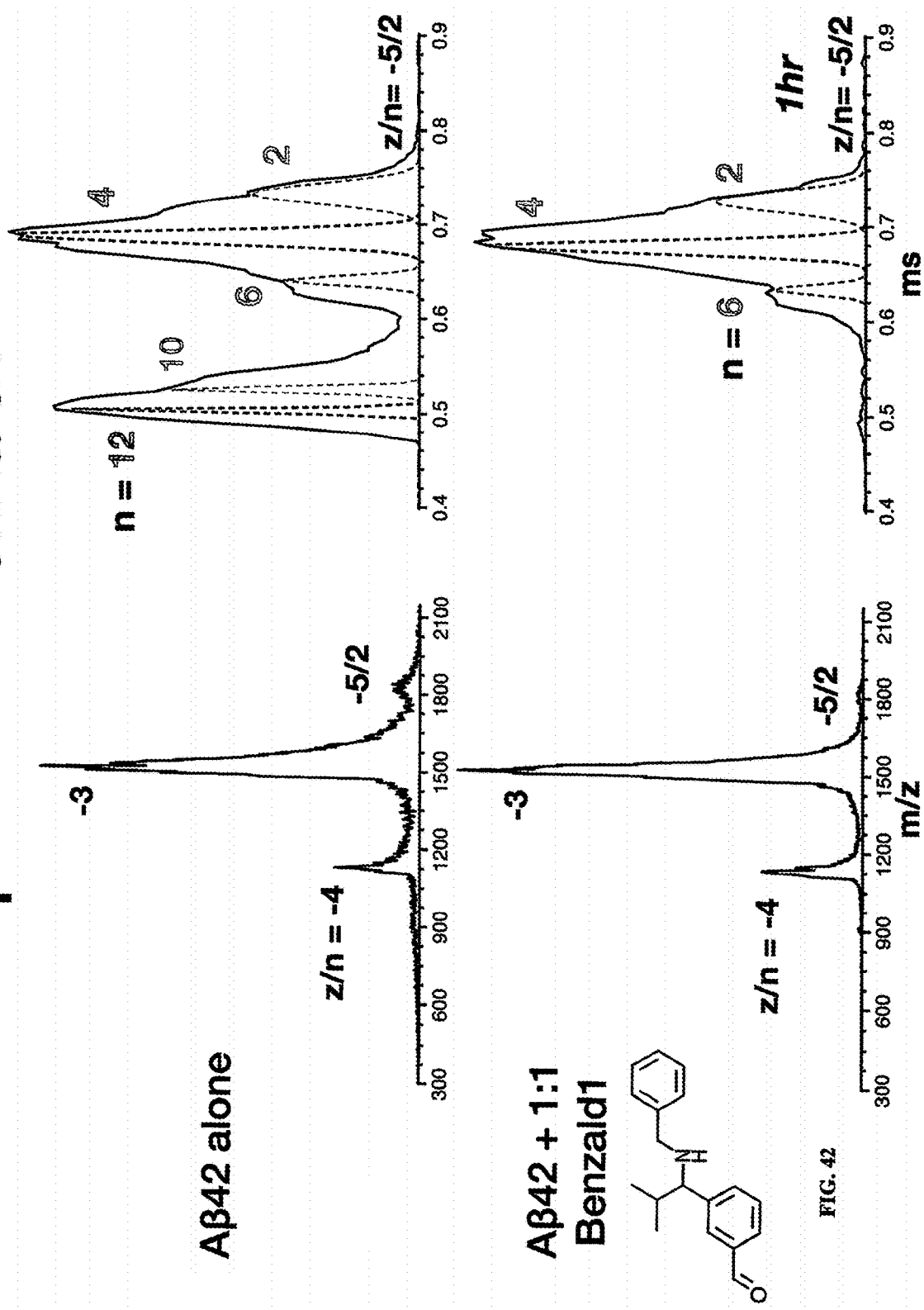
Figure 43:
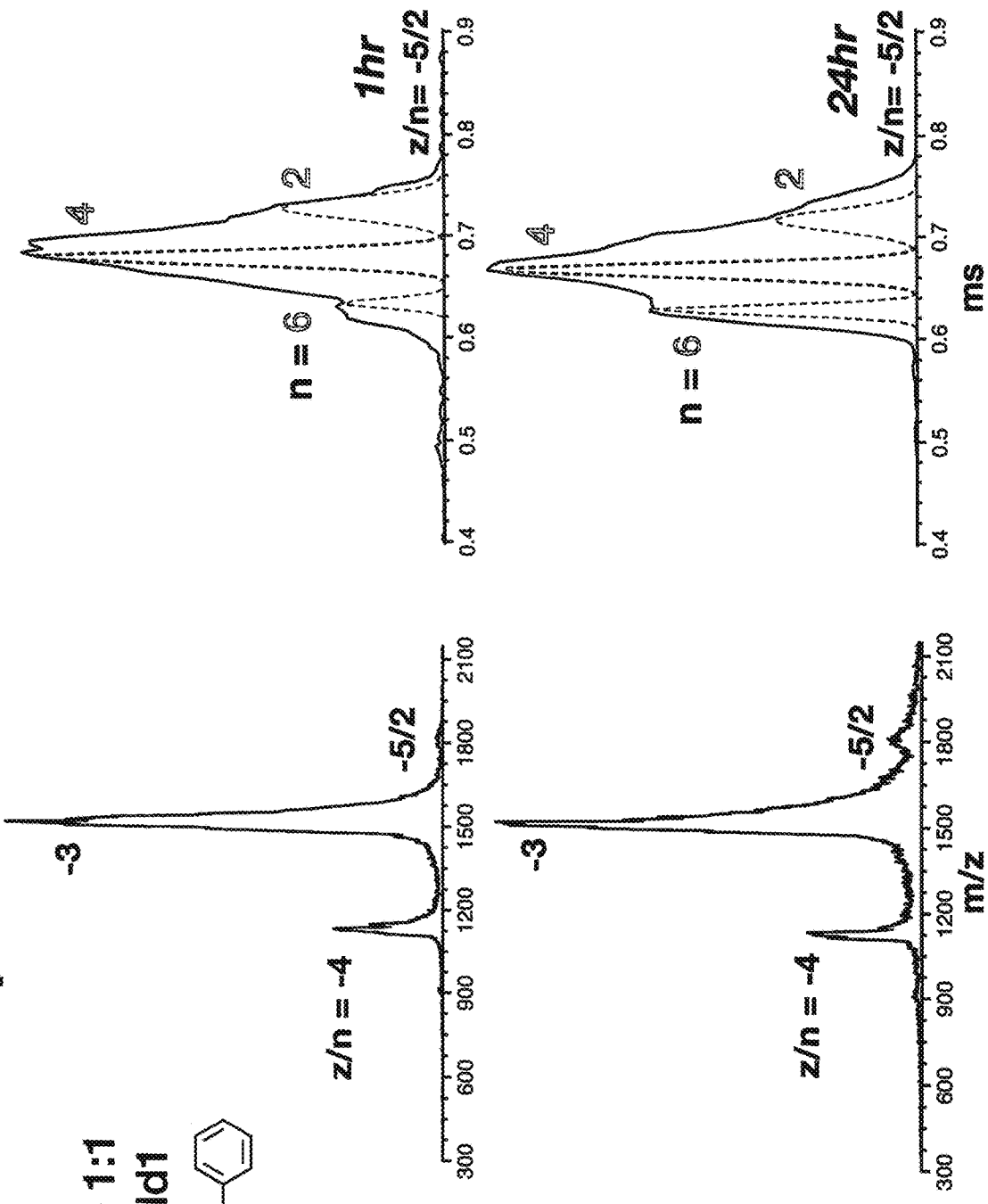
Figure 45:
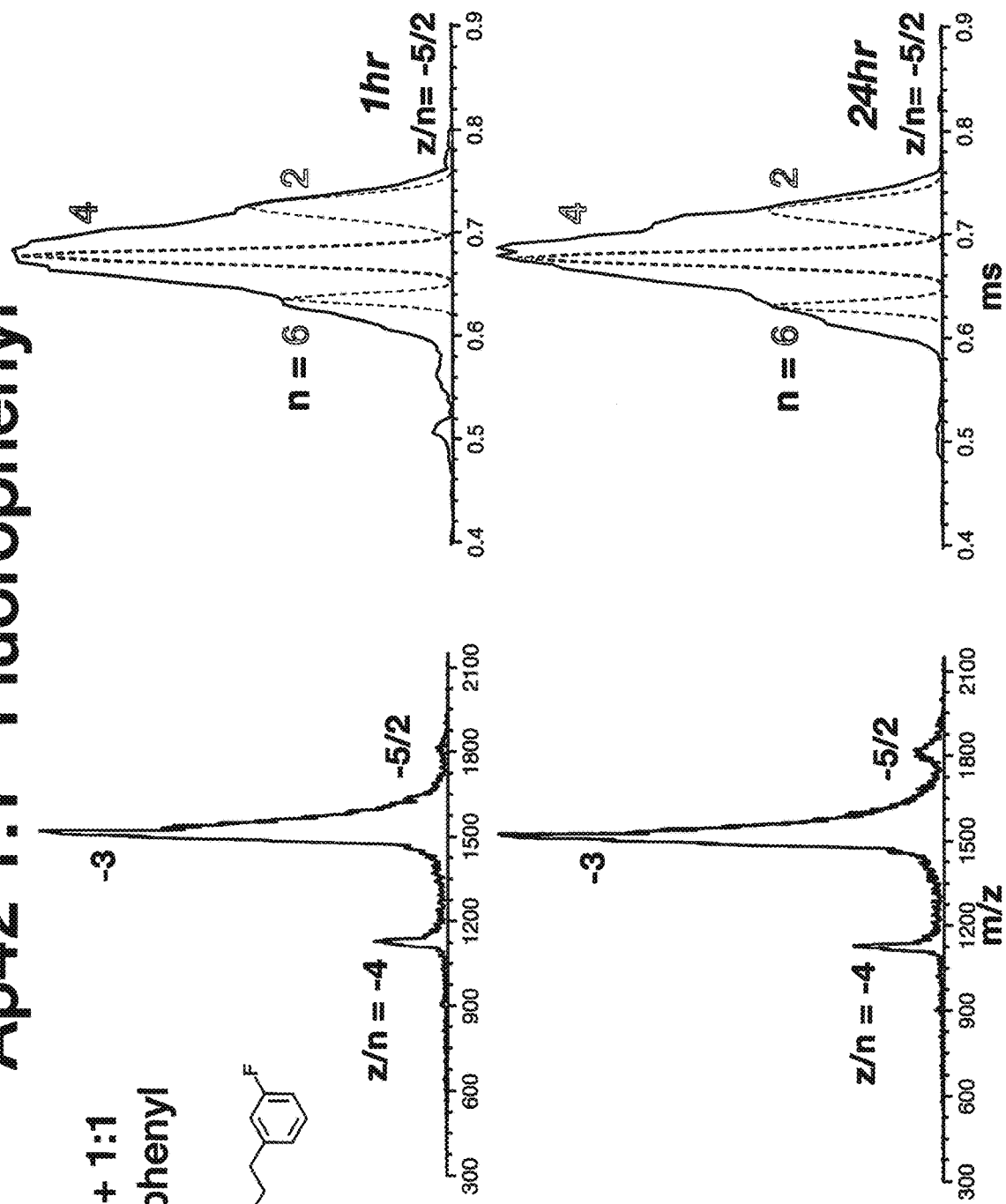
Figure 46:
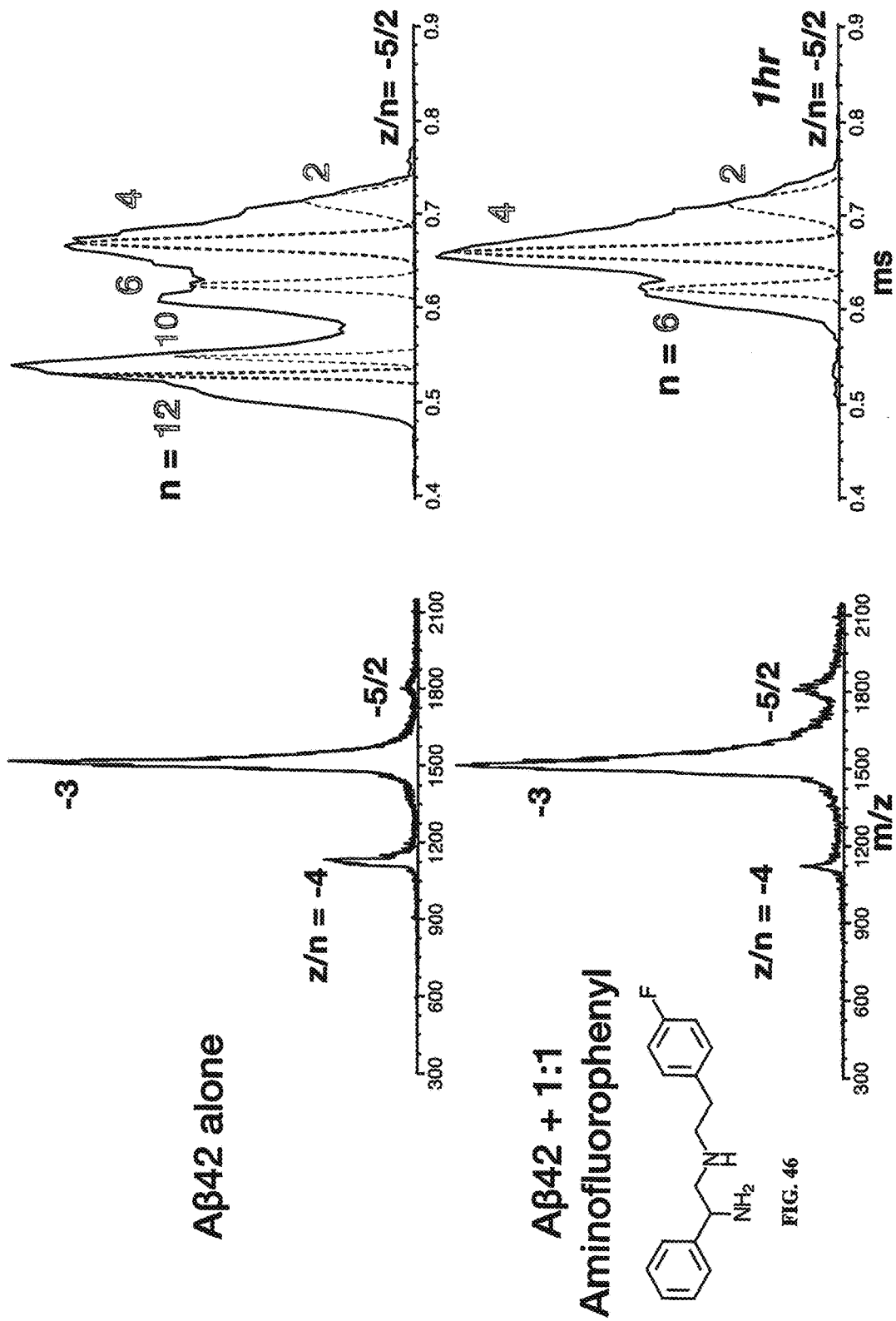
Figure 47:
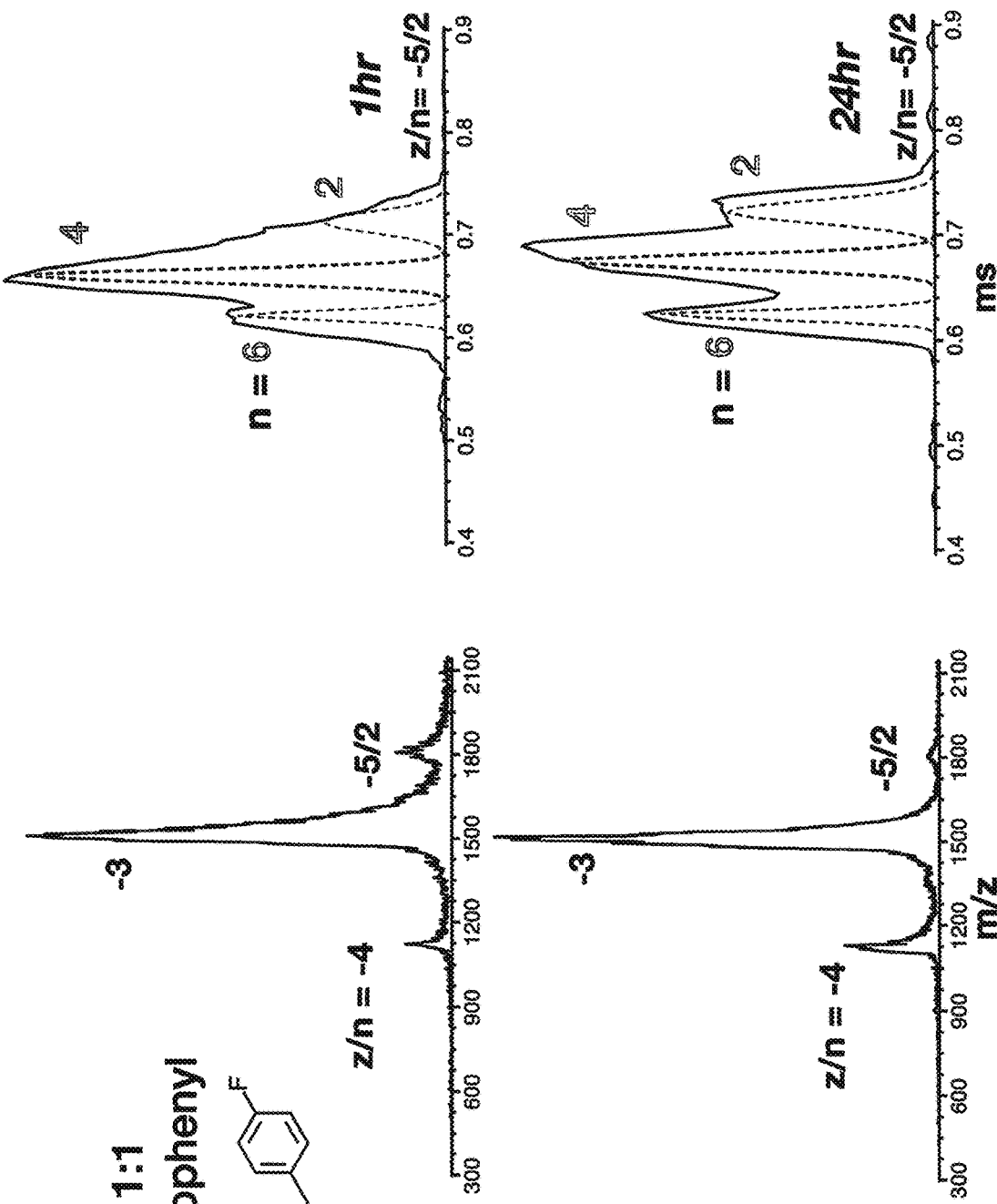
Figure 48:
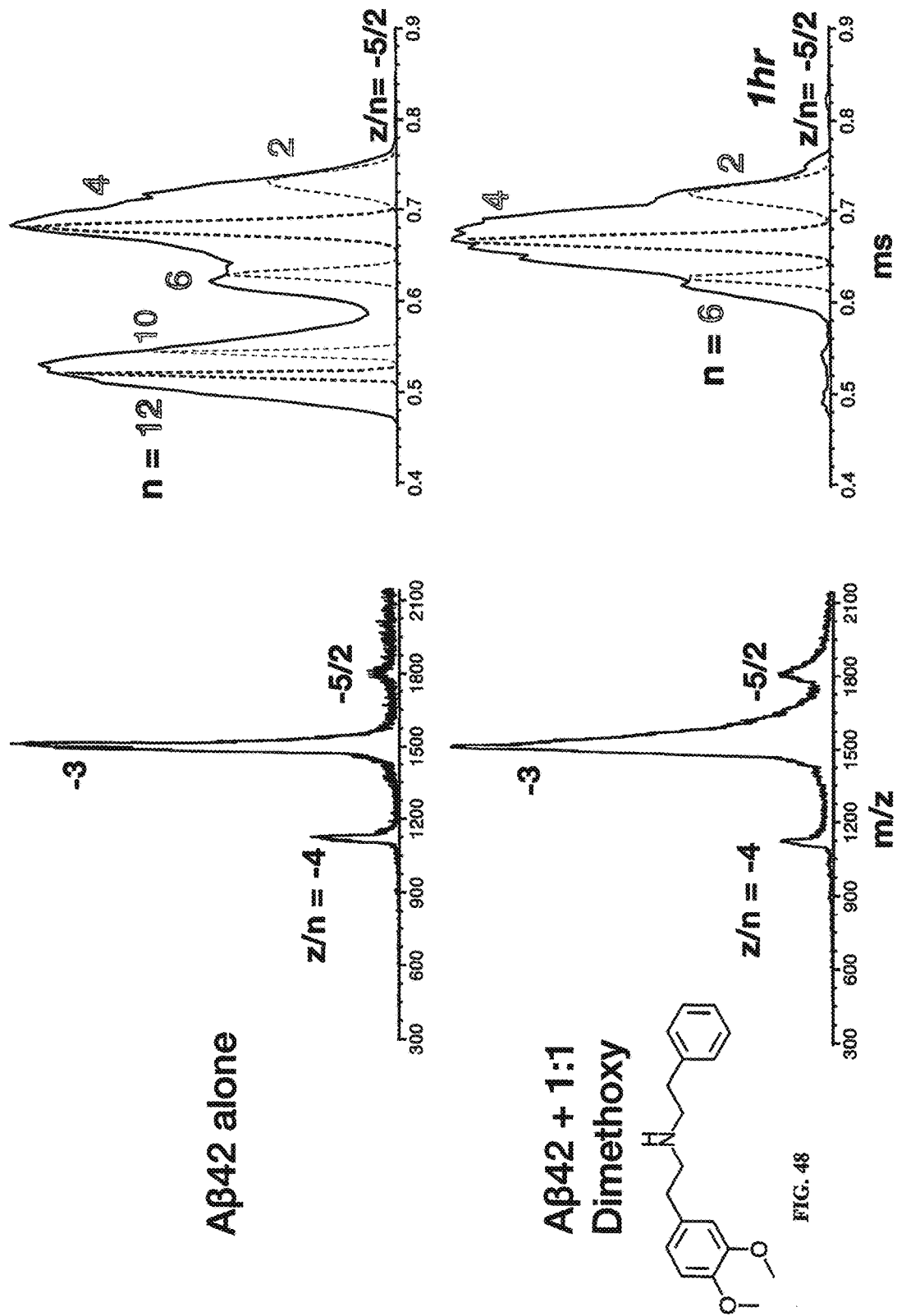
Figure 49:
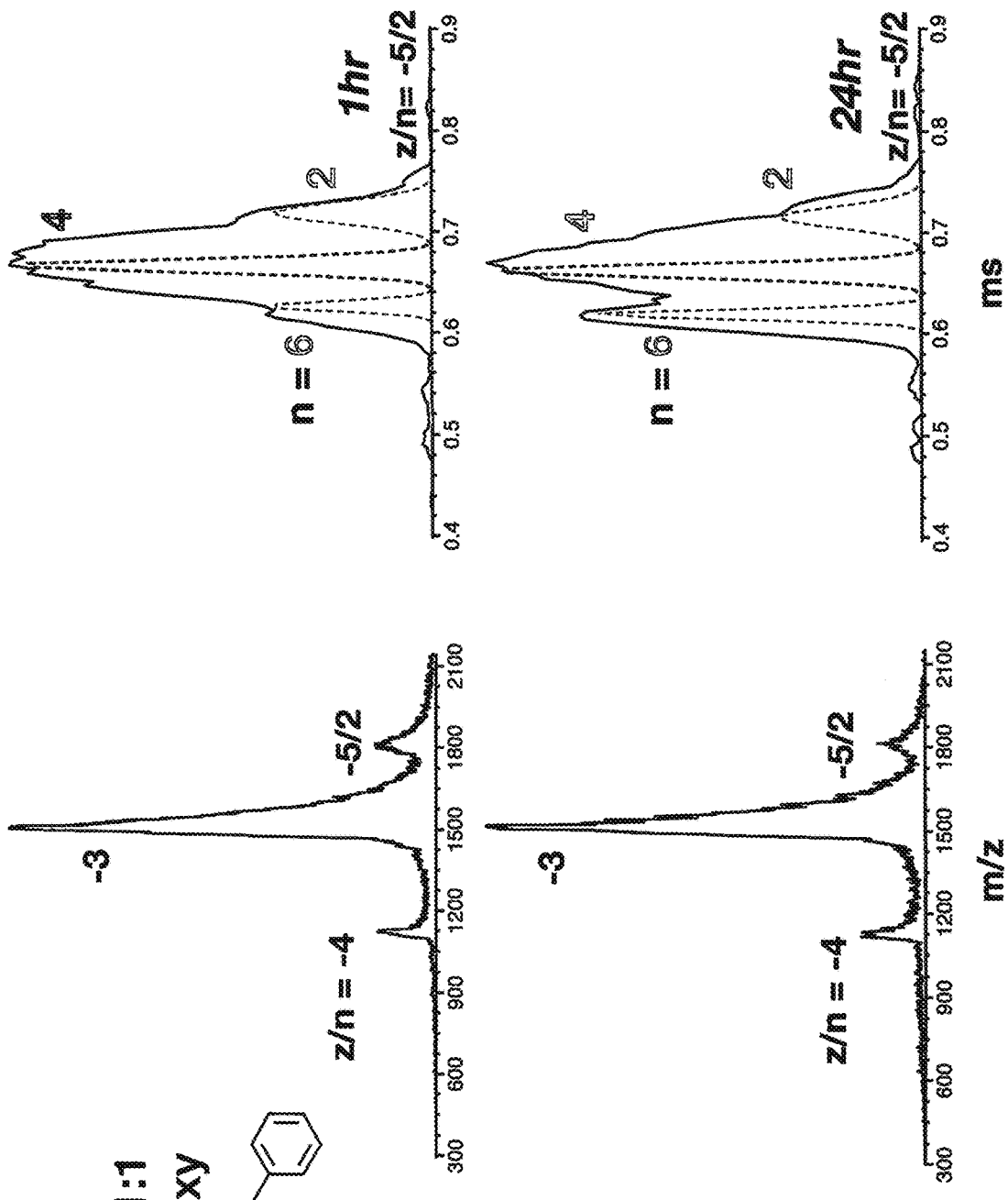
Figure 50:
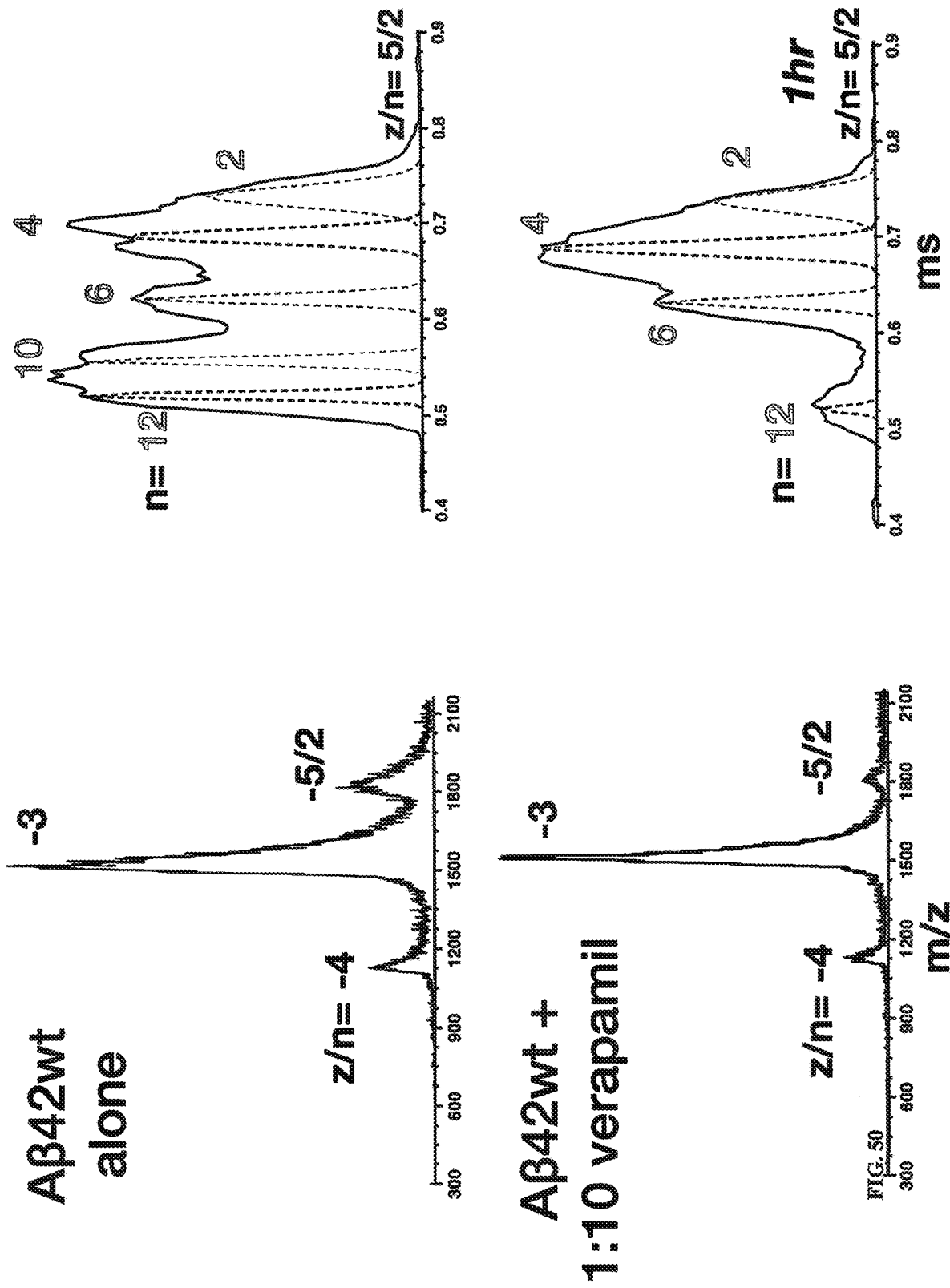
Figure 51:
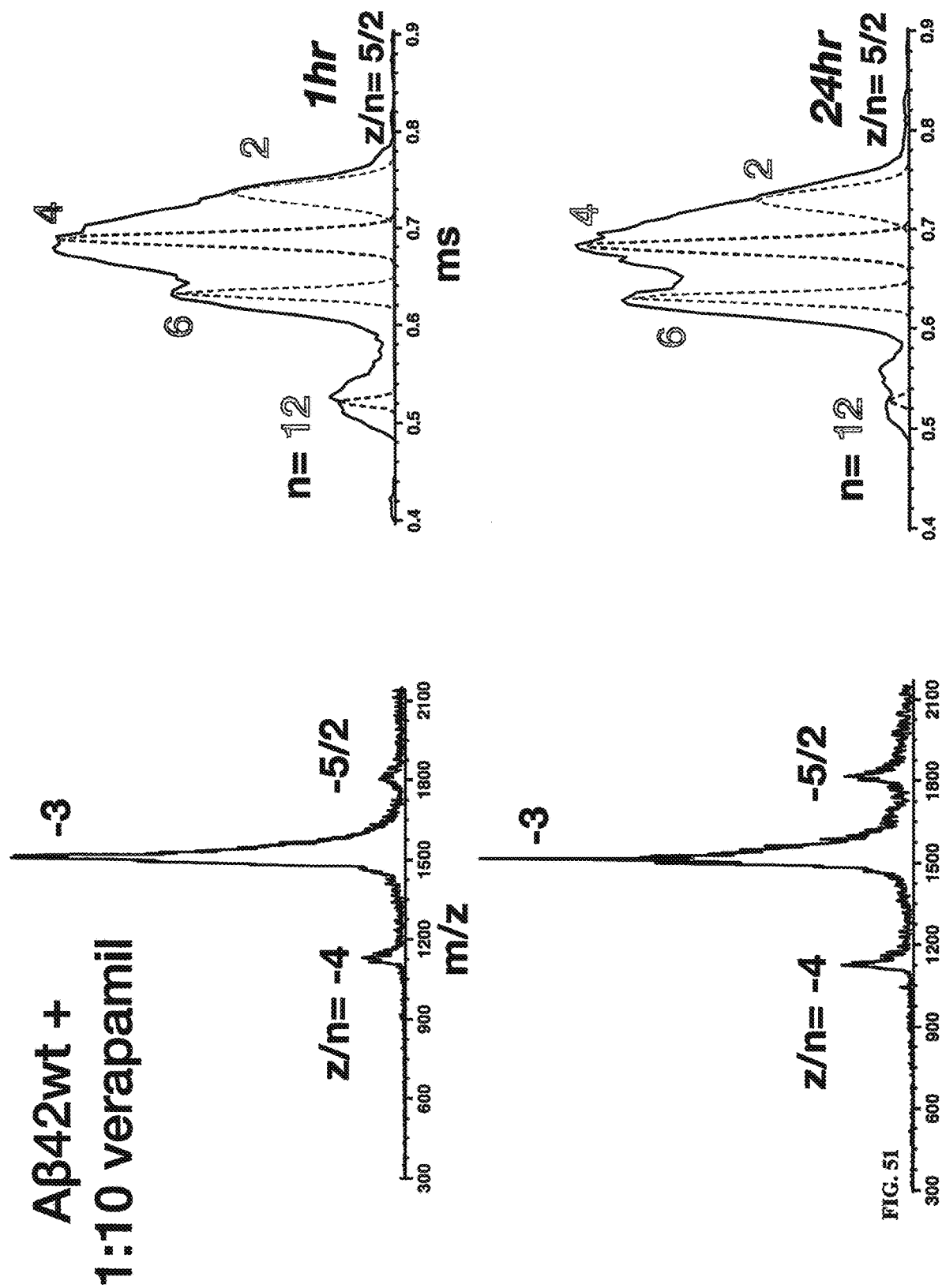
Figure 52:
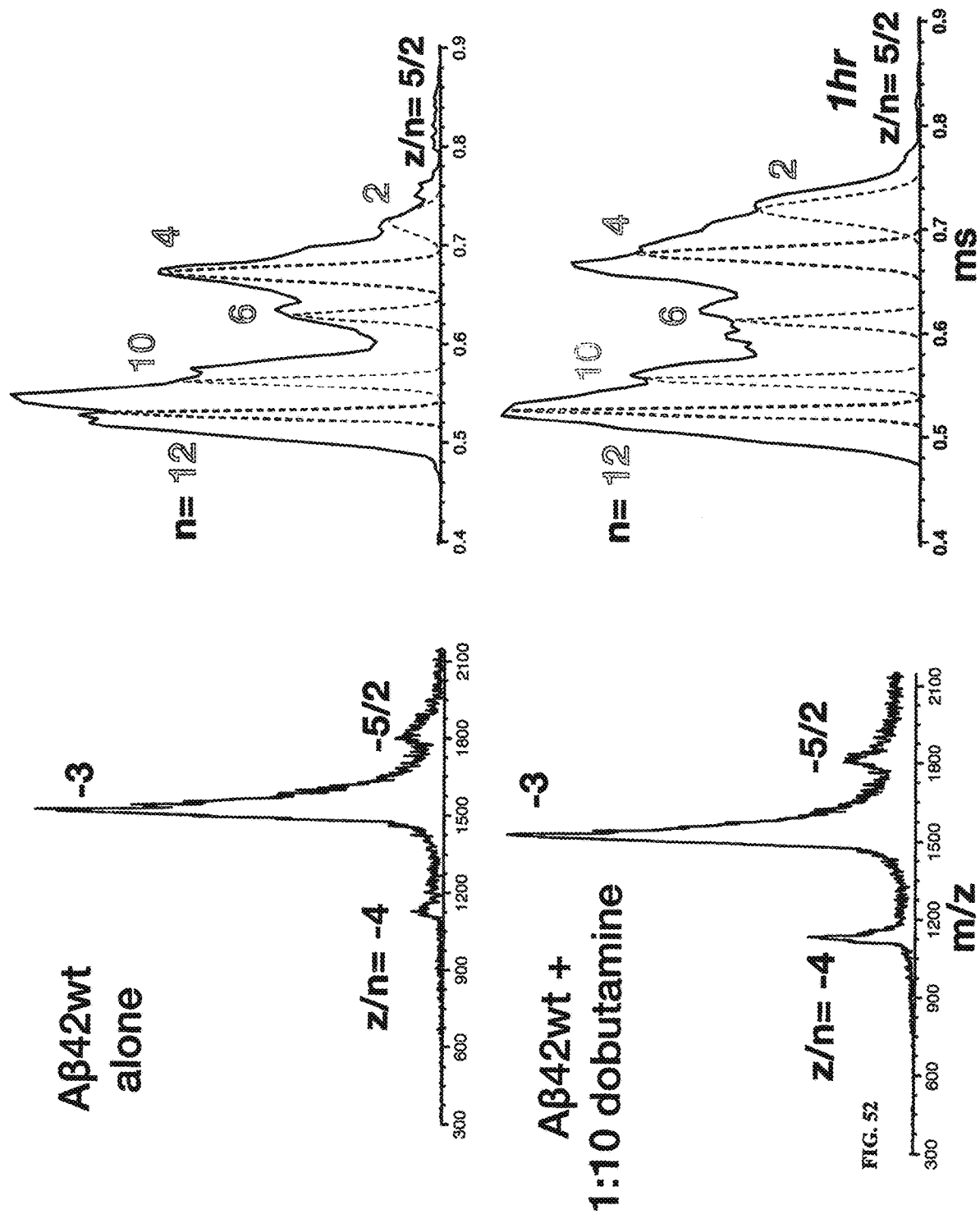
Figure 53:
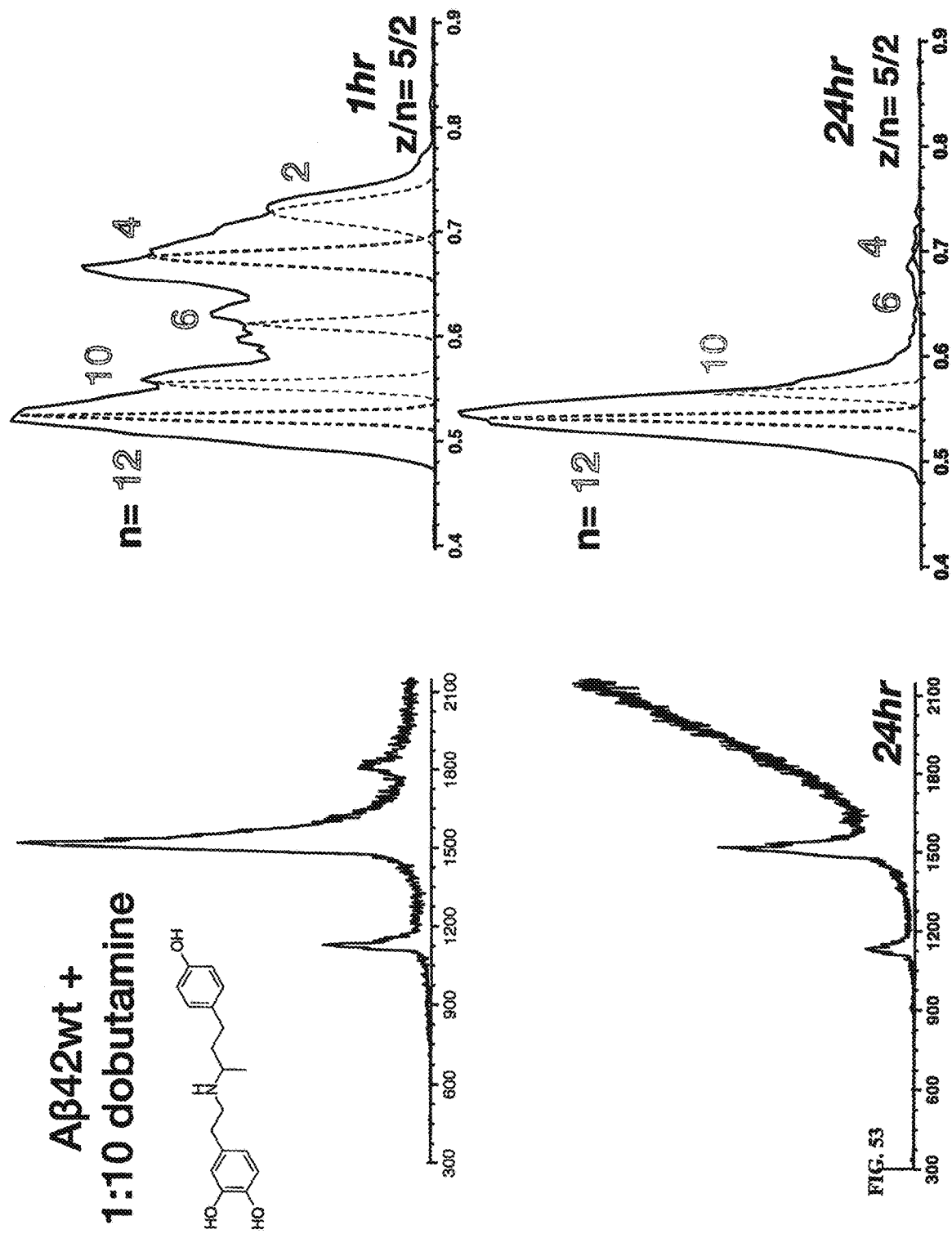
Figure 54:
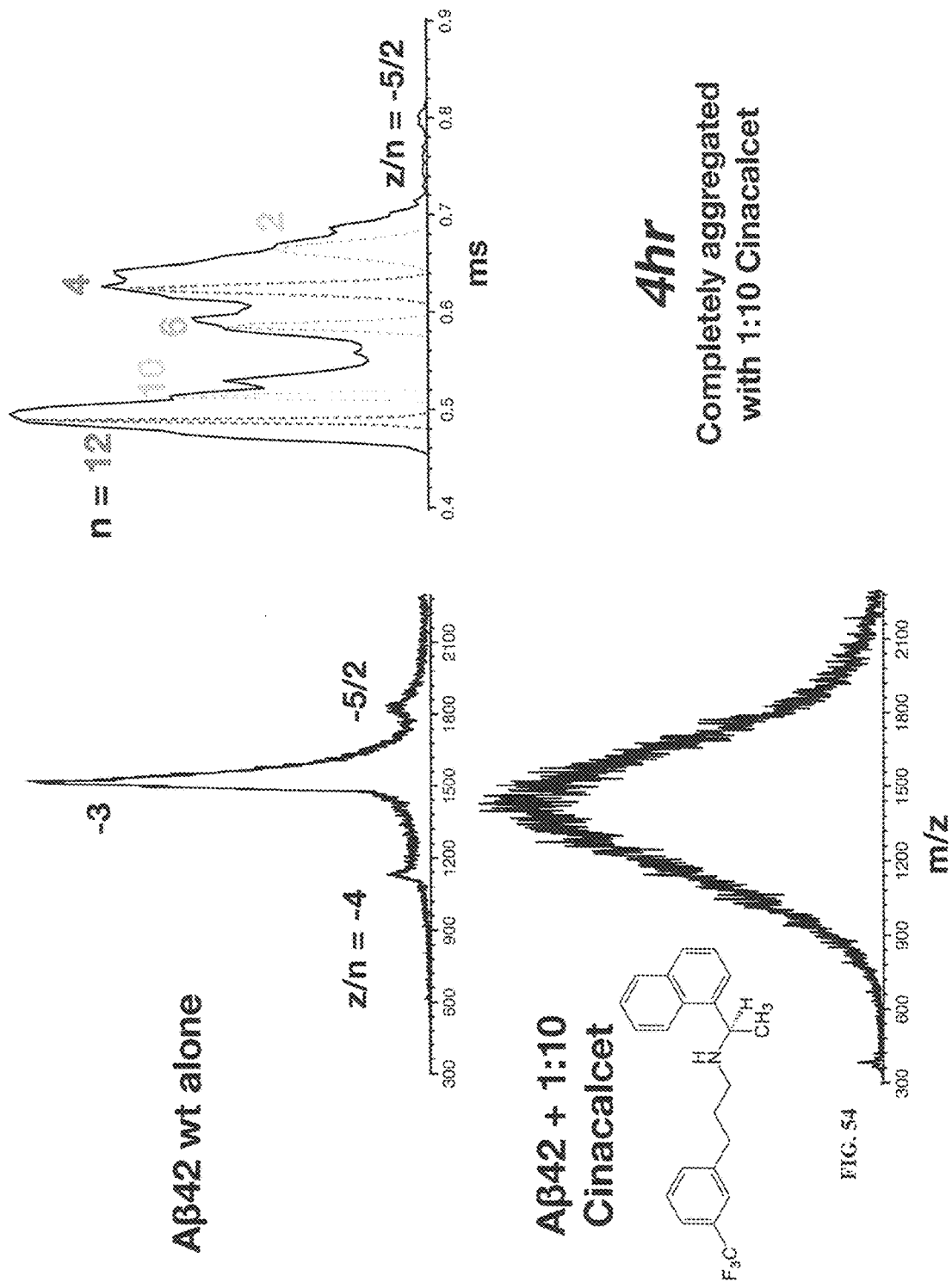
Figure 55:
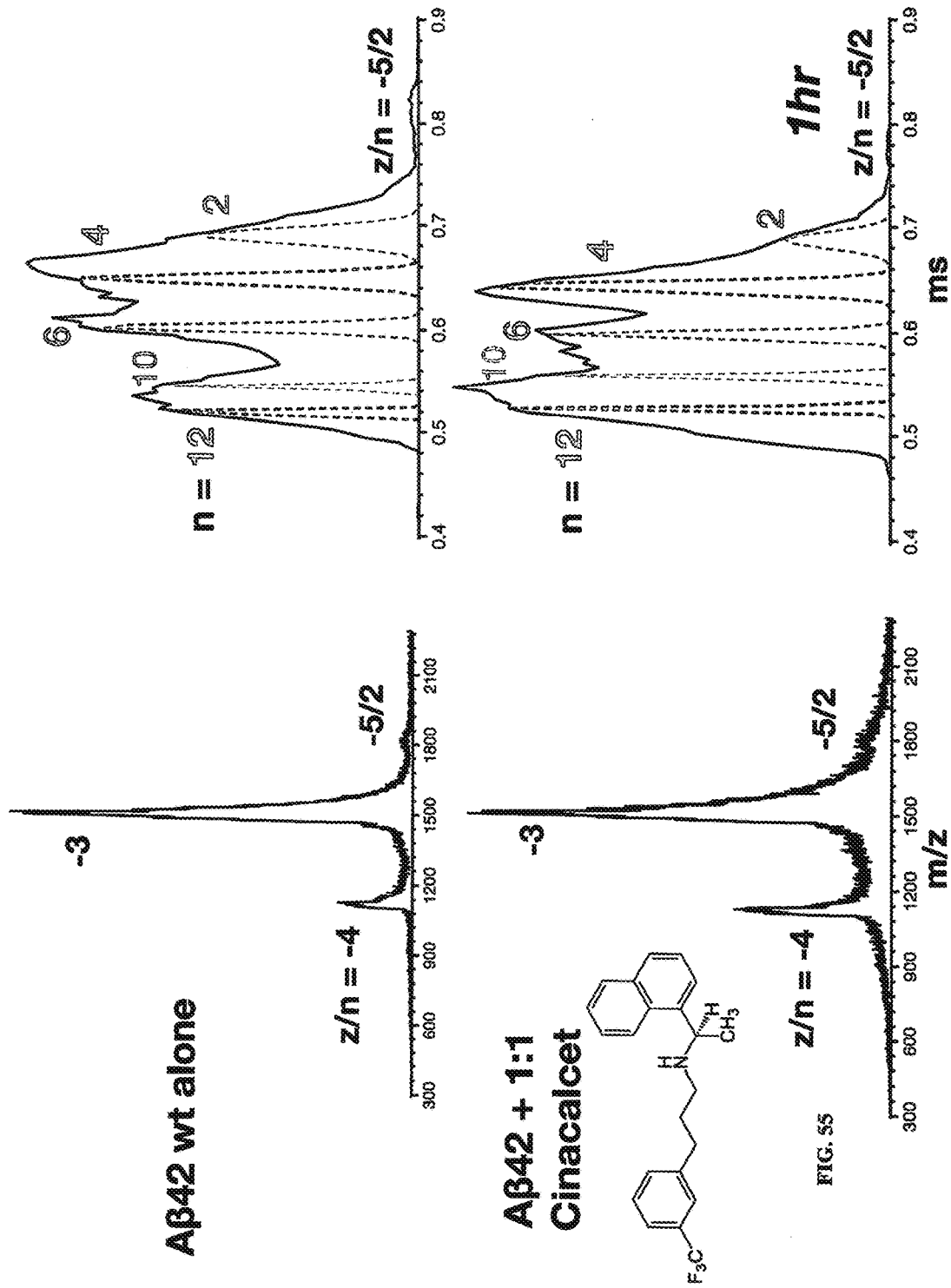
Figure 56:
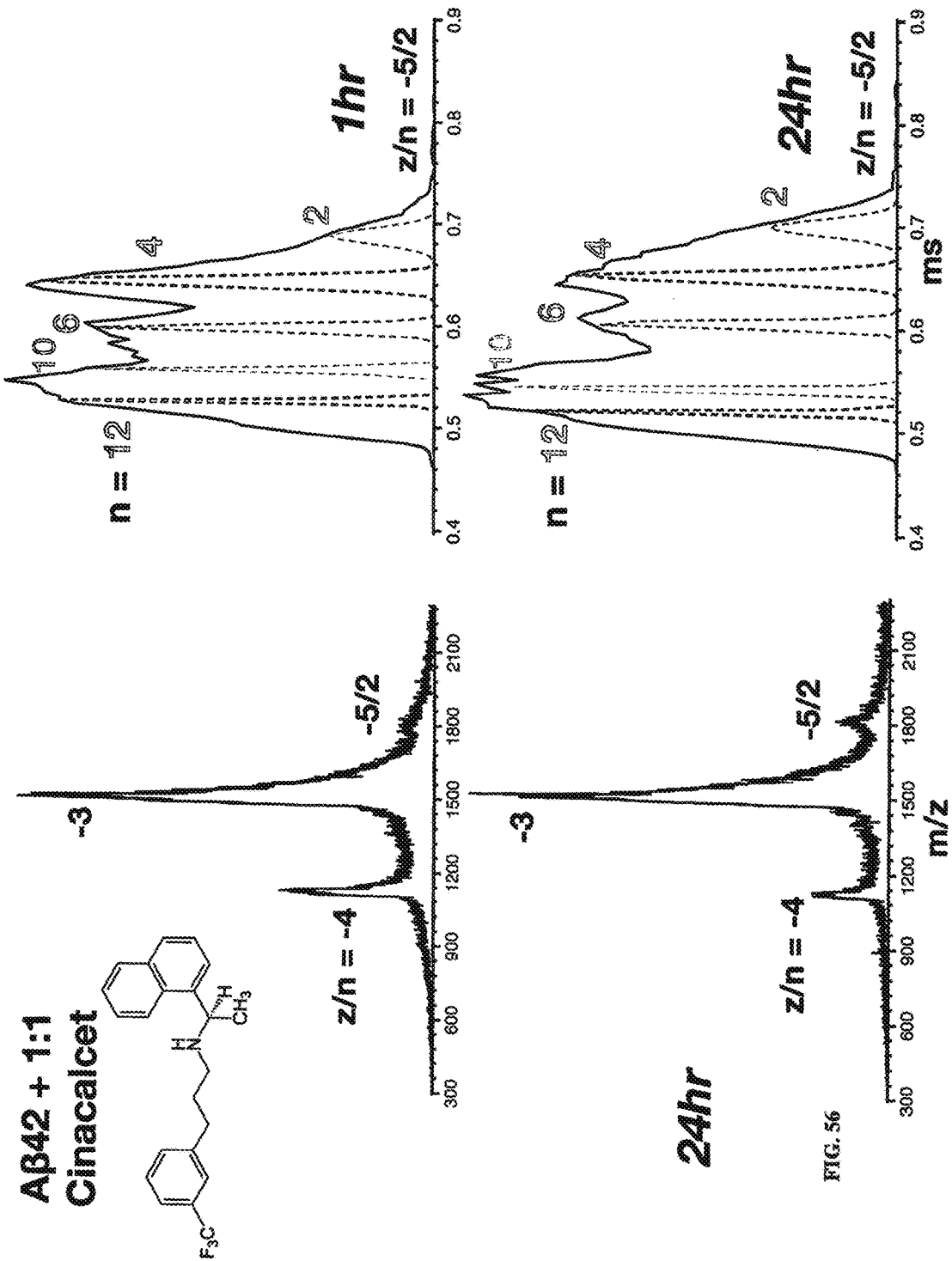

FIG. 7 shows that at day 2, cross sections are comparable to the wild type. The introduction of the A0107 compound reduces relative amounts of earlier arriving structures in z/n=−4 ATD.

FIG. 8 shows that the presence of earlier arriving structures in z/n=−3 ATD disappear sometime between 26 and 30 hours incubation time with A0107. After 29 hours, dodecamer formation is still inhibited in z/n=−5/2 ATD, These observations demonstrate that 4-({[3-(1-pyrrolidinylmethyl)benzyl]amino}-methyl)benzonitrile (A0107) is an inhibitor of Aβ42 wt dodecamer formation, slowing hexamer growth as well. Cinacalcet did not inhibit dodecamer formation in the performed assays.

The invention claimed is:

1. A compound of Formula 120:

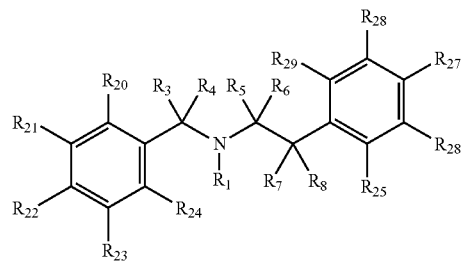

or a pharmaceutically acceptable salt, stereoisomer, or tautomer thereof, wherein:

$R_1$ is H;

$R_3$ is H;

$R_4$ is H;

$R_5$ is H;

$R_6$ is alkynyl;

$R_7$ is H;

$R_8$ is H;

$R_{20}$ is H, alkyl, alkyl(Oaryl), alkyl(aryl), alkyl(heterocyclyl), alkyl(heteroaryl), alkenyl, or alkynyl;

$R_{21}$ is H, alkyl, alkyl(Oaryl), alkyl(heterocyclyl), alkyl(heteroaryl), alkenyl, or alkynyl;

$R_{22}$ is H, NR'R", or NR'C(O)R;

$R_{23}$ is H, alkyl, alkyl(Oaryl), alkyl(heterocyclyl), alkyl(heteroaryl), alkenyl, or alkynyl;

$R_{24}$ is H, alkyl, alkyl(Oaryl), alkyl(aryl), alkyl(heterocyclyl), alkyl(heteroaryl), alkenyl, or alkynyl;

$R_{25}$ is H, alkyl, alkyl(Oaryl), alkyl(aryl), alkyl(heterocyclyl), alkyl(heteroaryl), alkenyl, or alkynyl;

$R_{26}$ is halogen;

$R_{27}$ is H, alkyl, alkyl(Oaryl), alkyl(aryl), alkyl(heterocyclyl), alkyl(heteroaryl), alkenyl, or alkynyl;

$R_{28}$ is H, alkyl, alkyl(Oaryl), alkyl(aryl), alkyl(heterocyclyl), alkyl(heteroaryl), alkenyl, or alkynyl;

$R_{29}$ is H, alkyl, alkyl(Oaryl), alkyl(aryl), alkyl(heterocyclyl), alkyl(heteroaryl), alkenyl, or alkynyl;

R is alkyl or aryl;

R' is H, alkyl, or aryl; and

R" is H, alkyl, or aryl.

2. The compound of claim 1, or a pharmaceutically acceptable salt, stereoisomer, or tautomer thereof, wherein $R_6$ is C≡CH.

3. The compound of claim 1, or a pharmaceutically acceptable salt, stereoisomer, or tautomer thereof, wherein $R_{22}$ is H.

4. The compound of claim 1, or a pharmaceutically acceptable salt, stereoisomer, or tautomer thereof, wherein $R_{26}$ is F.

5. The compound of claim 1, or a pharmaceutically acceptable salt, stereoisomer, or tautomer thereof, wherein $R_{26}$ is Cl.

6. The compound of claim 1, wherein the compound is:
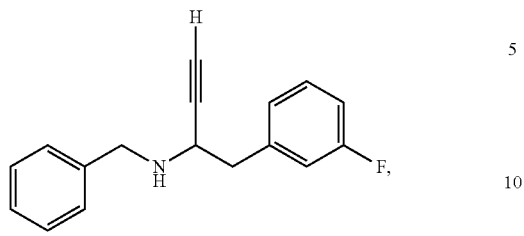
or a pharmaceutically acceptable salt or stereoisomer thereof.
* * * * *